United States Patent
Hasegawa et al.

(10) Patent No.: US 9,829,792 B2
(45) Date of Patent: Nov. 28, 2017

(54) MONOMER, POLYMER, POSITIVE RESIST COMPOSITION, AND PATTERNING PROCESS

(71) Applicant: Shin-Etsu Chemical Co., Ltd., Chiyoda-ku, Tokyo (JP)

(72) Inventors: Koji Hasegawa, Joetsu (JP); Jun Hatakeyama, Joetsu (JP); Teppei Adachi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 3 days.

(21) Appl. No.: 15/204,145

(22) Filed: Jul. 7, 2016

(65) Prior Publication Data
US 2017/0008982 A1 Jan. 12, 2017

(30) Foreign Application Priority Data
Jul. 9, 2015 (JP) .................... 2015-137416

(51) Int. Cl.
| | | |
|---|---|---|
| *G03F 7/004* | (2006.01) | |
| *G03F 7/38* | (2006.01) | |
| *C07C 69/54* | (2006.01) | |
| *C07C 69/73* | (2006.01) | |
| *C08F 220/18* | (2006.01) | |
| *C08F 220/30* | (2006.01) | |
| *G03F 7/039* | (2006.01) | |
| *C08F 128/06* | (2006.01) | |
| *C08F 116/10* | (2006.01) | |
| *C08F 116/14* | (2006.01) | |
| *C08F 124/00* | (2006.01) | |
| *C08F 116/36* | (2006.01) | |
| *G03F 7/16* | (2006.01) | |
| *G03F 7/20* | (2006.01) | |
| *G03F 7/32* | (2006.01) | |
| *C07D 307/00* | (2006.01) | |
| *C07C 69/76* | (2006.01) | |
| *C07C 69/86* | (2006.01) | |

(52) U.S. Cl.
CPC ............ *G03F 7/0392* (2013.01); *C07C 69/54* (2013.01); *C07C 69/73* (2013.01); *C07C 69/76* (2013.01); *C07C 69/86* (2013.01); *C07D 307/00* (2013.01); *C08F 116/10* (2013.01); *C08F 116/14* (2013.01); *C08F 116/36* (2013.01); *C08F 124/00* (2013.01); *C08F 128/06* (2013.01); *C08F 220/18* (2013.01); *C08F 220/30* (2013.01); *G03F 7/039* (2013.01); *G03F 7/0397* (2013.01); *G03F 7/168* (2013.01); *G03F 7/2002* (2013.01); *G03F 7/322* (2013.01); *G03F 7/38* (2013.01); *C07C 2101/08* (2013.01); *C07C 2101/14* (2013.01); *C07C 2103/74* (2013.01); *C08F 2220/302* (2013.01)

(58) Field of Classification Search
CPC ........ G03F 7/0392; G03F 7/0397; G03F 7/38; C07C 69/54; C08F 220/18; C08F 220/30; C08F 2220/302
USPC ..... 430/270.1, 326, 910; 526/313, 320, 326; 560/220, 221, 224
See application file for complete search history.

(56) References Cited

U.S. PATENT DOCUMENTS

| | | | |
|---|---|---|---|
| 6,746,817 B2 | 6/2004 | Takeda et al. | |
| 7,482,108 B2 | 1/2009 | Matsumaru et al. | |
| 8,951,709 B2* | 2/2015 | Masuyama | G03F 7/0046 430/270.1 |
| 9,017,918 B2 | 4/2015 | Hatakeyama et al. | |
| 2009/0170029 A1* | 7/2009 | Choi | C07C 69/54 430/285.1 |

FOREIGN PATENT DOCUMENTS

| | | |
|---|---|---|
| EP | 0 473 547 A1 | 4/1992 |
| JP | 4-230645 A | 8/1992 |
| JP | 2005-84365 A | 3/2005 |
| JP | 2006-45311 A | 2/2006 |
| JP | 2006-169302 A | 6/2006 |
| JP | 3865048 B2 | 1/2007 |
| JP | 2012-12577 A | 1/2012 |

* cited by examiner

*Primary Examiner* — John S Chu
(74) *Attorney, Agent, or Firm* — Westerman, Hattori, Daniels & Adrian, LLP

(57) ABSTRACT

A polymer comprising recurring units derived from a polymerizable monomer having two structures of hydroxyphenyl methacrylate having a hydroxy group substituted with an acid labile group is used as base resin in a positive resist composition, especially chemically amplified positive resist composition. The resist composition forms a resist film which is processed by lithography into a pattern of good profile having a high resolution, minimal edge roughness, and etch resistance.

12 Claims, No Drawings

MONOMER, POLYMER, POSITIVE RESIST COMPOSITION, AND PATTERNING PROCESS

CROSS-REFERENCE TO RELATED APPLICATION

This non-provisional application claims priority under 35 U.S.C. §119(a) on Patent Application No. 2015-137416 filed in Japan on Jul. 9, 2015, the entire contents of which are hereby incorporated by reference.

TECHNICAL FIELD

This invention relates to a monomer, a polymer, a positive resist composition comprising the polymer, and a patterning process using the composition.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of wavelength 13.5 nm, and double patterning version of the ArF lithography, on which active research efforts have been made.

With respect to high-energy radiation of very short wavelength such as electron beam (EB) or x-ray, hydrocarbons and similar light elements used in ArF resist materials have little absorption. Then polyhydroxystyrene base resist materials are under consideration.

Resist materials for EB lithography are practically used in the mask image writing application. The exposure system for mask manufacturing made a transition from the laser beam exposure system to the EB exposure system to increase the accuracy of line width. Since a further size reduction becomes possible by increasing the accelerating voltage of the electron gun in the EB exposure system, the accelerating voltage increased from 10 kV to 30 kV and reached 50 kV in the current mainstream system, with a voltage of 100 kV being under investigation.

As the accelerating voltage increases, a lowering of sensitivity of resist film becomes of concern. As the accelerating voltage increases, the influence of forward scattering in a resist film becomes so reduced that the contrast of electron image writing energy is improved to ameliorate resolution and dimensional control whereas electrons can pass straightforward through the resist film so that the resist film becomes less sensitive. Since the mask exposure tool is designed for exposure by direct continuous writing, a lowering of sensitivity of resist film leads to an undesirably reduced throughput. Due to a need for higher sensitivity, chemically amplified resist compositions are contemplated.

Thinning of resist film is in progress to facilitate reduction of pattern feature in the EB lithography for mask manufacturing and to prevent the pattern from collapsing due to a higher aspect ratio during development. In the case of photolithography, a thinning of resist film greatly contributes to resolution improvement. This is because introduction of chemical mechanical polishing (CMP) or the like has driven forward device planarization. In the case of mask manufacture, substrates are flat, and the thickness of processable substrates (e.g., Cr, MoSi or $SiO_2$) is predetermined by a percent light shield or phase shift control. The resist film must be improved in dry etch resistance before it can be reduced in thickness.

It is generally believed that there is a correlation between the carbon density and the dry etch resistance of resist film. As carbon density increases, etch resistance improves. Indene copolymers described in Patent Document 1 and acenaphthylene copolymers described in Patent Document 2 are expected to have a high carbon density and improved etch resistance due to a robust main chain of cycloolefin structure.

Also, with respect to the soft x-ray (EUV) lithography at wavelength 5-20 nm, the reduced absorption of carbon atoms was reported. Increasing the carbon density is effective not only for improving dry etch resistance, but also for increasing the transmittance in the soft x-ray wavelength region.

As the feature size is reduced, image blurs due to acid diffusion become a problem. To insure resolution for fine patterns with a size of 45 nm et seq., not only an improvement in dissolution contrast is requisite, but control of acid diffusion is also important, as known from previous reports. Since chemically amplified resist compositions are designed such that sensitivity and contrast are enhanced by acid diffusion, an attempt to minimize acid diffusion by reducing the temperature and/or time of post-exposure bake (PEB) fails, resulting in drastic reductions of sensitivity and contrast. Since the distance of acid diffusion is closely related to the type of acid labile group, it would be desirable to have an acid labile group which permits deprotection reaction to proceed at a very short distance of acid diffusion.

It is pointed out that an ArF resist material (typically methacrylic acid) having a carboxyl group substituted with an acid labile group swells in alkaline developer. On the other hand, a KrF resist material (typically hydroxystyrene) having a phenolic hydroxyl group substituted with an acid labile group little swells. However, hydroxystyrene allows for substantial acid diffusion, indicating a decline of resolution. There is a desire to have a resist material featuring reduced acid diffusion and least swell in alkaline developer.

Patent Document 3 describes hydroxyphenyl methacrylate as adhesive group. It is effective for reducing swell like hydroxystyrene and more effective for suppressing acid diffusion than hydroxystyrene. Patent Document 3 also describes a hydroxyphenyl methacrylate substituted with an acid labile group.

Addition of an acid generator capable of generating a bulky acid is effective for suppressing acid diffusion. It is then proposed to incorporate recurring units derived from an onium salt having a polymerizable unsaturated bond in a polymer as the acid generator. Patent Documents 4 to 6 disclose sulfonium salts having a polymerizable unsaturated bond, capable of generating a sulfonic acid and similar iodonium salts.

CITATION LIST

Patent Document 1: JP 3865048
Patent Document 2: JP-A 2006-169302

Patent Document 3: JP-A 2012-012577
Patent Document 4: JP-A H04-230645 (EP 0473547)
Patent Document 5: JP-A 2005-084365
Patent Document 6: JP-A 2006-045311 (U.S. Pat. No. 7,482,108)

DISCLOSURE OF INVENTION

An object of the present invention is to provide a positive resist composition, typically chemically amplified positive resist composition, comprising a specific polymer, which exhibits a high resolution surpassing prior art positive resist compositions, and forms a resist film having a minimal LER, a good pattern profile after exposure, and high etch resistance. Another object is to provide a polymer suited as base resin in the resist composition, a monomer polymerizable into the polymer, and a pattern forming process using the resist composition.

The inventors made investigations to seek for a positive resist composition which exhibits a high resolution, minimal LER, a good pattern profile, and improved etch resistance. Methacrylic acid polymers are effective for suppressing acid diffusion while phenolic hydroxyl groups are characterized by a less swell in alkaline aqueous solution than carboxyl groups. A resist composition containing a polymer comprising recurring units derived from hydroxyphenyl methacrylate as adhesive group is successful in reducing a swell amount while suppressing acid diffusion. A resist composition containing a polymer comprising recurring units derived from naphthol methacrylate in which naphthol is substituted with an acid labile group also undergoes less swell in alkaline solution, whereas the naphthol methacrylate from which the acid labile group has been deprotected has a low alkaline dissolution rate and hence, a low dissolution contrast. A resist composition containing a polymer comprising recurring units derived from hydroxyphenyl methacrylate which is protected with an acid labile group is also insufficient in dissolution contrast. It has been found that better results are obtained when a polymer comprising recurring units derived from a polymerizable monomer having two structures of hydroxyphenyl methacrylate having a hydroxy group substituted with an acid labile group is used as base resin in a positive resist composition, especially chemically amplified positive resist composition.

Toward the goals of suppressing acid diffusion and improving dissolution contrast and etch resistance, the inventors have found that using the specific polymer as a base resin, there is obtained a positive resist composition, especially chemically amplified positive resist composition, which is effective for suppressing swell during development in alkaline aqueous solution and effective for suppressing acid diffusion, forms a pattern after exposure with high resolution, good profile and minimal edge roughness, prevents pattern collapse, and exhibits improved etch resistance. The resulting positive resist composition is best suited as the fine pattern-forming material for the manufacture of VLSIs and photomasks.

The positive resist composition comprising the specific polymer as a base resin has many advantages including a high dissolution contrast of a resist film, an acid diffusion suppressing effect, a high resolution, exposure latitude, process adaptability, a good pattern profile after exposure, and etch resistance. Because of these advantages, the positive resist composition is best suited as the fine pattern-forming material for the manufacture of VLSIs and masks.

In one aspect, the invention provides a monomer having the formula (1).

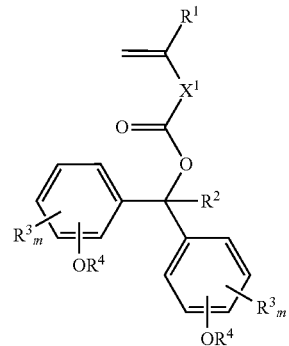

(1)

Herein $R^1$ is hydrogen or methyl, $R^2$ is hydrogen or a straight, branched or cyclic $C_1$-$C_{15}$ monovalent hydrocarbon group in which any constituent —$CH_2$— may be replaced by —O—, —C(=O)—, —C(=O)—O— or —O—C(=O)—, $R^3$ is each independently hydrogen, cyano, nitro, or a straight, branched or cyclic $C_1$-$C_6$ monovalent hydrocarbon group in which any constituent —$CH_2$— may be replaced by —O—, —C(=O)—, —C(=O)—O— or —O—C(=O)—, $R^4$ is each independently hydrogen or an acid labile group, $X^1$ is a single bond, a $C_1$-$C_{12}$ linking group having an ester moiety, ether moiety or lactone ring, a phenylene group or naphthylene group, and m is an integer of 1 to 4.

In another aspect, the invention provides a polymer comprising recurring units (a) having the formula (A).

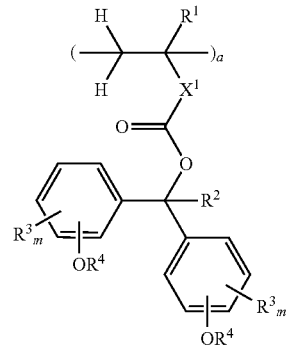

(A)

Herein $R^1$, $R^2$, $R^3$, $R^4$, $X^1$, and m are as defined above, and a is a positive number in the range: $0 < a \leq 1.0$.

In either embodiment, the acid labile group is preferably t-butyl, t-pentyl, methylcyclopentyl, ethylcyclopentyl, methylcyclohexyl, ethylcyclohexyl, methyladamantyl, ethyladamantyl, t-butoxycarbonyl, t-pentyloxycarbonyl, or —$CR^5R^6$—O—$R^7$, wherein $R^5$ and $R^6$ are each independently hydrogen or a straight or branched $C_1$-$C_4$ alkyl group, $R^7$ is a straight, branched or cyclic $C_1$-$C_{12}$ alkyl group or straight, branched or cyclic $C_2$-$C_{12}$ alkenyl group.

The polymer may further comprise recurring units (b) containing an adhesive group selected from the group consisting of hydroxyl, carboxyl, lactone ring, carbonate, thiocarbonate, carbonyl, cyclic acetal, ether, ester, sulfonic acid ester, cyano, amide, and —O—C(=O)-G- wherein G is sulfur or NH.

Typically the recurring unit (b) is a unit containing a phenolic hydroxyl group. The recurring unit containing a phenolic hydroxyl group is preferably selected from recurring units (b1) to (b9) having the formulae (B1) to (B9).

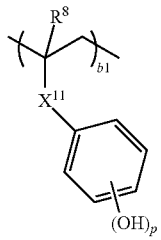
(B1)

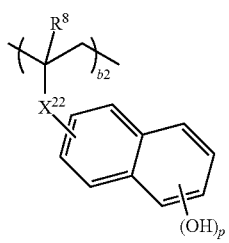
(B2)

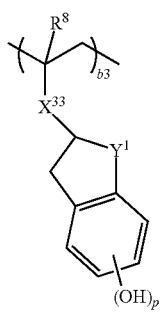
(B3)

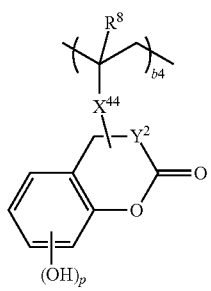
(B4)

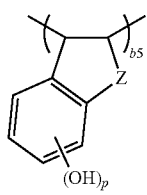
(B5)

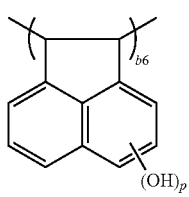
(B6)

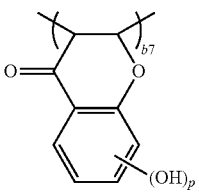
(B7)

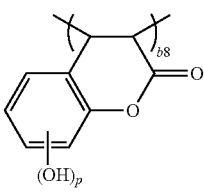
(B8)

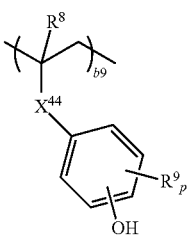
(B9)

Herein $R^8$ is hydrogen or methyl, $R^9$ is $C_1$-$C_4$ alkyl, —C(=O)—$R^{9a}$, —O—C(=O)—$R^{9a}$, —C(=O)—O—$R^{9a}$, cyano or nitro group, $X^{11}$ and $X^{22}$ are each independently a single bond or —C(=O)—O—$R^{10a}$—, $X^{33}$ and $X^{44}$ each are —C(=O)—O—$R^{10a}$—, $R^{9a}$ is $C_1$-$C_4$ alkyl or $C_2$-$C_4$ alkenyl, $R^{10a}$ is a single bond or a straight, branched or cyclic $C_1$-$C_{10}$ alkylene group, $Y^1$ and $Y^2$ are each independently methylene or ethylene, z is methylene, oxygen or sulfur, p is 1 or 2, b1 to b9 are numbers in the range: $0 \le b1 < 1.0$, $0 \le b2 < 1.0$, $0 \le b3 < 1.0$, $0 \le b4 < 1.0$, $0 \le b5 < 1.0$, $0 \le b6 < 1.0$, $0 \le b7 < 1.0$, $0 \le b8 < 1.0$, $0 \le b9 < 1.0$, and $0 < b1+b2+b3+b4+b5+b6+b7+b8+b9 < 1.0$.

The polymer may further comprise recurring units of at least one type selected from recurring units (c1) to (c5) having the formulae (C1) to (C5).

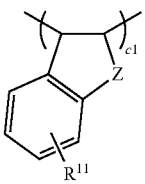
(C1)

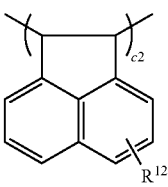
(C2)

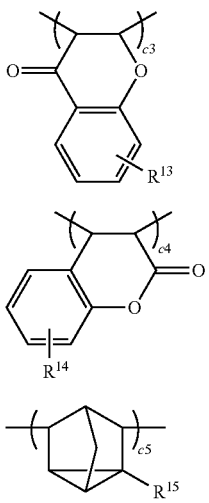

(C3)

(C4)

(C5)

Herein $R^{11}$ to $R^{15}$ are each independently hydrogen, $C_1$-$C_{30}$ alkyl, $C_1$-$C_{30}$ alkyl in which one or more or all carbon-bonded hydrogen atoms are substituted by halogen, $C_1$-$C_8$ alkoxy, $C_1$-$C_8$ alkanoyl, $C_2$-$C_8$ alkoxycarbonyl, $C_6$-$C_{10}$ aryl, halogen, or 1,1,1,3,3,3-hexafluoro-2-propanol group.
Z is methylene, oxygen or sulfur, c1 to c5 are numbers in the range: $0 \le c1<1.0$, $0 \le c2<1.0$, $0 \le c3<1.0$, $0 \le c4<1.0$, $0 \le c5<1.0$, and $0<c1+c2+c3+c4+c5<1.0$.

The polymer may further comprise recurring units of at least one type selected from sulfonium salt-containing recurring units (d1) to (d3) having the formulae (D1) to (D3).

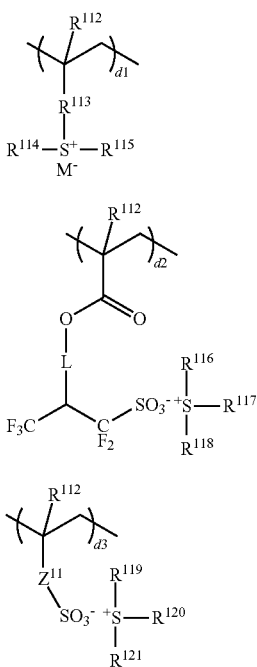

(D1)

(D2)

(D3)

Herein $R^{112}$ is hydrogen or methyl, $R^{113}$ is a single bond, phenylene, —O—$R^{122}$—, or —C(=O)—$Z^{22}$—$R^{122}$—, $Z^{22}$ is oxygen or NH, $R^{122}$ is a straight, branched or cyclic $C_1$-$C_6$ alkylene, $C_2$-$C_6$ alkenylene or phenylene group, which may contain a carbonyl, ester, ether or hydroxyl moiety, L is a single bond or —$Z^{33}$—C(=O)—O—, Z is a straight, branched or cyclic $C_1$-$C_{20}$ divalent hydrocarbon group which may be substituted with a heteroatom, $Z^{11}$ is a single bond, methylene, ethylene, phenylene, fluorinated phenylene, —O—$R^{122}$—, or —C(=O)—$Z^{44}$—$R^{123}$—, $Z^{44}$ is oxygen or NH, $R^{123}$ is a straight, branched or cyclic $C_1$-$C_6$ alkylene, $C_2$-$C_6$ alkenylene or phenylene group, which may contain a carbonyl, ester, ether or hydroxyl moiety, M⁻ is a non-nucleophilic counter ion, $R^{114}$, $R^{116}$, $R^{117}$, $R^{118}$, $R^{119}$, $R^{120}$, and $R^{121}$ are each independently a straight, branched or cyclic $C_1$-$C_{20}$ monovalent hydrocarbon group which may contain a heteroatom, d1, d2 and d3 are numbers in the range: $0 \le d1 \le 0.5$, $0 \le d2 \le 0.5$, $0 \le d3 \le 0.5$, and $0<d1+d2+d3 \le 0.5$.

In a further aspect, the invention provides a positive resist composition comprising the polymer defined above, an organic solvent, and optionally a photoacid generator, dissolution regulator, basic compound and/or surfactant.

In a still further aspect, the invention provides a pattern forming process comprising the steps of coating the positive resist composition defined above onto a substrate, baking the coating to form a resist film, exposing the resist film to high-energy radiation, and developing the exposed resist film in a developer.

The positive resist composition, typically chemically amplified positive resist composition is used not only in the lithography for forming semiconductor circuits, but also in the formation of mask circuit patterns, micromachines, and thin-film magnetic head circuits.

Advantageous Effects of Invention

The positive resist composition comprising a polymer comprising recurring units derived from a polymerizable monomer defined herein as a base resin exhibits a very high contrast of alkaline dissolution rate before and after exposure, a high resolution, improved profile and reduced LER of a pattern after exposure, a suppressed rate of acid diffusion, and etch resistance. Because of these advantages, the positive resist composition, especially chemically amplified positive resist composition is best suited as a fine pattern-forming material for the manufacture of VLSIs and photomasks and a pattern-forming material for EUV lithography.

Description of Embodiments

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In the chemical formula, the broken line designates a valence bond, Me is methyl, Ac is acetyl, and Ph is phenyl.

The abbreviations have the following meaning.
EB: electron beam
EUV: extreme ultraviolet
PAG: photoacid generator
PES: post-exposure bake
LER: line edge roughness
LWR: line width roughness
Mw: weight average molecular weight
Mn: number average molecular weight
Mw/Mn: molecular weight distribution or dispersity
GPC: gel permeation chromatography

Monomer

A first embodiment of the invention is a polymerizable monomer having the formula (1).

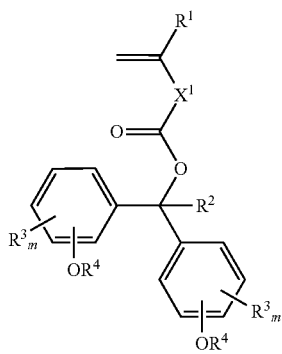

(1)

Herein $R^1$ is hydrogen or methyl, $R^2$ is hydrogen or a straight, branched or cyclic $C_1$-$C_{15}$ monovalent hydrocarbon group in which any constituent —$CH_2$— may be replaced by —O—, —C(=O)—, —C(=O)—O— or —O—C(=O)—, $R^3$ is each independently hydrogen, cyano, nitro, or a straight, branched or cyclic $C_1$-$C_5$ monovalent hydrocarbon group in which any constituent —$CH_2$— may be replaced by —O—, —C(=O)—, —C(=O)—O— or —O—C(=O)—, $R^4$ is each independently hydrogen or an acid labile group, $X^1$ is a single bond, a $C_1$-$C_{12}$ linking group having an ester moiety, ether moiety or lactone ring, a phenylene group or naphthylene group, and m is an integer of 1 to 4.

$R^2$ is hydrogen or a straight, branched or cyclic $C_1$-$C_{15}$ monovalent hydrocarbon group, examples of which include alkyl groups such as methyl, ethyl, propyl, isopropyl, n-butyl, s-butyl, t-butyl, cyclopentyl, cyclohexyl, 2-ethylhexyl, n-octyl, norbornyl, tricyclodecanyl, and adamantyl, aryl groups such as phenyl and naphthyl, aralkyl groups such as benzyl and phenethyl, and alkylaryl groups such as methylphenyl and ethylphenyl. Preferably $R^2$ is hydrogen, methyl, ethyl, propyl, butyl, acetoxymethyl, 1-acetoxyethyl, 2-acetoxyethyl, phenyl, naphthyl, methylphenyl and as methoxyphenyl.

$R^3$ is preferably hydrogen, cyano, nitro, methyl, ethyl, propyl, isopropyl, butyl, t-butyl, cyclopentyl, cyclohexyl, formyl, acetyl, propionyl, isopropionyl, pivaloyl, methacryloyl, acryloyl, methoxycarbonyl, ethoxycarbonyl, t-butoxycarbonyl, cyclohexanecarbonyl, methoxy, ethoxy, formyloxy, acetyloxy, propionyloxy, isopropionyloxy, or pivaloyloxy.

$R^4$ is hydrogen or an acid labile group, examples of which will be described later. Typical acid labile groups include t-butyl, t-pentyl, methylcyclopentyl, ethylcyolopentyl, methylcyclohexyl, ethylcyclohexyl, methyladamantyl, ethyladamantyl, t-butoxycarbonyl, t-pentyloxycarbonyl, and —$CR^5R^6$—O—$R^7$ wherein $R^5$ and $R^6$ are each independently hydrogen or a straight or branched $C_1$-$C_4$ alkyl group, and $R^7$ is a straight, branched or cyclic $C_1$-$C_{12}$ alkyl group or straight, branched or cyclic $C_2$-$C_{12}$ alkenyl group.

The method for the synthesis of the polymerizable monomer having formula (1) is not particularly limited and an optimum method may be selected in accordance with its structure. For example, the monomer having formula (1) may be synthesized by steps i) to v) as shown in the following reaction scheme.

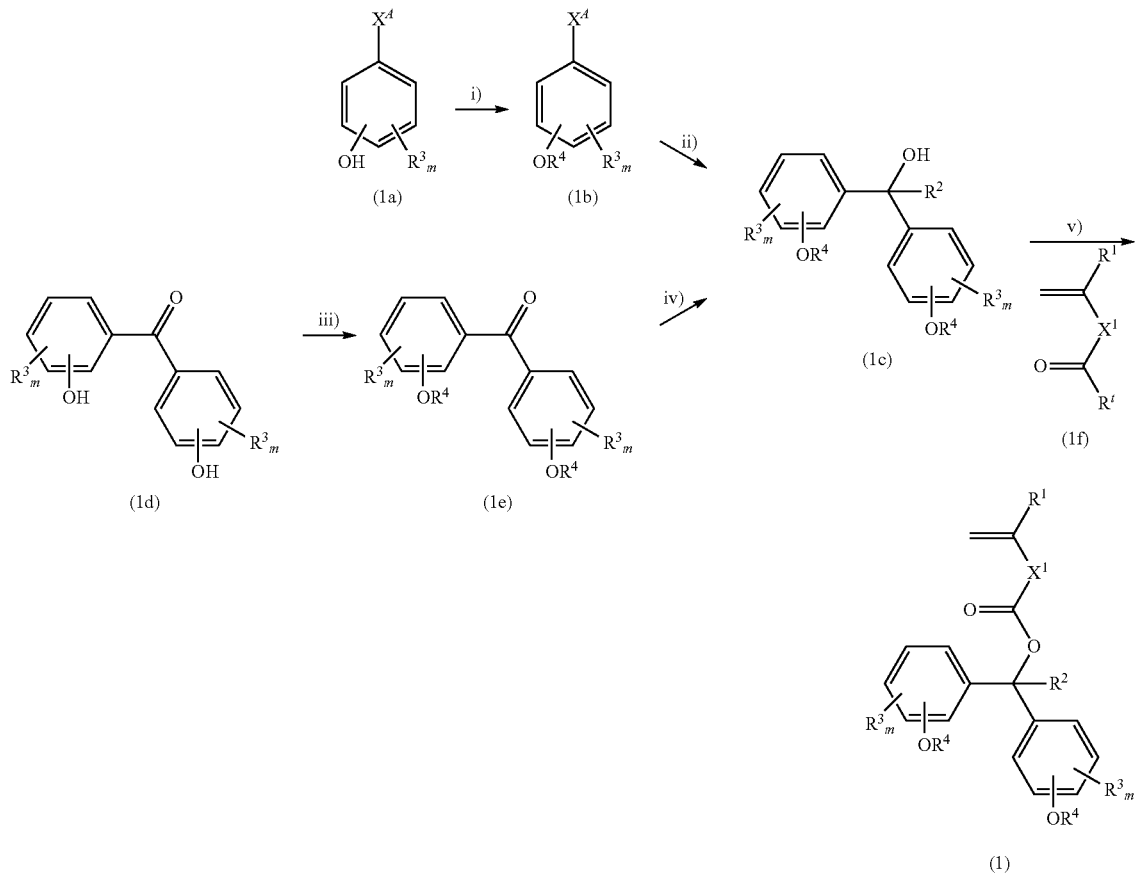

In the scheme, $R^1$ to $R^4$, $X^1$ and m are as defined above. $X^A$ is halogen. $R^r$ is halogen or —$OR^{rr}$ wherein $R^{rr}$ is hydrogen, methyl, ethyl or a group having the formula (1 g):

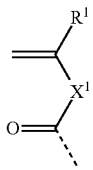

(1g)

wherein $R^1$ and $X^1$ are as defined above.

Step i) is to convert a phenol derivative (1a) to a halogenated aryl compound (1b) by protection. The reaction of step i) readily takes place under well-known conditions. For example, where $R^4$ is a tertiary alkyl group such as t-butyl, t-pentyl, methylcyclopentyl, ethylcyclopentyl, methylcyclohexyl, ethylcyclohexyl, methyladamantyl or ethyladamantyl, phenol derivative (1a) may be reacted with an olefin corresponding to $R^4$ such as isobutane or isopentylene in a solventless system or in a solvent such as toluene or hexane, in the presence of an acid catalyst and at a temperature of −20° C. to 50° C. Examples of the acid catalyst used herein include mineral acids such as hydrochloric acid, sulfuric acid, nitric acid and perchloric acid and organic acids such as methanesulfonic acid, trifluoromethanesulfonic acid, p-toluenesulfonic acid, and benzenesulfonic acid.

Step ii) is to convert halogenated aryl compound (1b) to an organometallic compound and then to an alcohol compound (1c). The reactions of step ii) may be readily performed by any well-known procedures. For example, the procedure according to the following scheme may be adopted.

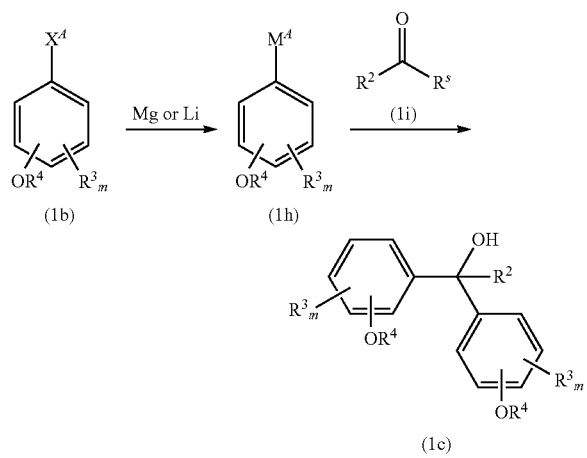

Herein $R^2$ to $R^4$, m and $X^A$ are as defined above. $M^A$ is Li, MgCl, MgBr or MgI. $R^s$ is a halogen atom or —$OR^{ss}$. $R^{ss}$ is a straight, branched or cyclic $C_1$-$C_6$ monovalent hydrocarbon group or a group of the following formula (1j):

(1j)

wherein $R^2$ is as defined above.

First, halogenated aryl compound (1b) is combined with Li or Mg in a solvent such as tetrahydrofuran or diethyl ether to form an organometallic reagent (1h). It is then reacted with a carbonyl compound (1i) to form alcohol compound (1c).

Step iii) is to convert a hydroxybenzophenone derivative (1d) to a benzophenone derivative (1e) by protection. The reaction may be readily performed by the same procedure as described for step i).

Step iv) is to convert benzophenone derivative (1e) to alcohol compound (1c) by reductive reaction of benzophenone derivative (1e) or nucleophilic addition reaction of an organometallic reagent. The reaction may be readily performed by any well-known procedures. For example, the procedure according to the following scheme may be adopted.

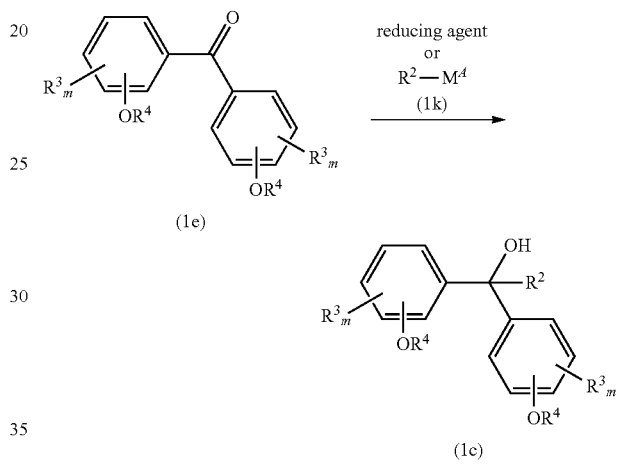

Herein $R^2$ to $R^4$, m and $M^A$ are as defined above.

Where $R^2$ is hydrogen, alcohol compound (1c) may be obtained from benzophenone derivative (1e) via reductive reaction of the carbonyl group. Suitable reducing agents used in step iv) are complex hydrides and alkoxy or alkyl derivatives thereof, including sodium borohydride, lithium borohydride, potassium borohydride, calcium borohydride, sodium aluminum hydride, lithium aluminum hydride, lithium triethylborohydride, lithium tri-s-butylborohydride, and potassium tri-s-butylborohydride. An appropriate amount of the reducing agent used is 0.3 to 4.0 moles, more preferably 0.5 to 2.0 moles per mole of benzophenone derivative (1e). The reaction may be performed in a solvent, and preferred solvents include water; ethers such as tetrahydrofuran (THF), diethyl ether, di-n-butyl ether, and 1,4-dioxane; hydrocarbons such as n-hexane, n-heptane, benzene, toluene, xylene and cumene; alcohols such as methanol, ethanol, isopropyl alcohol and t-butyl alcohol; dimethyl sulfoxide (DMSO), N,N-dimethylformamide (DMF); and aprotic polar solvents such as acetonitrile, which may be used alone or in admixture. The reaction temperature and time may widely vary depending on other conditions. Where the reducing agent is sodium borohydride, for example, the reaction temperature is in a range of −20° C. to 50° C., preferably −10° C. to 20° C. It is desired for higher yields that the reaction time be determined by monitoring the progress of reaction by silica gel thin-layer chromatography (TLC) or gas chromatography (GC) until completion. The reaction time is typically 0.5 to 5 hours. The alcohol compound (1c) may be recovered from the reaction mixture by ordinary aqueous workup. If necessary, it may be purified by any standard techniques such as distillation and chromatography.

Where $R^2$ is other than hydrogen, alcohol compound (1c) may be obtained from benzophenone derivative (1e) via nucleophilic addition reaction of an organometallic reagent (1k) thereto. An appropriate amount of organometallic reagent (1k) used is 1.0 to 5.0 moles, more preferably 1.5 to 3.0 moles per mole of benzophenone derivative (1e). The reaction may be performed in a solvent, and preferred solvents include ethers such as tetrahydrofuran (THF), diethyl ether, di-n-butyl ether, and 1,4-dioxane, and hydrocarbons such as n-hexane, n-heptane, benzene, toluene, xylene and cumene, which may be used alone or in admixture. The reaction temperature and time may widely vary depending on other conditions. Where the organometallic reagent is a Grignard reagent (of formula (1k) wherein $M^A$ is MgCl, MgBr or MgI), for example, the reaction temperature is in a range of −20° C. to 100° C., preferably 0° C. to 50° C. It is desired for higher yields that the reaction time be determined by monitoring the progress of reaction by silica gel TLC or GC until completion. The reaction time is typically 0.5 to 5 hours. The alcohol compound (1c) may be recovered from the reaction mixture by ordinary aqueous workup. If necessary, it may be purified by any standard techniques such as distillation and chromatography.

Step v) is by reacting alcohol compound (1c) with an esterifying agent (1f) to form the desired monomer (1). The reaction of step v) may be readily performed by any well-known procedures. The esterifying agent (1f) is preferably an acid chloride of formula (1f) wherein $R^t$ is chlorine, or an acid anhydride of formula (1f) wherein $R^t$ is a group of formula (1g). When an acid chloride such as acrylic acid chloride or methacrylic acid chloride is used as esterifying agent (1f), the reaction may be conducted in a solventless system or in a solvent (e.g., methylene chloride, toluene, hexane, diethyl ether, tetrahydrofuran or acetonitrile) by adding alcohol compound (1c), acid chloride, and a base (e.g., triethylamine, pyridine or 4-dimethylaminopyridine) in sequence or at the same time, and optional cooling or heating. When an acid anhydride such as acrylic acid anhydride or methacrylic acid anhydride is used as esterifying agent (1f), the reaction may be conducted by adding alcohol compound (1c), acid anhydride, and a base (e.g., triethylamine, pyridine or 4-dimethylaminopyridine) to a solvent (e.g., toluene or hexane) in sequence or at the same time, and optional cooling or heating.

Examples of the monomer having formula (1) are shown below, but not limited thereto. Herein $R^1$ is as defined above.

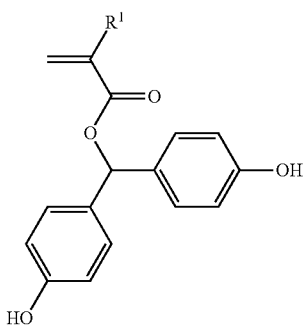

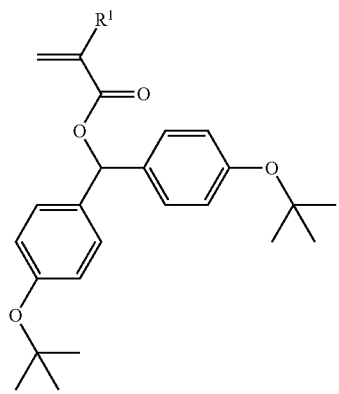

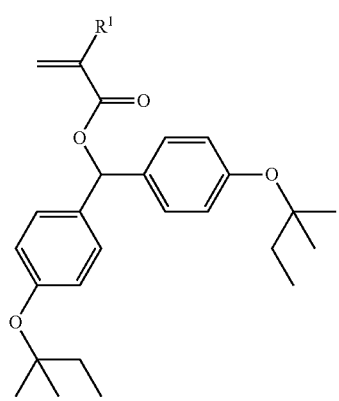

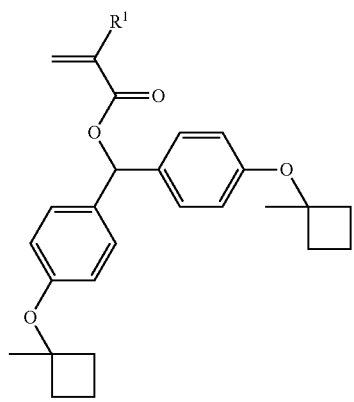

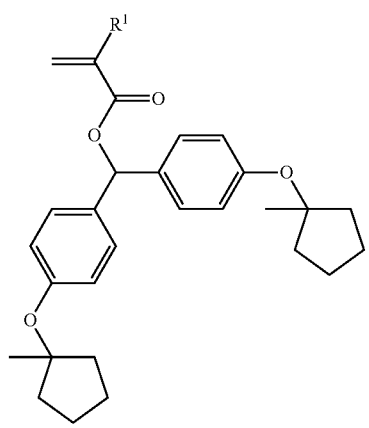

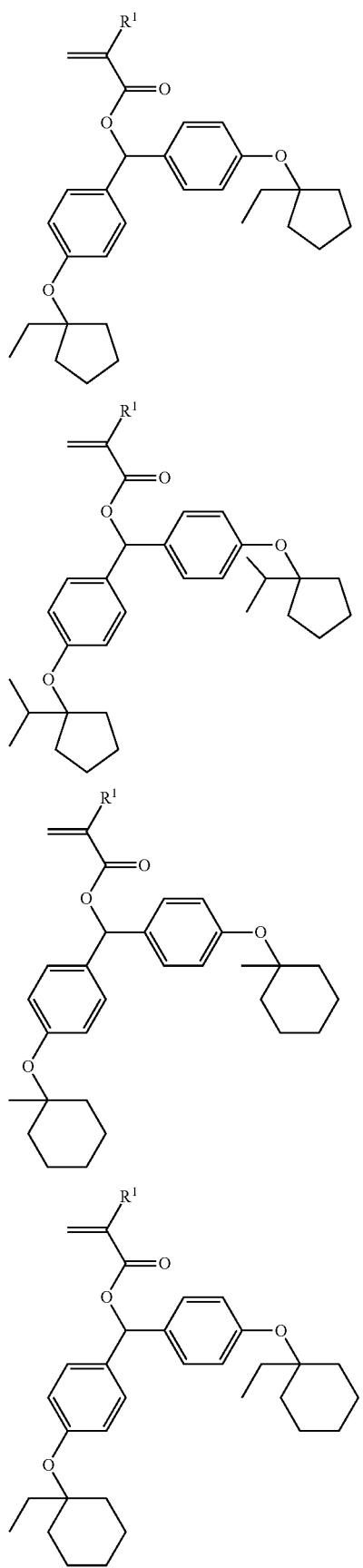
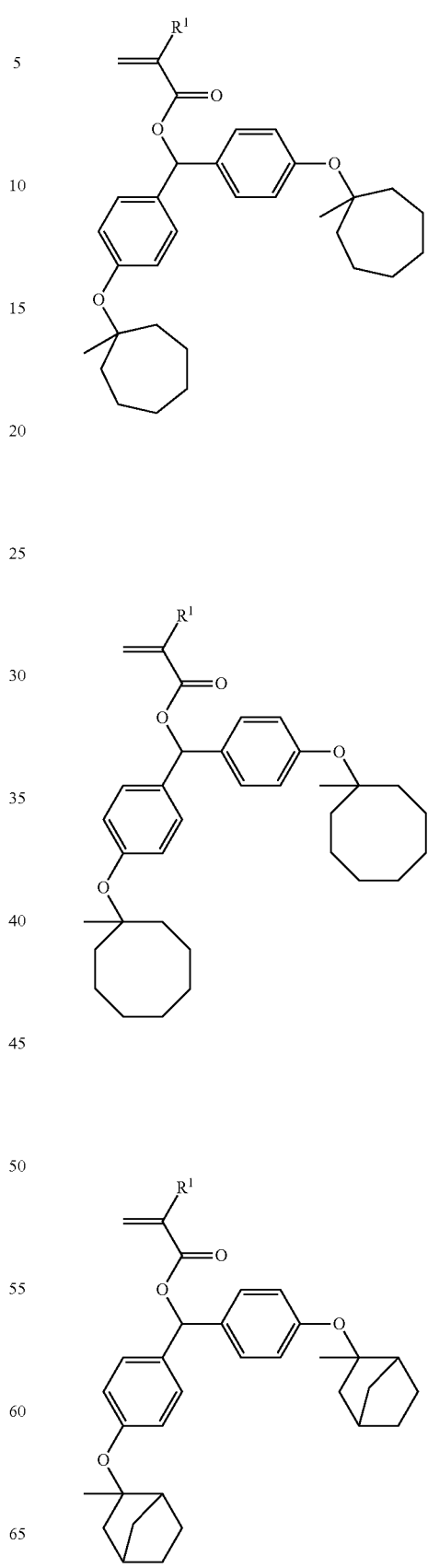

-continued
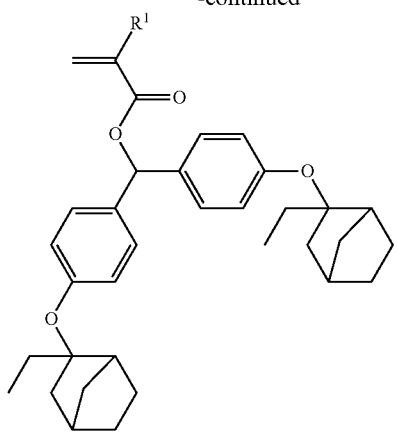
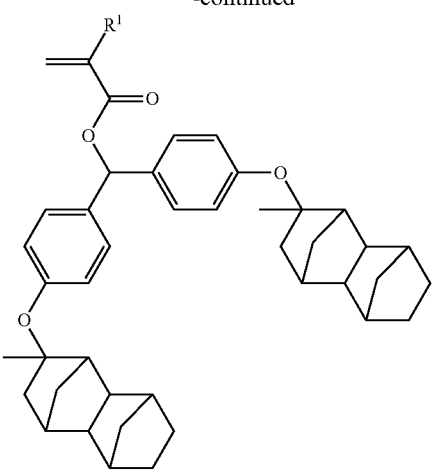
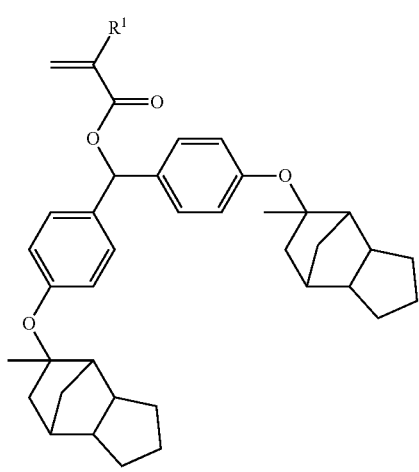
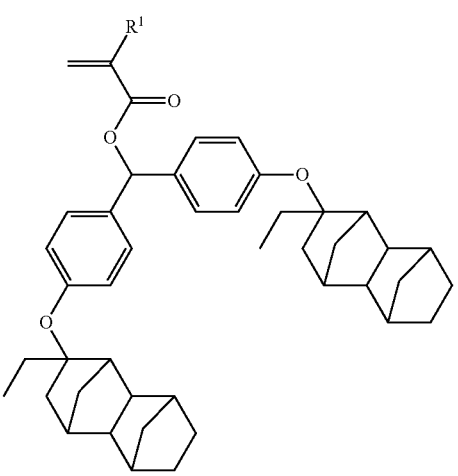
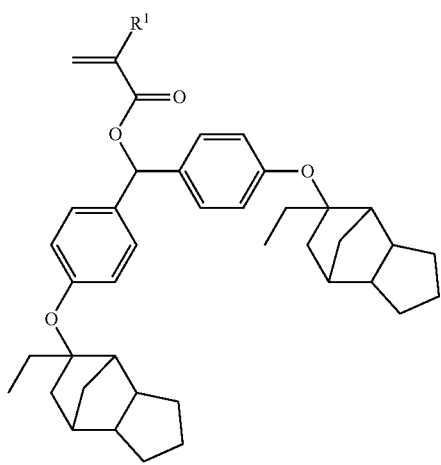
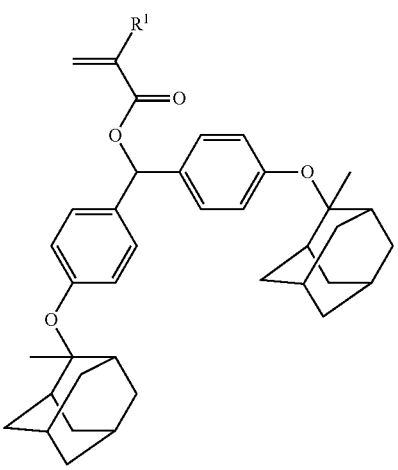

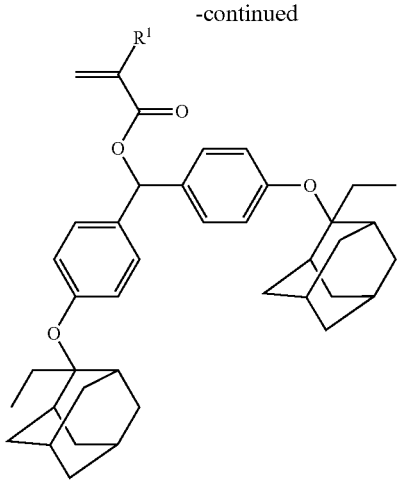
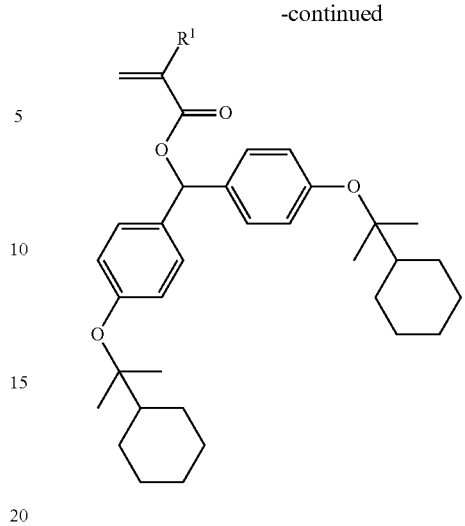
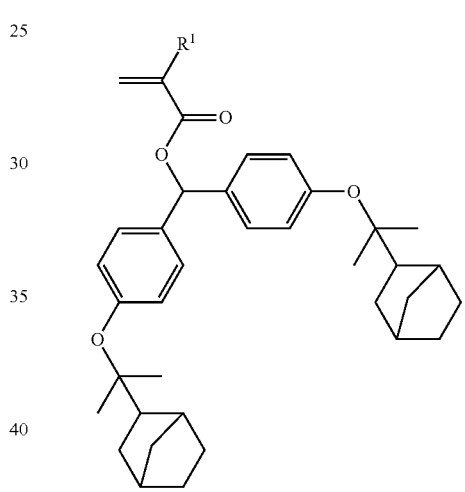
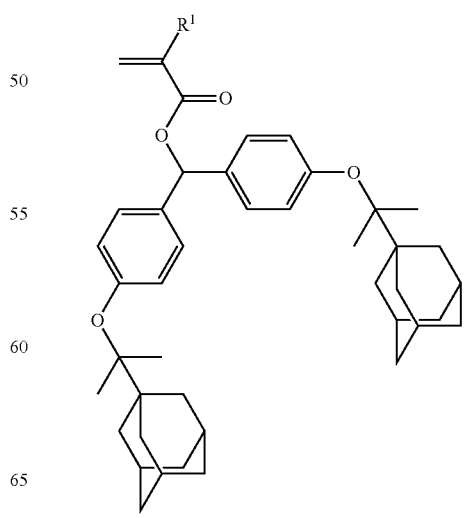

-continued
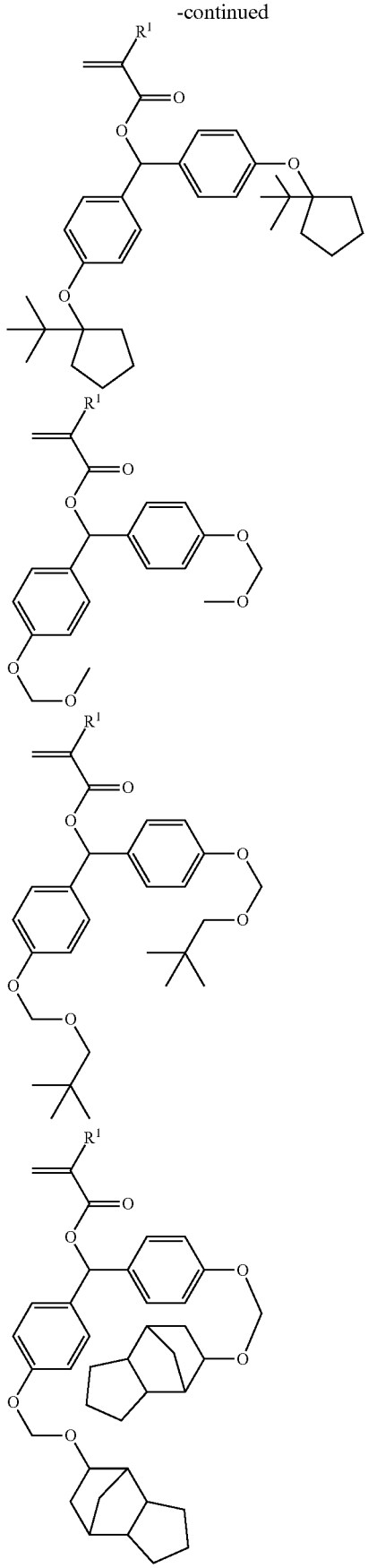
-continued
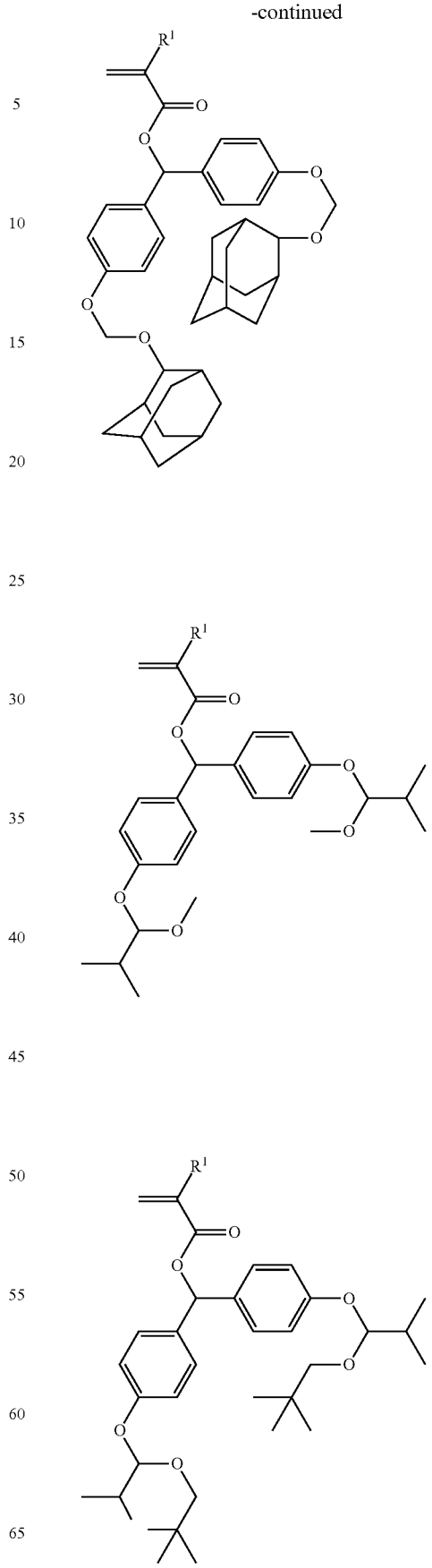

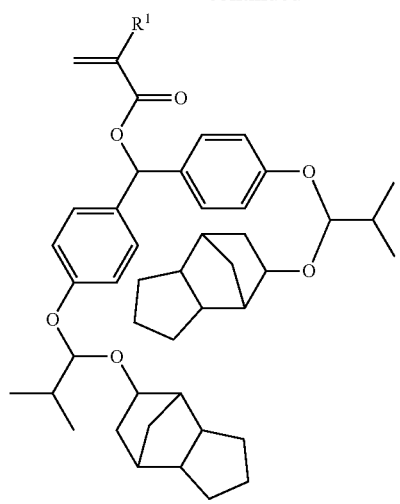
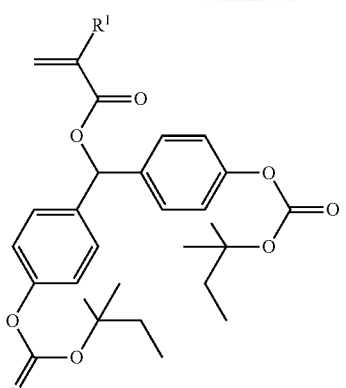
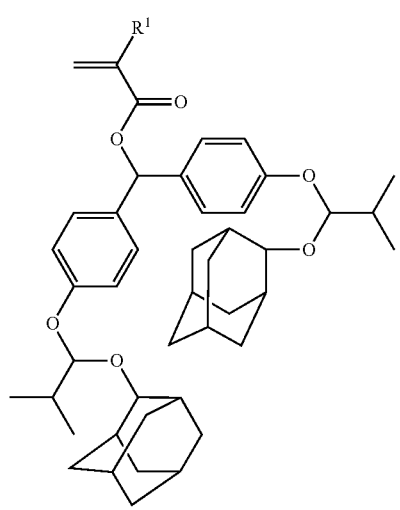
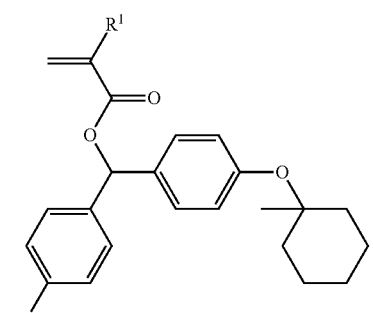
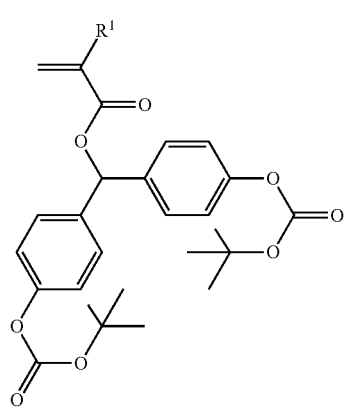
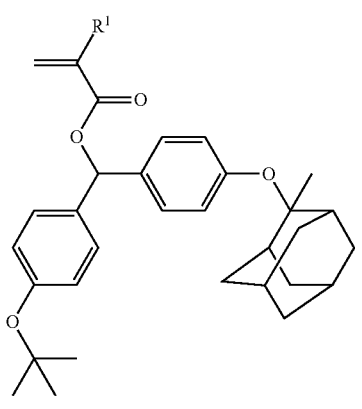

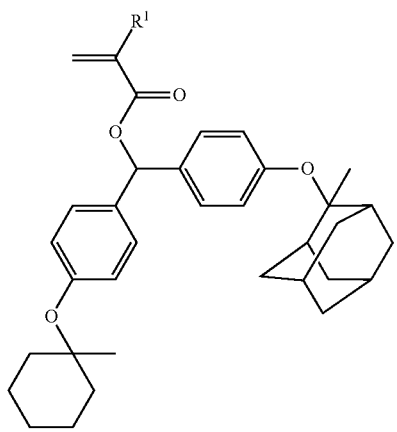
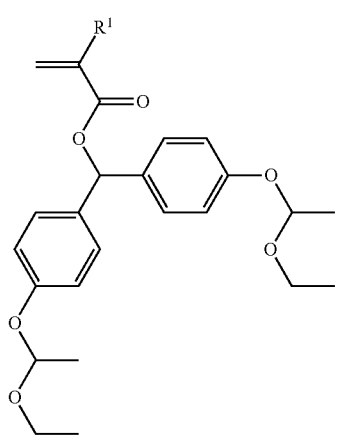
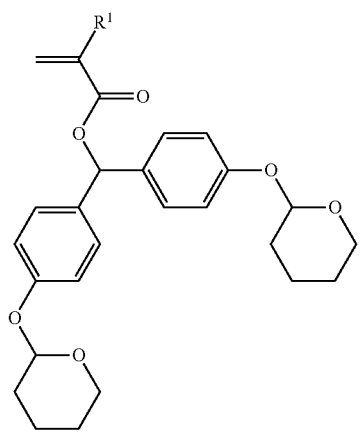
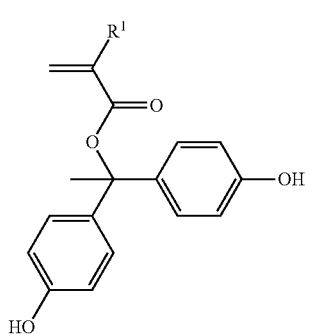
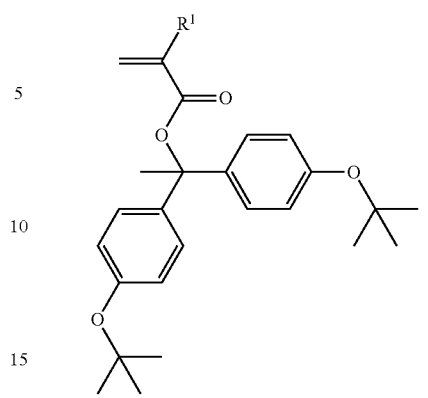
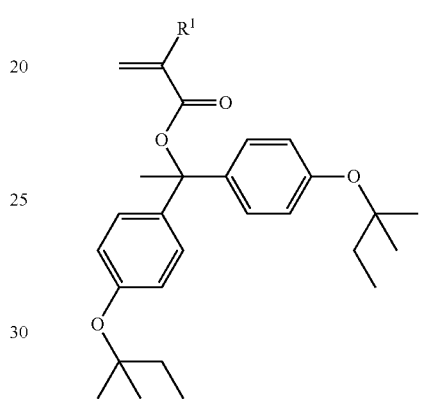
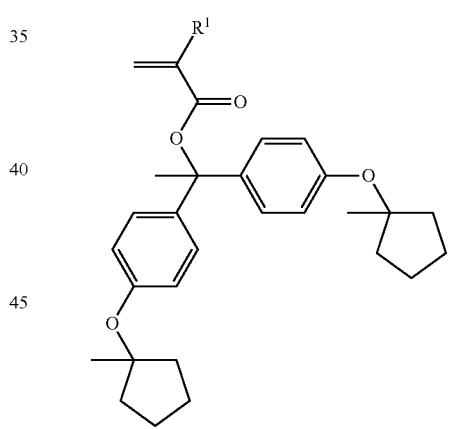
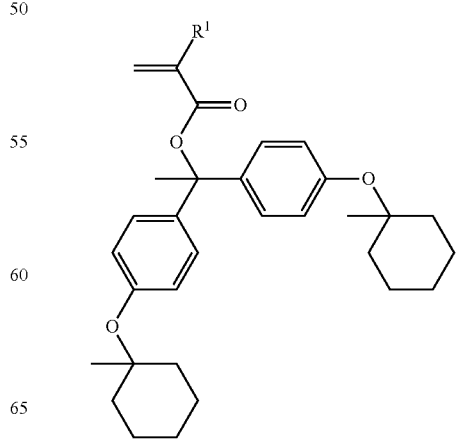

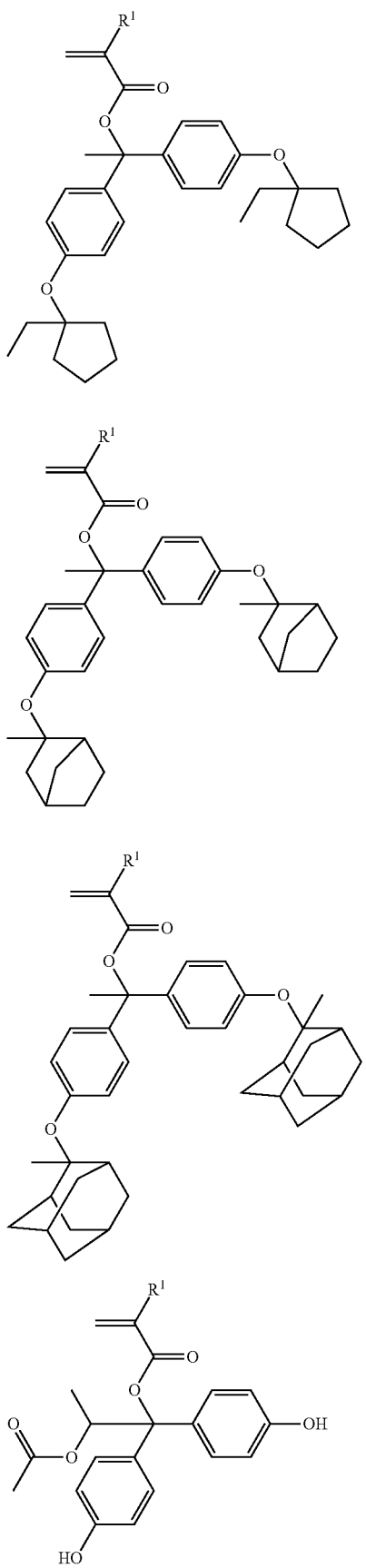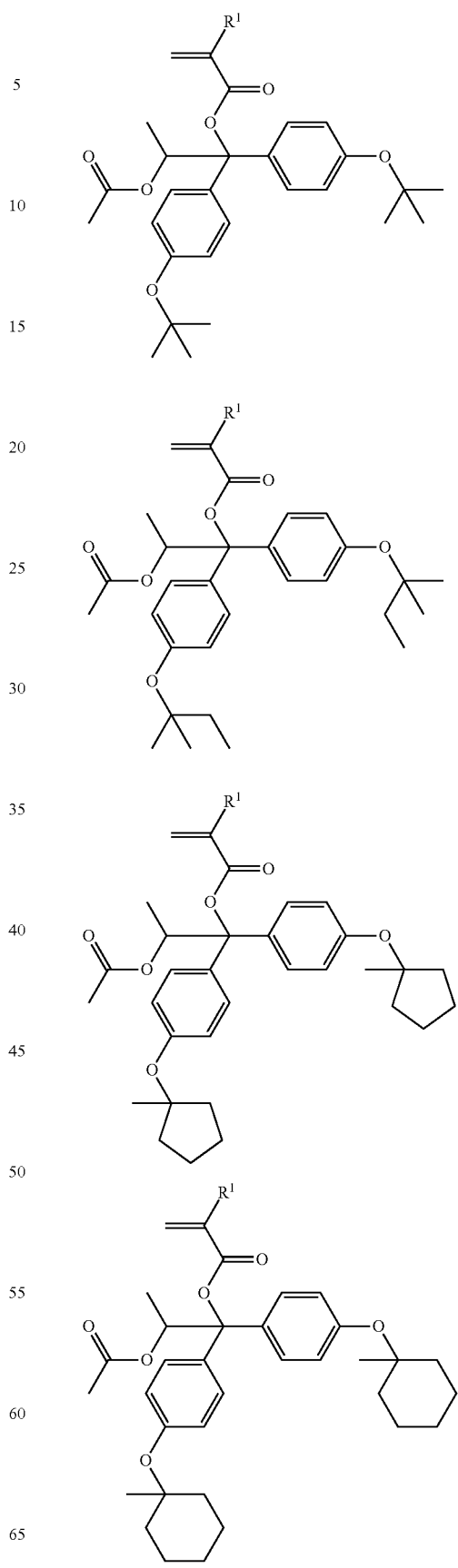

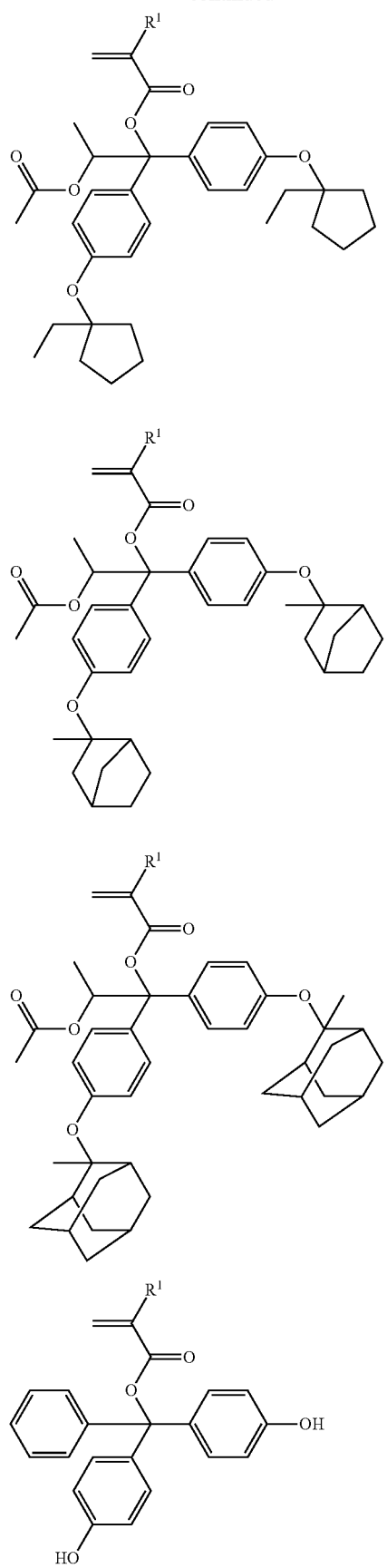

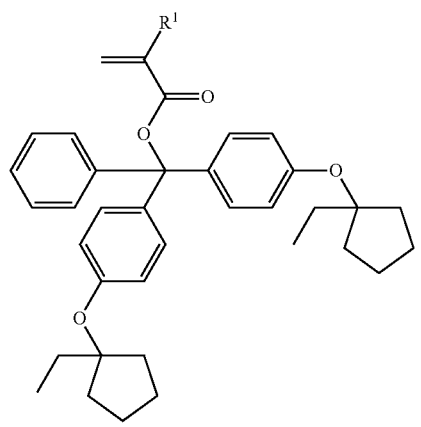
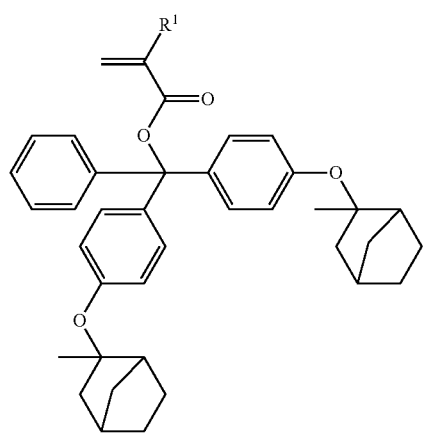
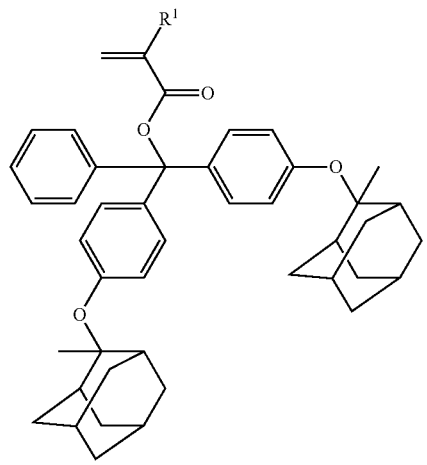
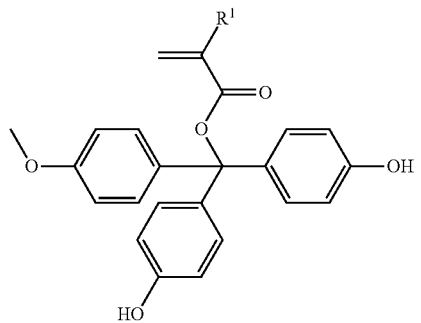
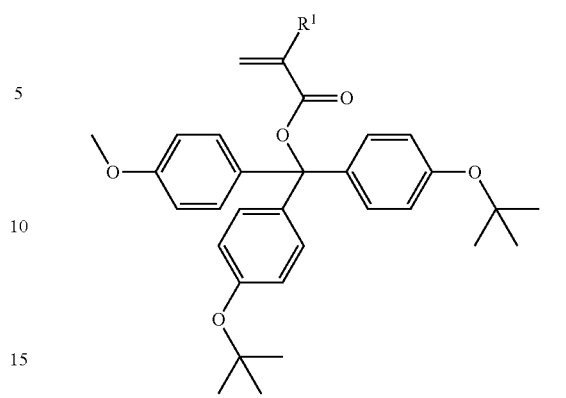
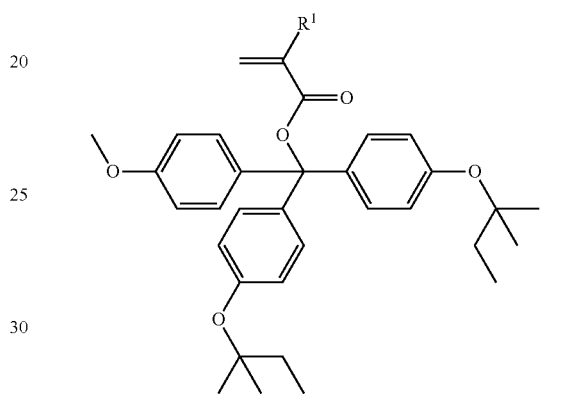
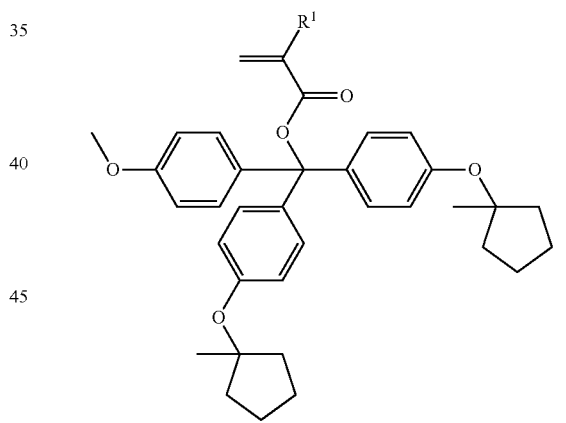
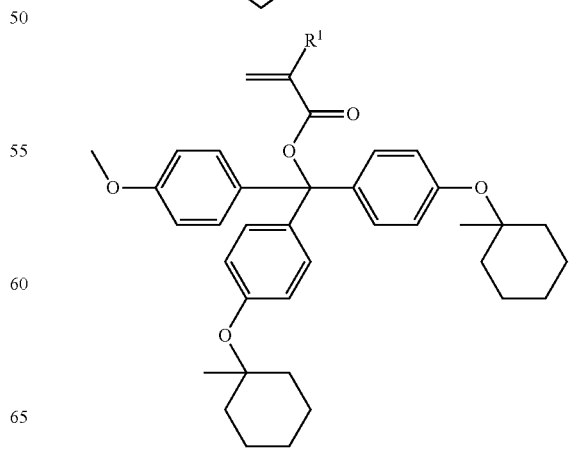

33
-continued
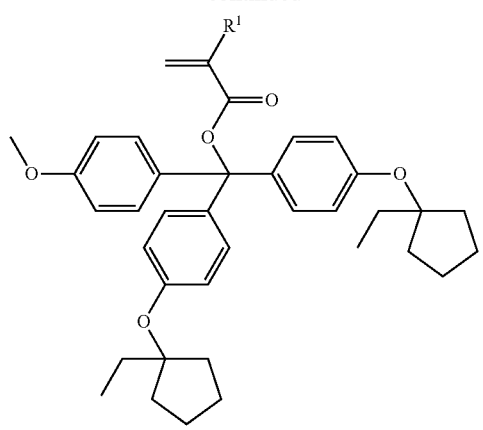
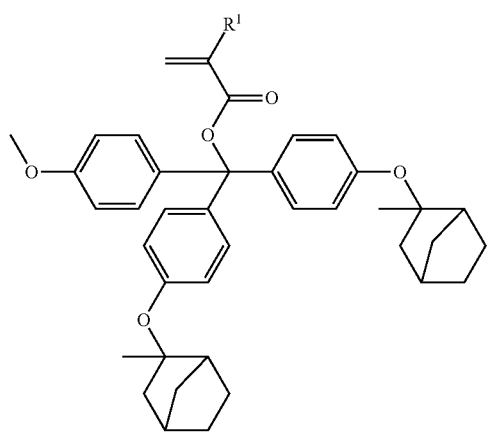
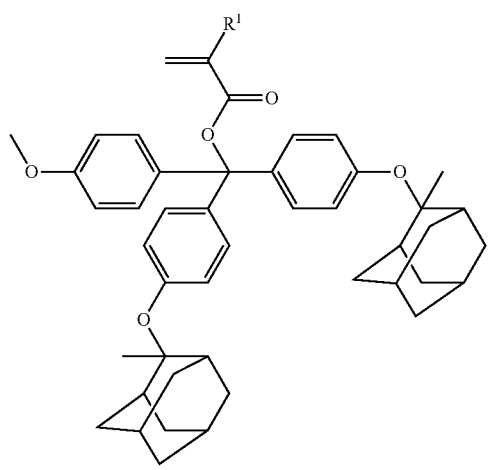
34
-continued
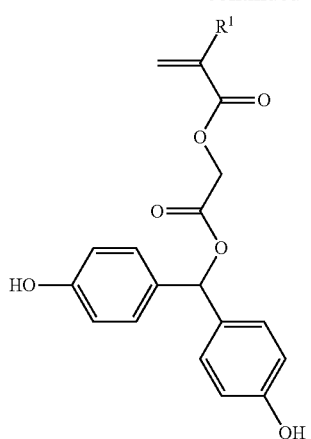
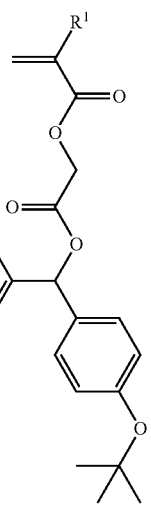
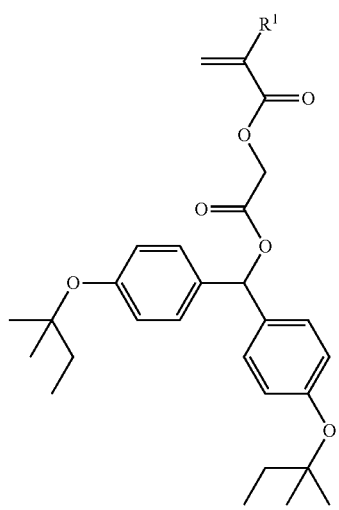

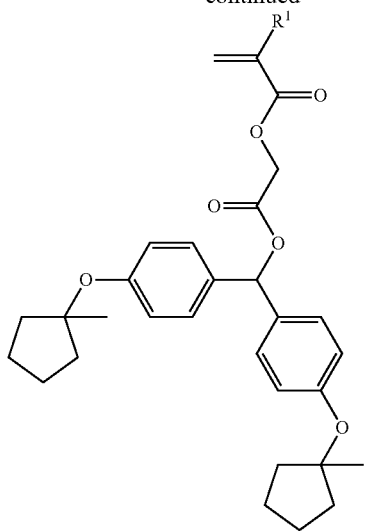
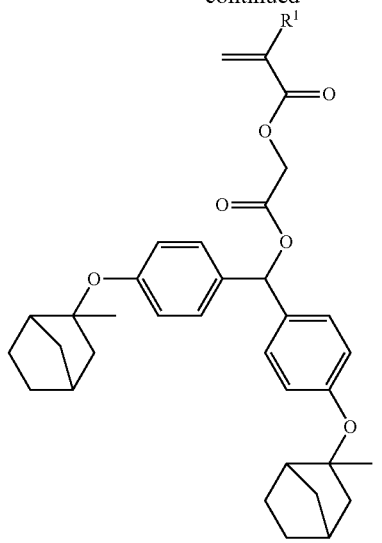
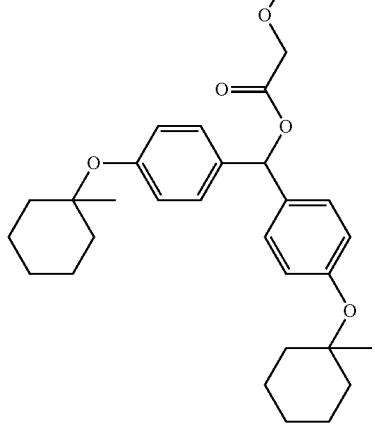
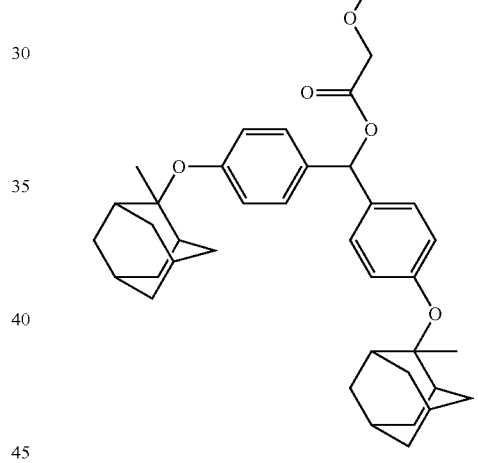
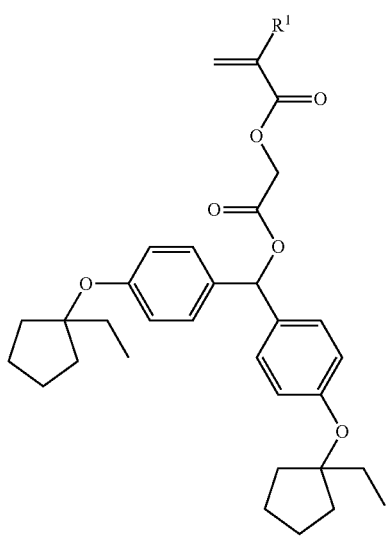
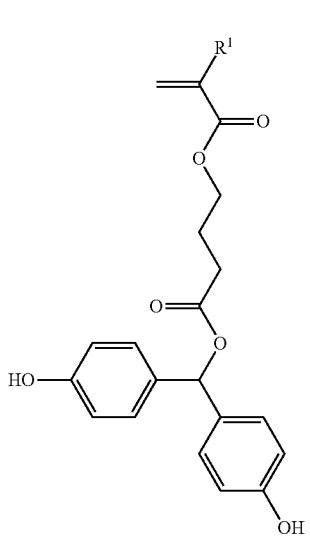

37
-continued
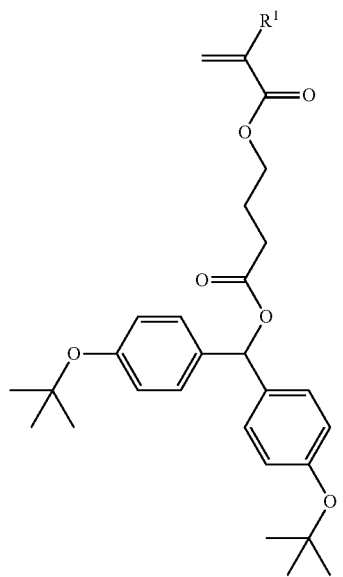
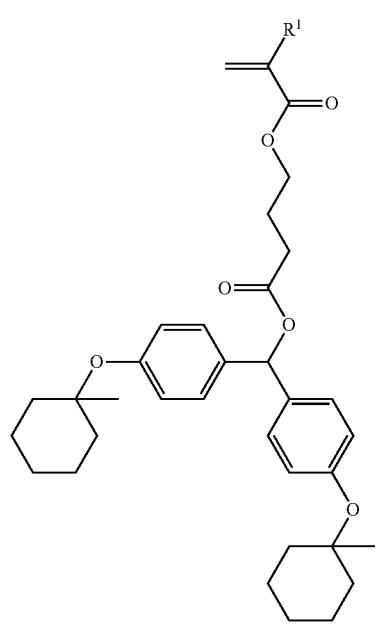
38
-continued
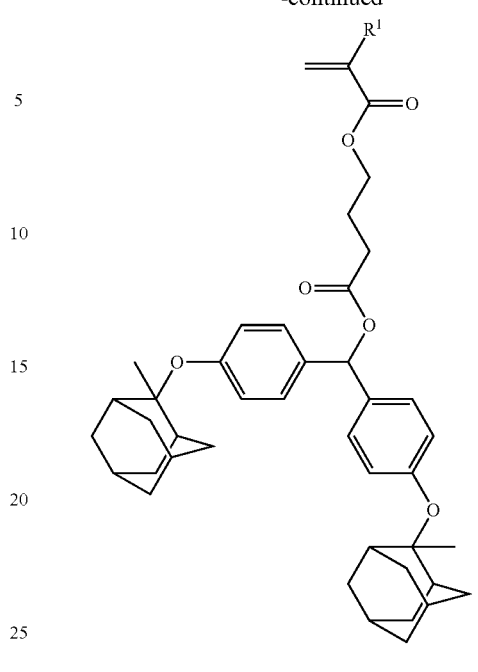
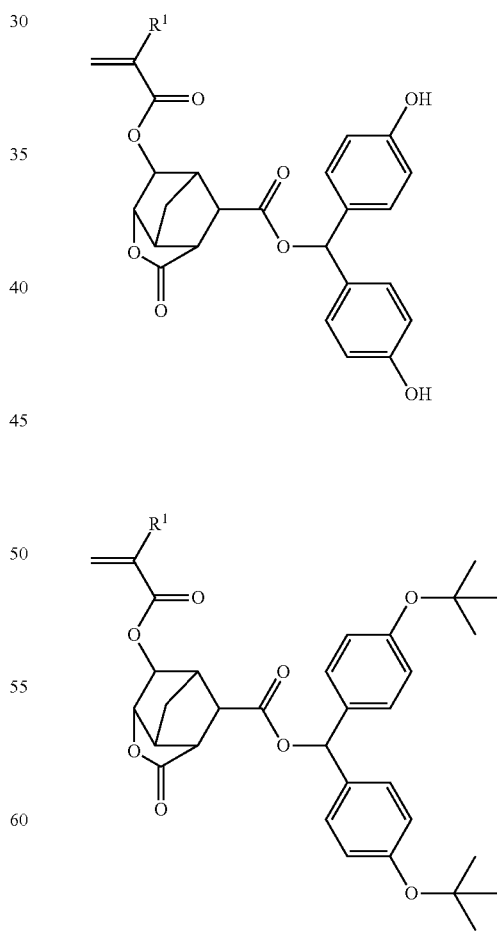

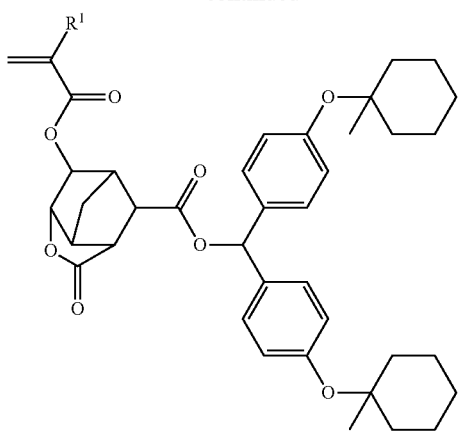
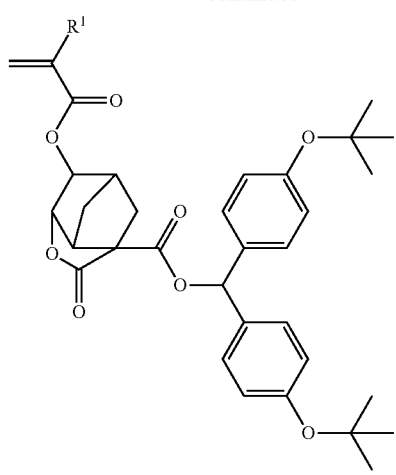
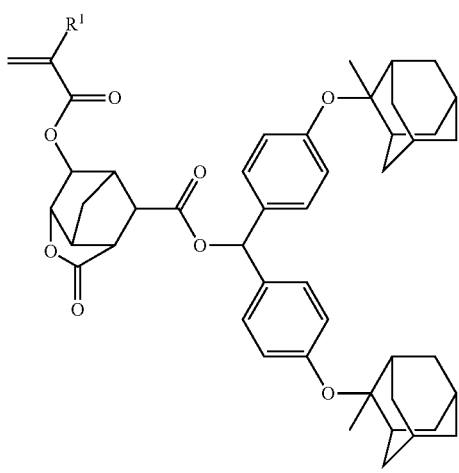
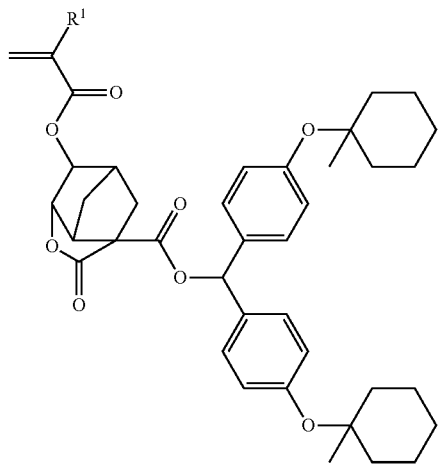
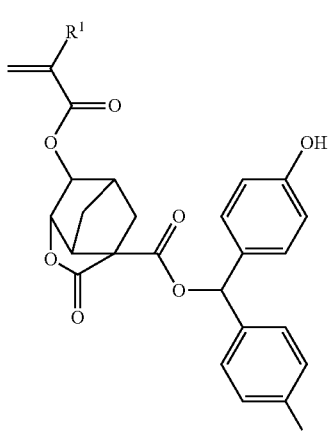
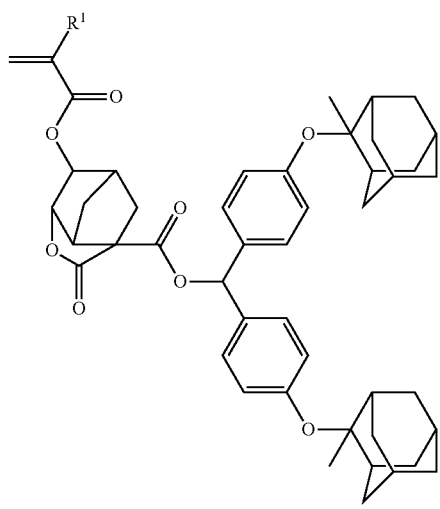

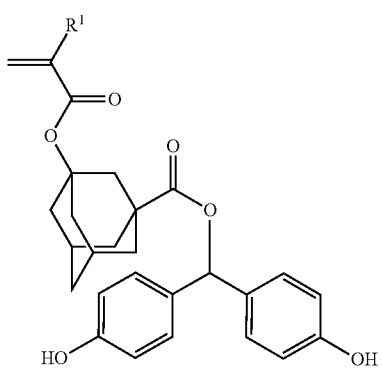
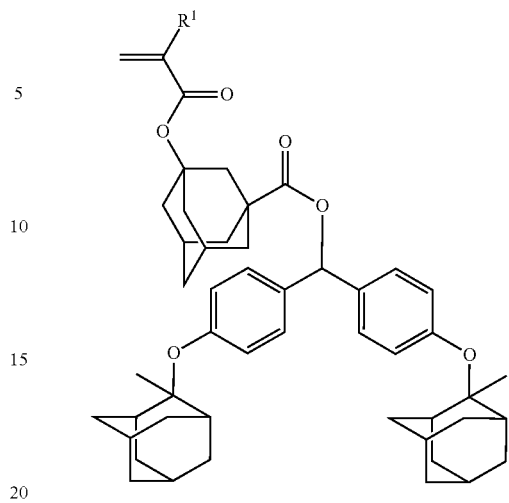
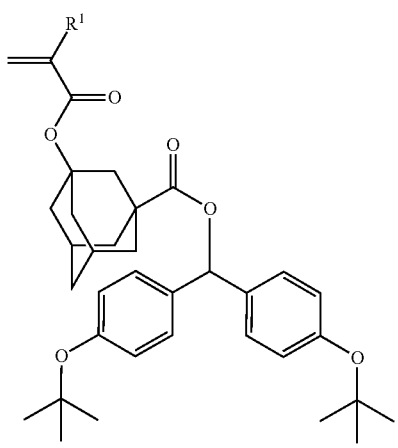
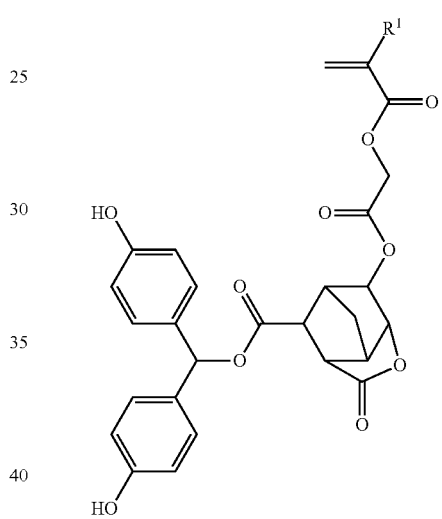
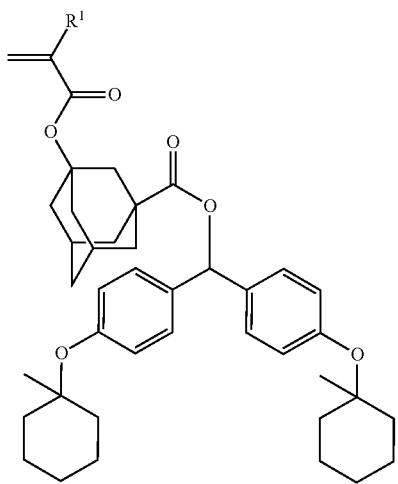
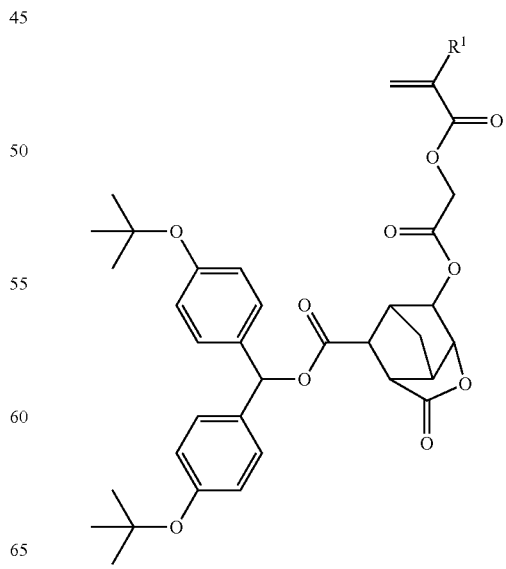

43
-continued
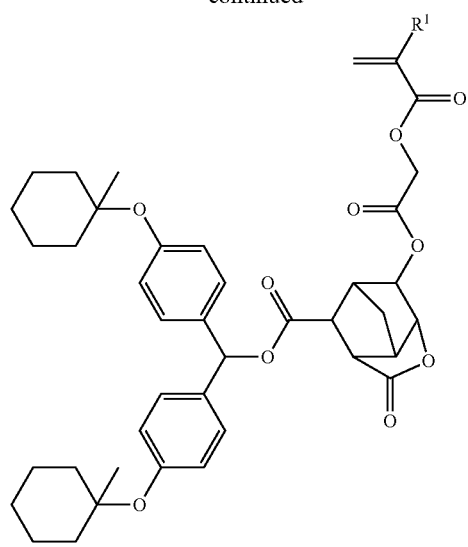
44
-continued
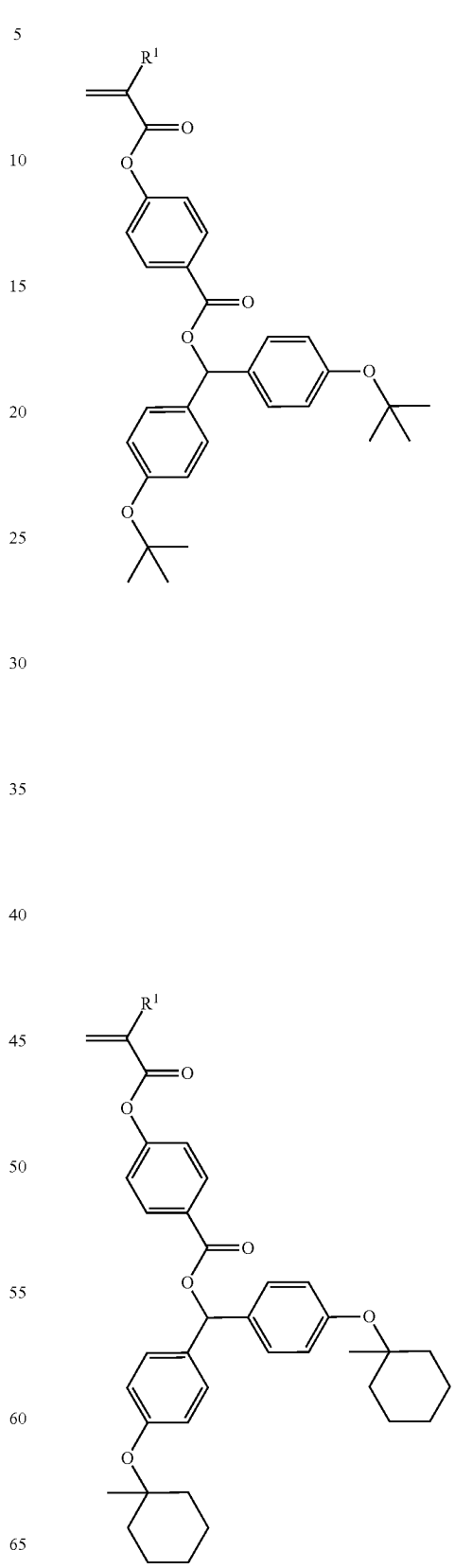

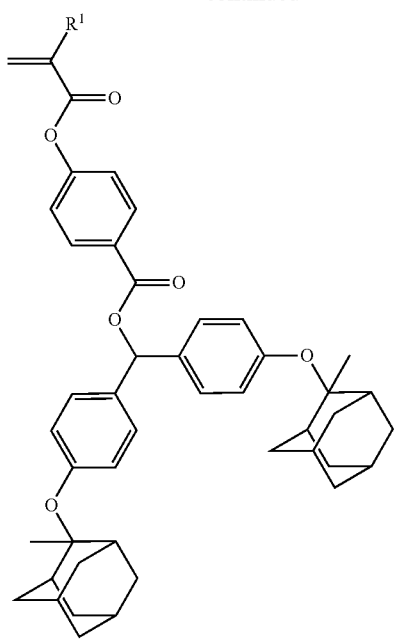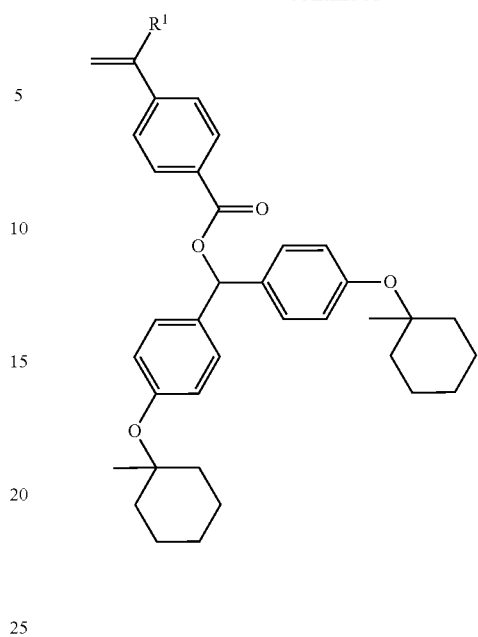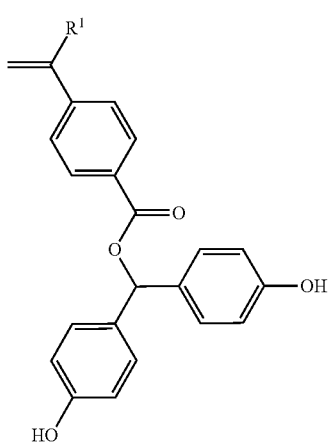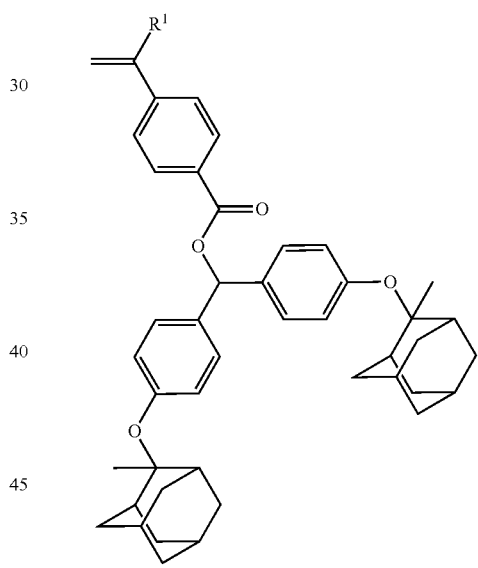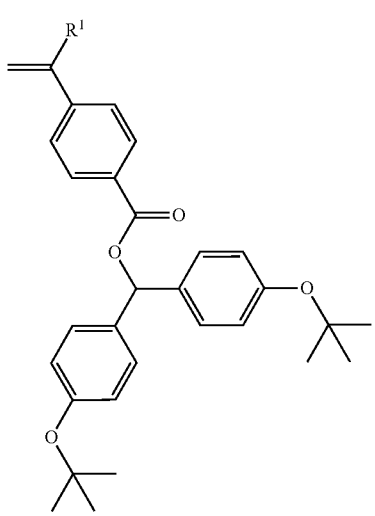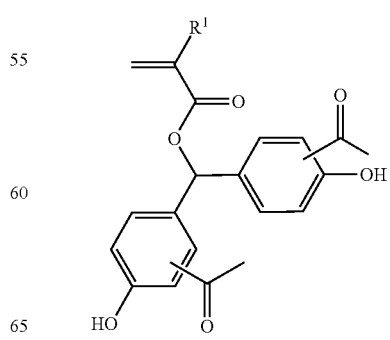

-continued
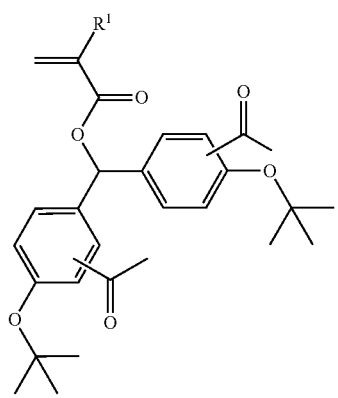
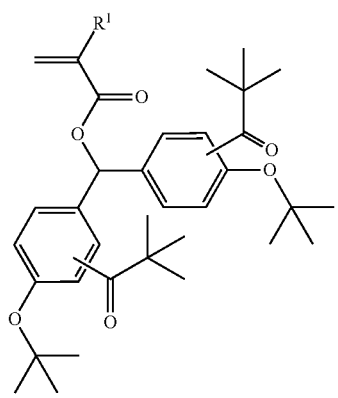
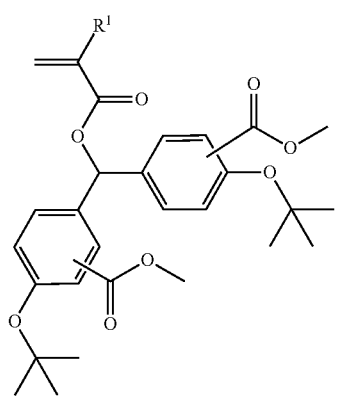
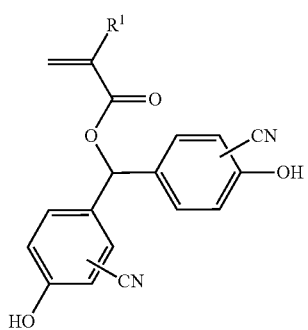
-continued
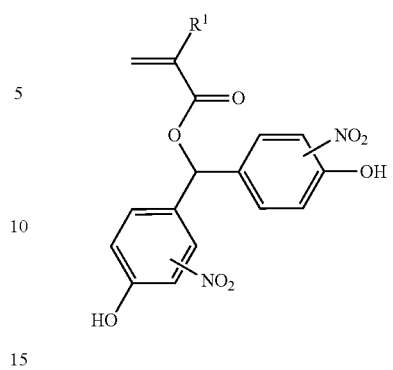
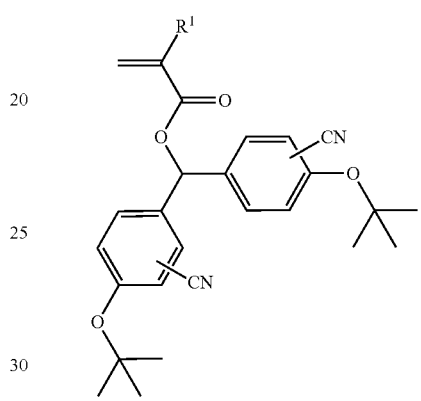
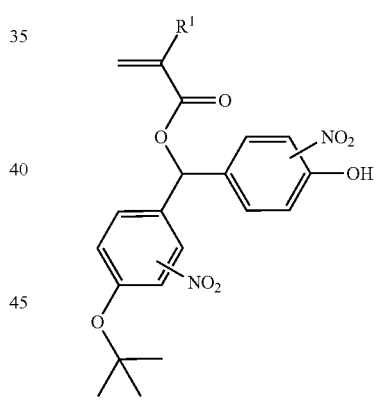
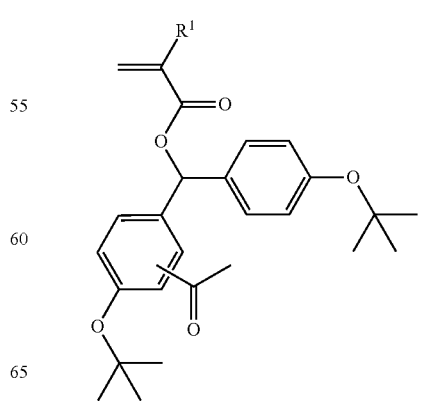

-continued

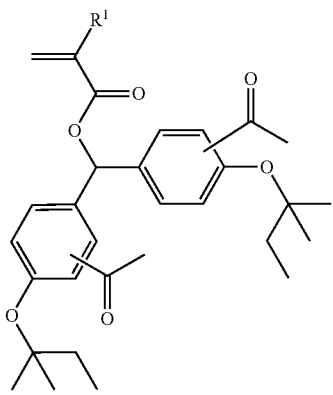

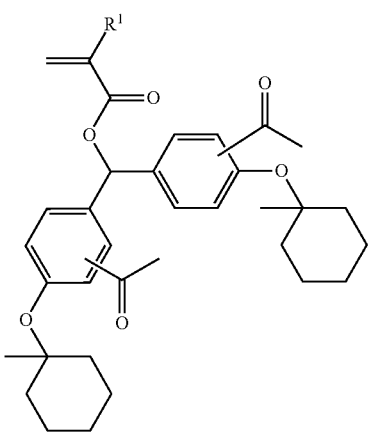

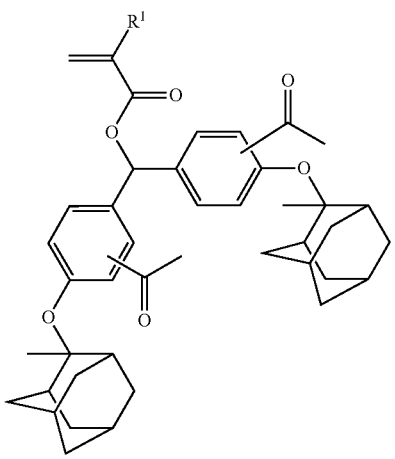

Polymer

A second embodiment of the invention is a polymer comprising recurring units derived from the monomer having formula (1), that is, recurring units (a) having the formula (A).

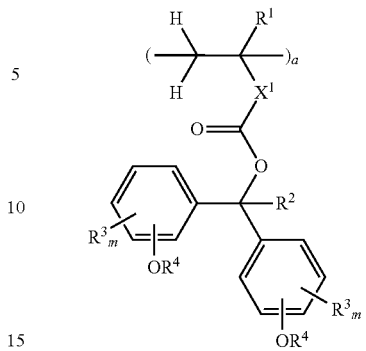

Herein $R^1$ to $R^4$, $X^1$ and m are as defined above, and a is a positive number in the range: $0<a\leq1.0$.

While the polymer contains recurring units having formula (A), the recurring units may be either of one type or of at least two types containing different acid labile groups.

In formulae (1) and (A), the acid labile group represented by $R^4$ may be selected from a variety of such groups. Suitable acid labile groups include groups of the following formulae (A-1) to (A-3).

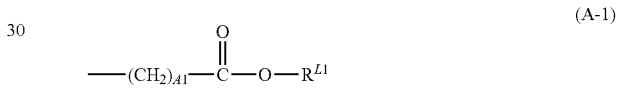

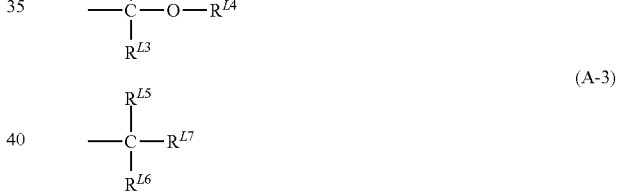

In formula (A-1), $R^{L1}$ is a tertiary alkyl group of 4 to 20 carbon atoms, preferably 4 to 15 carbon atoms, trialkylsilyl group of 1 to 6 carbon atoms, oxoalkyl group of 4 to 20 carbon atoms, or a group of formula (A-3). Suitable tertiary alkyl groups include t-butyl, t-pentyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Suitable trialkylsilyl groups include trimethylsilyl, triethylsilyl, and dimethyl-t-butylsilyl. Suitable oxoalkyl groups include 3-oxocyclohexyl, 4-methyl-2-oxooxan-4-yl, and 5-methyl-2-oxooxolan-5-yl. A1 is an integer of 0 to 6.

Examples of the acid labile group having formula (A-1) include t-butoxycarbonyl, t-butoxycarbonylmethyl, t-pentyloxycarbonyl, t-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Also preferred are those groups having the following formulae (A-1)-1 to (A-1)-10.

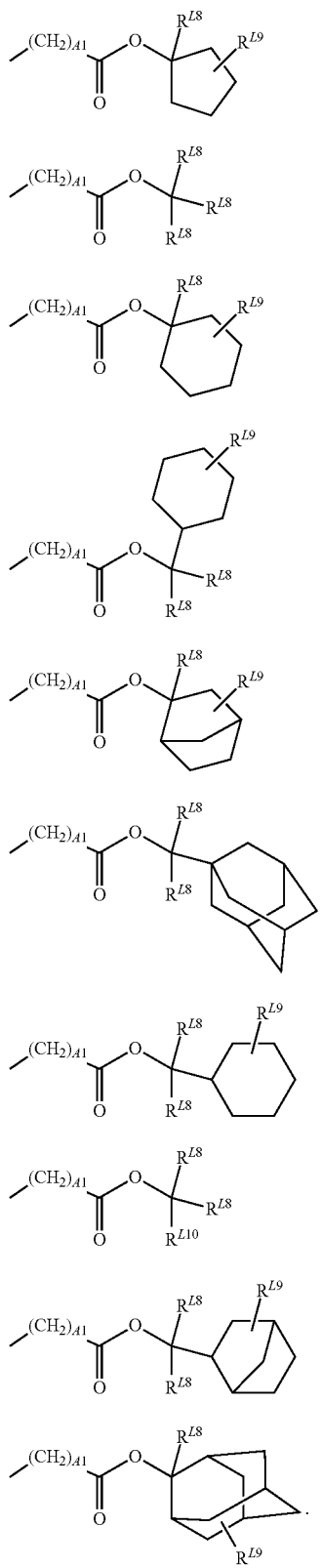

In the above formulae, $R^{L8}$ is each independently a straight, branched or cyclic $C_1$-$C_{10}$ alkyl group or a $C_6$-$C_{20}$ aryl group. $R^{L9}$ is hydrogen or a straight, branched or cyclic $C_1$-$C_{10}$ alkyl group. $R^{L10}$ is a straight, branched or cyclic $C_2$-$C_{10}$ alkyl group or a $C_6$-$C_{20}$ aryl group. A1 is an integer of 0 to 6.

In formula (A-2), $R^{L2}$ and $R^{L3}$ are each independently hydrogen or a straight, branched or cyclic alkyl group of 1 to 18 carbon atoms, preferably 1 to 10 carbon atoms. Suitable alkyl groups include methyl, ethyl, propyl, isopropyl, n-butyl, s-butyl, t-butyl, cyclopentyl, cyclohexyl, 2-ethylhexyl, and n-octyl. $R^{L4}$ is a monovalent hydrocarbon group of 1 to 18 carbon atoms, preferably 1 to 10 carbon atoms, which may contain a heteroatom such as oxygen. Suitable monovalent hydrocarbon groups include straight, branched or cyclic alkyl groups and substituted forms of these alkyl groups in which some hydrogen atoms are substituted by hydroxyl, alkoxy, oxo, amino, or alkylamino groups. Examples of the substituted alkyl groups are shown below.

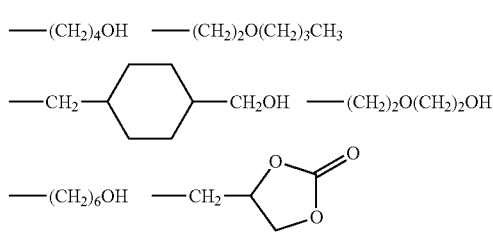

A pair of $R^{L2}$ and $R^{L3}$, $R^{L2}$ and $R^{L4}$, or $R^{L3}$ and $R^{L4}$ may bond together to form a ring with the carbon atom to which they are attached. In this event, each of ring-forming $R^{L2}$ and $R^{L3}$, $R^{L2}$ and $R^{L4}$, or $R^{L3}$ and $R^{L4}$ is a straight or branched alkylene group of 1 to 18 carbon atoms, preferably 1 to 10 carbon atoms while the carbon count of the ring preferably ranges from 3 to 10, more preferably from 4 to 10.

Of the acid labile groups of formula (A-2), the straight and branched ones are exemplified by the following groups having formulae (A-2)-1 to (A-2)-69.

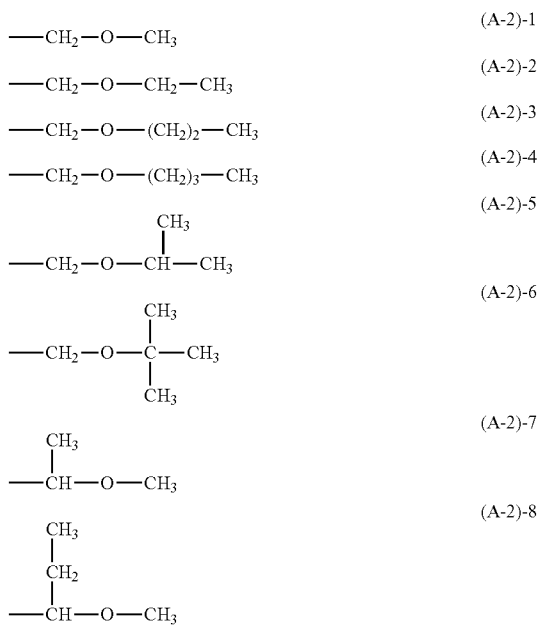

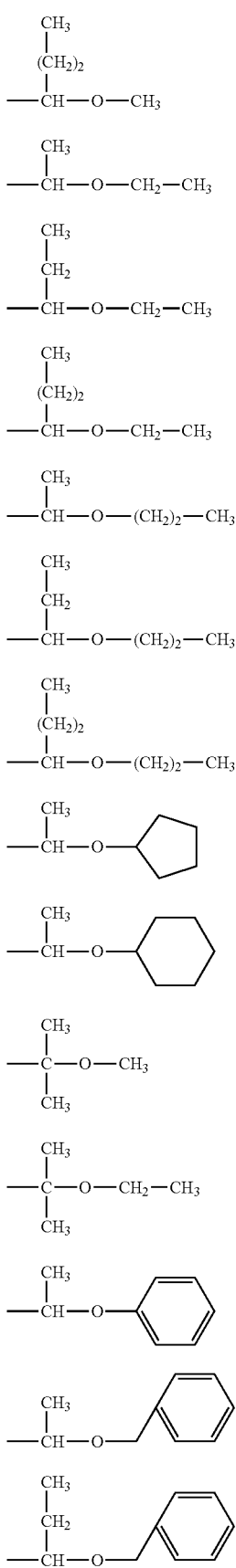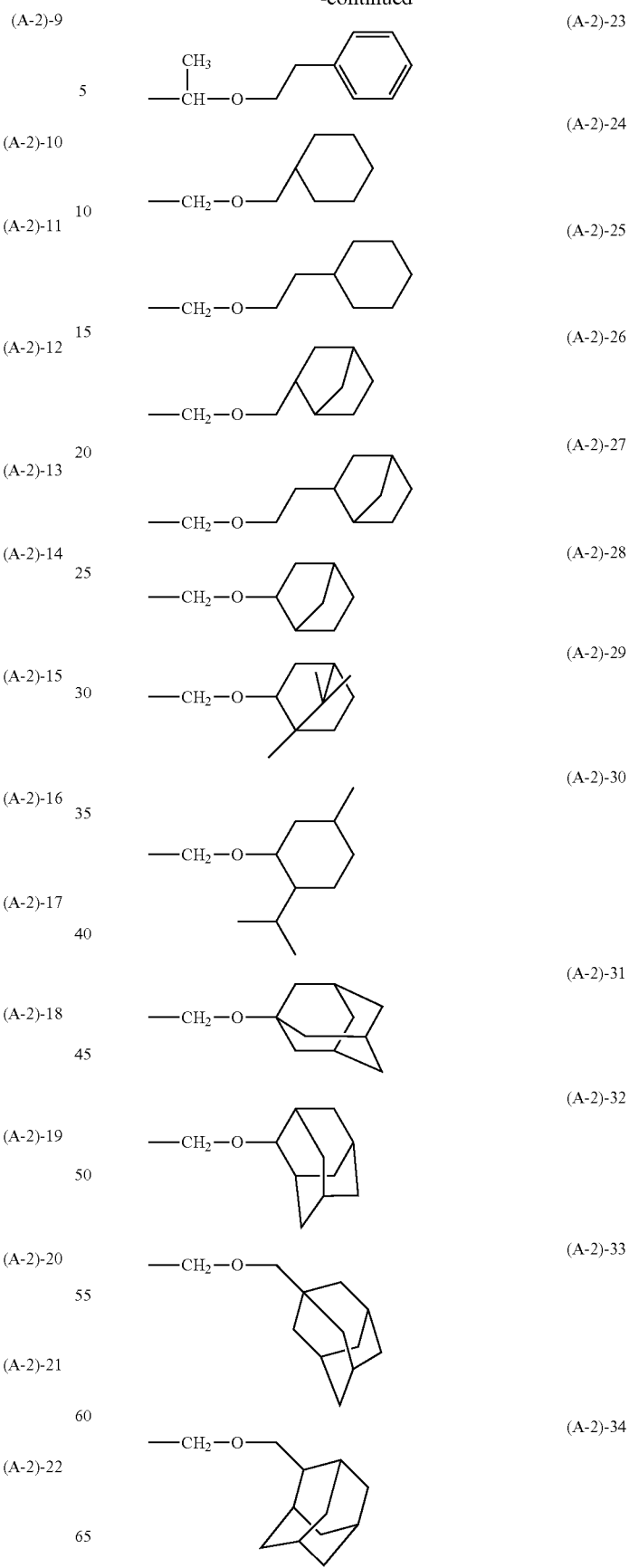

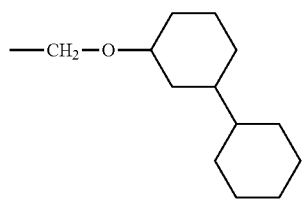 (A-2)-35
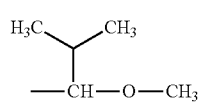 (A-2)-36
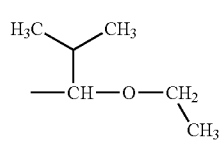 (A-2)-37
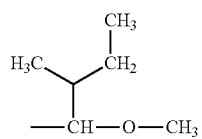 (A-2)-38
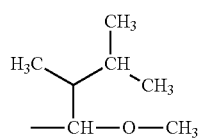 (A-2)-39
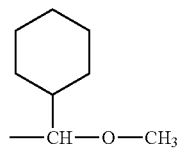 (A-2)-40
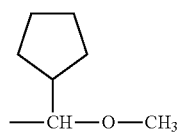 (A-2)-41
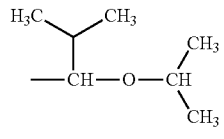 (A-2)-42
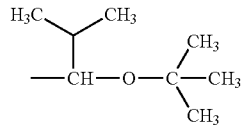 (A-2)-43
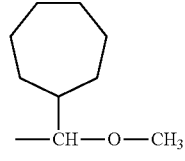 (A-2)-44
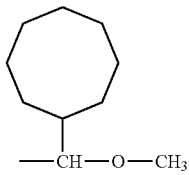 (A-2)-45
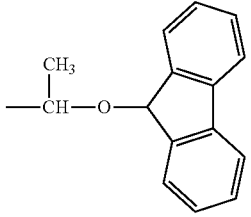 (A-2)-46
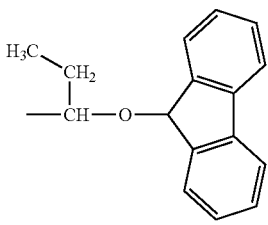 (A-2)-47
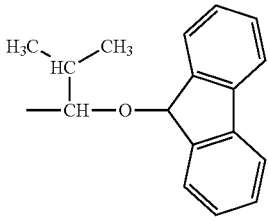 (A-2)-48
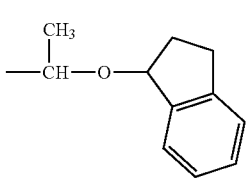 (A-2)-49
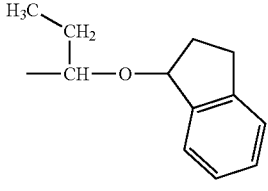 (A-2)-50
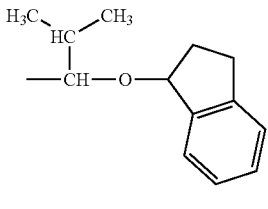 (A-2)-51
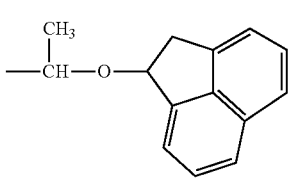 (A-2)-52

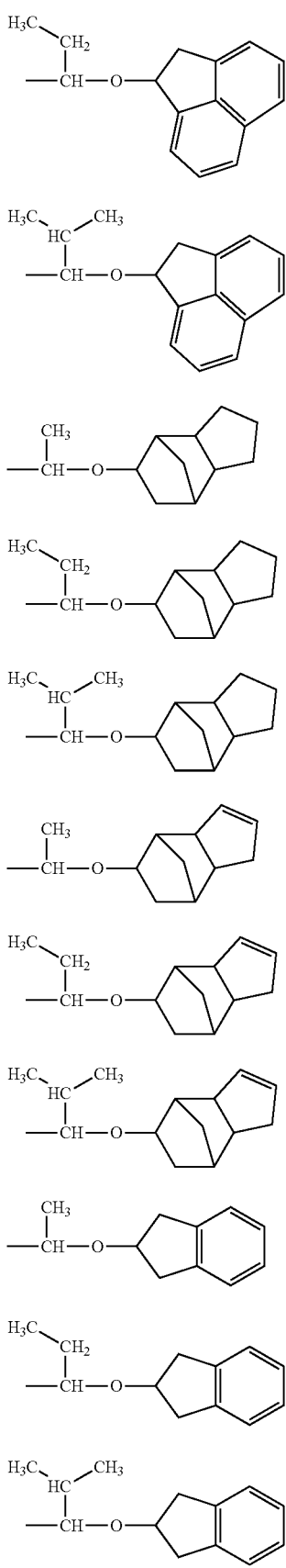
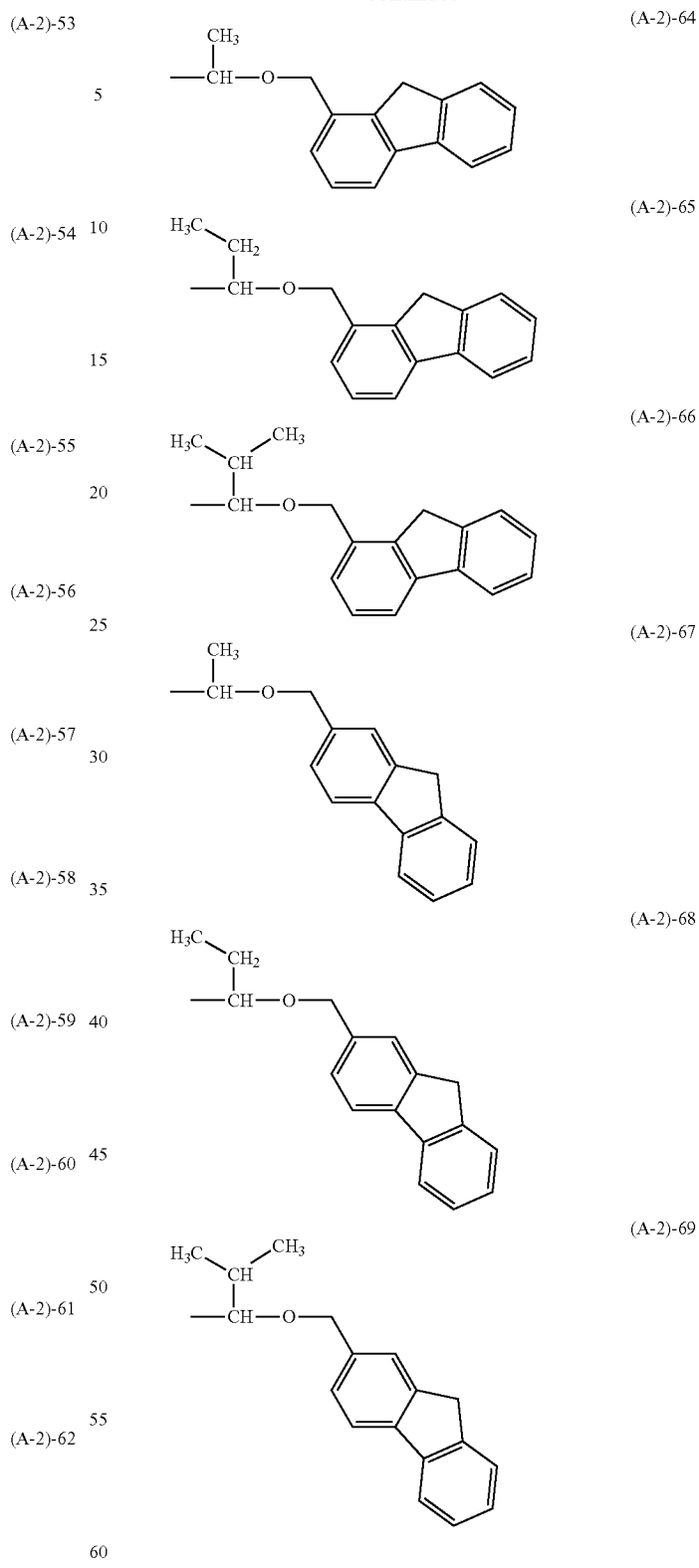
Of the acid labile groups of formula (A-2), the cyclic ones are, for example, tetrahydrofuran-2-yl, 2-methyltetrahydrofuran-2-yl, tetrahydropyran-2-yl, and 2-methyltetrahydropyran-2-yl.
Other examples of acid labile groups include those of the following formula (A-2a) or (A-2b) while the polymer may be crosslinked within the molecule or between molecules with these acid labile groups.

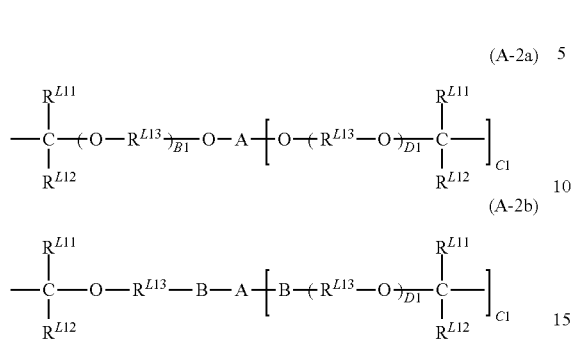

Herein $R^{L11}$ and $R^{L12}$ each are hydrogen or a straight, branched or cyclic $C_1$-$C_8$ alkyl group. $R^{L11}$ and $R^{L12}$ may bond together to form a ring with the carbon atom to which they are attached, and a ring-forming combination of $R^{L40}$ and $R^{L41}$ is a straight or branched $C_1$-$C_8$ alkylene group. $R^{L13}$ is a straight, branched or cyclic $C_1$-$C_{10}$ alkylene group. "A" is a (C1+1)-valent aliphatic or alicyclic saturated hydrocarbon group, aromatic hydrocarbon group or heterocyclic group having 1 to 50 carbon atoms, which may be separated by a heteroatom or in which a carbon-bonded hydrogen atom may be substituted by hydroxyl, carboxyl, acyl moiety or fluorine atom. "B" is —CO—O—, —NHCO—O— or —NHCONH—. Each of B1 and D1 is an integer of 0 to 10, preferably an integer of 0 to 5, and C1 is an integer of 1 to 7, preferably 1 to 3.

Preferably, "A" is selected from divalent to tetravalent, straight, branched or cyclic $C_1$-$C_{20}$ alkylene, alkyltriyl and alkyltetrayl groups, and $C_6$-$C_{30}$ arylene groups, which may contain a heteroatom or in which a carbon-bonded hydrogen atom may be substituted by hydroxyl, carboxyl, acyl moiety or halogen atom.

The crosslinking acetal groups of formulae (A-2a) and (A-2b) are exemplified by the following formulae (A-2)-70 through (A-2)-77.

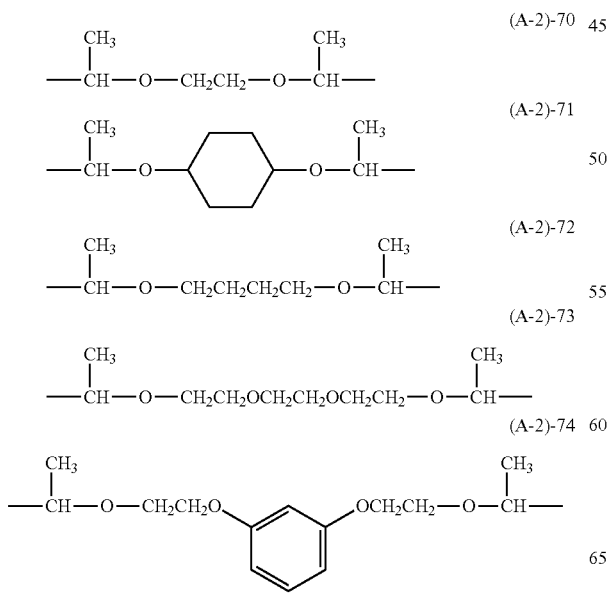

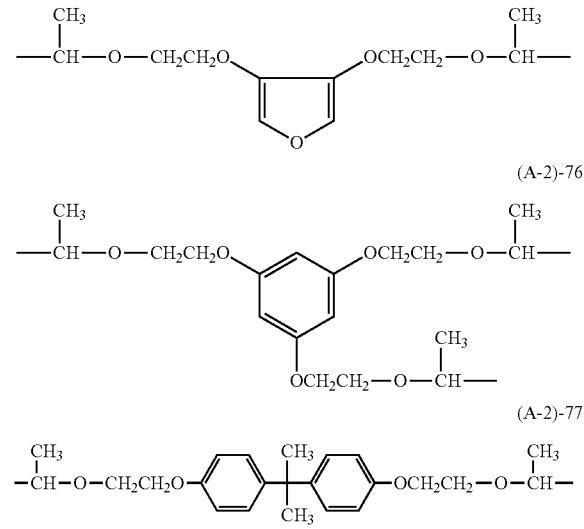

In formula (A-3), $R^{L5}$, $R^{L6}$ and $R^{L7}$ each are a monovalent hydrocarbon group, typically a straight, branched or cyclic $C_1$-$C_{20}$ alkyl group, which may contain a heteroatom such as oxygen, sulfur, nitrogen or fluorine. A pair of $R^{L5}$ and $R^{L6}$, $R^{L5}$ and $R^{L7}$, or $R^{L6}$ and $R^{L7}$ may bond together to form a ring with the carbon atom to which they are attached. In this event, each of ring-forming $R^{L5}$ and $R^{L6}$, $R^{L5}$ and $R^{L7}$, or $R^{L6}$ and $R^{L7}$ is a straight or branched alkylene group of 1 to 20 carbon atoms while the carbon count of the ring preferably ranges from 3 to 20.

Exemplary tertiary alkyl groups of formula (A-3) include t-butyl, triethylcarbyl, 1-ethylnorbornyl, 1-methylcyclohexyl, 1-ethylcyclopentyl, 2-(2-methyl)adamantyl, 2-(2-ethyl)adamantyl, and t-pentyl.

Other exemplary tertiary alkyl groups of formula (A-3) include those of the following formulae (A-3)-1 to (A-3)-18.

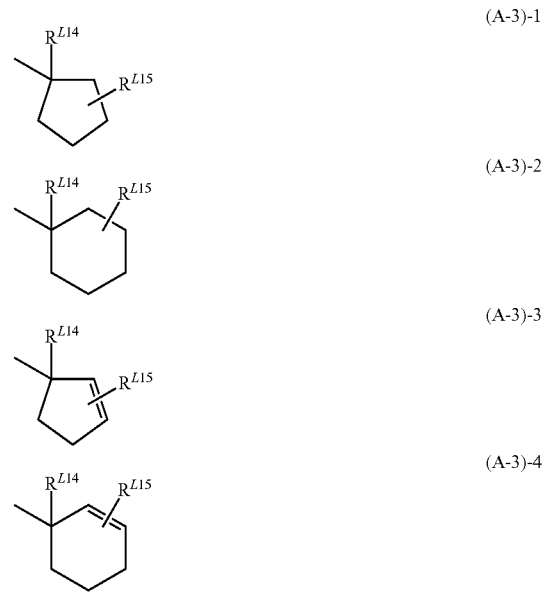

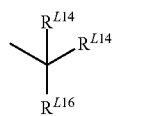 (A-3)-5

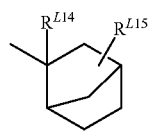 (A-3)-6

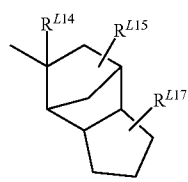 (A-3)-7

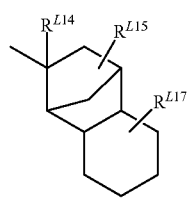 (A-3)-8

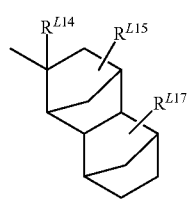 (A-3)-9

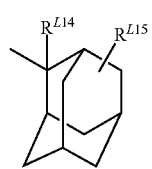 (A-3)-10

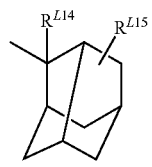 (A-3)-11

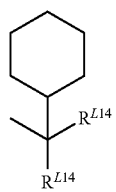 (A-3)-12

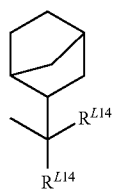 (A-3)-13

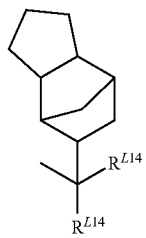 (A-3)-14

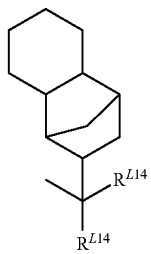 (A-3)-15

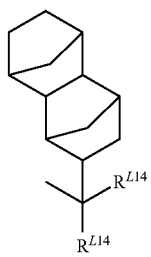 (A-3)-16

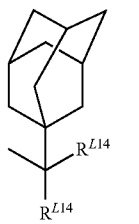 (A-3)-17

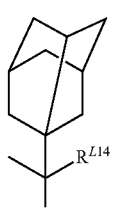 (A-3)-18

Herein $R^{L14}$ is each independently a straight, branched or cyclic $C_1$-$C_8$ alkyl group or $C_6$-$C_{20}$ aryl group, typically phenyl or naphthyl, $R^{L15}$ and $R^{L17}$ each are hydrogen or a straight, branched or cyclic $C_1$-$C_{20}$ alkyl group, and $R^{L16}$ is a $C_6$-$C_{20}$ aryl group, typically phenyl.

Other acid labile groups include those having the formulae (A-3)-19 and (A-3)-20. The polymer may be crosslinked within the molecule or between molecules with these acid labile groups.

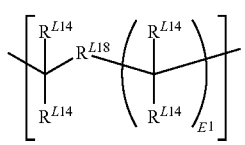
(A-3)-19

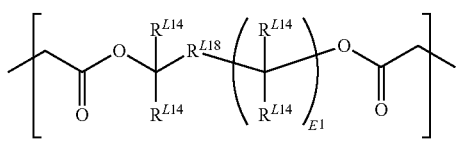
(A-3)-20

Herein $R^{L14}$ is as defined above, $R^{L18}$ is a straight, branched or cyclic $C_1$-$C_{20}$ di- to tetravalent aliphatic hydrocarbon group or $C_6$-$C_{20}$ di- to tetravalent aromatic hydrocarbon group, which may contain a heteroatom such as oxygen, sulfur or nitrogen, and E1 is an integer of 1 to 3.

The method of introducing the acid labile group $R^4$ in the recurring unit of formula (A) includes a method of introducing at the stage of the monomer having formula (1), or a method of polymerizing a monomer having a phenolic hydroxyl group into a polymer and introducing the acid labile group into the polymer. The introduction of the acid labile group at the monomer stage has the advantage of possible control of a minute amount of the acid labile group introduced. Also in a common practice, an acid labile group of tertiary alkyl type is introduced at the monomer stage, whereas an acid labile group of acetal type is introduced at the polymer stage.

In a preferred embodiment, the polymer comprising recurring units (a) of formula (A) further comprises recurring units (b) having an adhesive group selected from among hydroxyl, carboxyl, lactone ring, carbonate, thiocarbonate, carbonyl, cyclic acetal, ether, ester, sulfonic acid ester, cyano, amide, and —O—C(=O)-G- wherein G is sulfur or NH. The recurring units (b) may be of one type or a mixture of two or more types.

Of the recurring units (b), those units having a phenolic hydroxyl group are preferred since they have a sensitizing effect in the EB and EUV lithography. The recurring unit having a phenolic hydroxyl group is preferably at least one of recurring units (b1) to (b9) having the formulae (B1) to (B9).

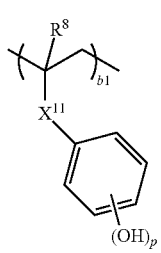
(B1)

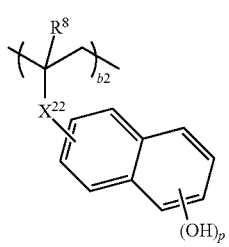
(B2)

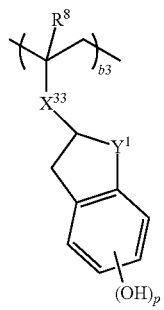
(B3)

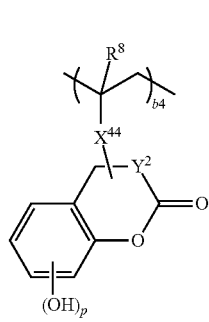
(B4)

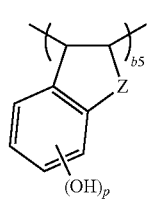
(B5)

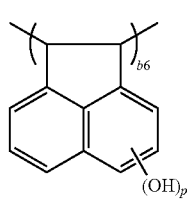
(B6)

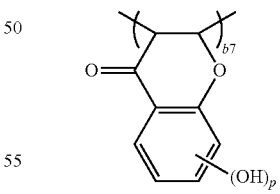
(B7)

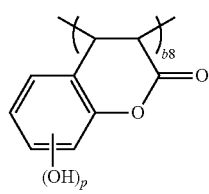
(B8)

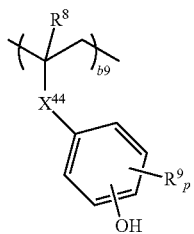
(B9)

Herein $R^8$ is hydrogen or methyl, $R^9$ is $C_1$-$C_4$ alkyl, —C(=O)—$R^{9a}$, —O—C(=O)—$R^{9a}$, —C(=O)—O—$R^{9a}$, cyano or nitro group, $X^{11}$ and $X^{22}$ are each independently a single bond or —C(=O)—O—$R^{10a}$—, $X^{33}$ and $X^{44}$ each are —C(=O)—O—$R^{10a}$—, $R^{9a}$ is $C_1$-$C_4$ alkyl or $C_2$-$C_4$ alkenyl, $R^{10a}$ is a single bond or a straight, branched or cyclic $C_1$-$C_{10}$ alkylene group, $Y^1$ and $Y^2$ are each independently methylene or ethylene, Z is methylene, oxygen or sulfur, p is 1 or 2, b1 to b9 are numbers in the range: $0 \leq b1 < 1.0$, $0 \leq b2 < 1.0$, $0 \leq b3 < 1.0$, $0 \leq b4 < 1.0$, $0 \leq b5 < 1.0$, $0 \leq b6 < 1.0$, $0 \leq b7 < 1.0$, $0 \leq b8 < 1.0$, $0 \leq b9 < 1.0$, and $0 \leq b1+b2+b3+b4+b5+b6+b7+b8+b9 < 1.0$.

Examples of suitable monomers from which the recurring units (b1) to (b9) are derived are given below.

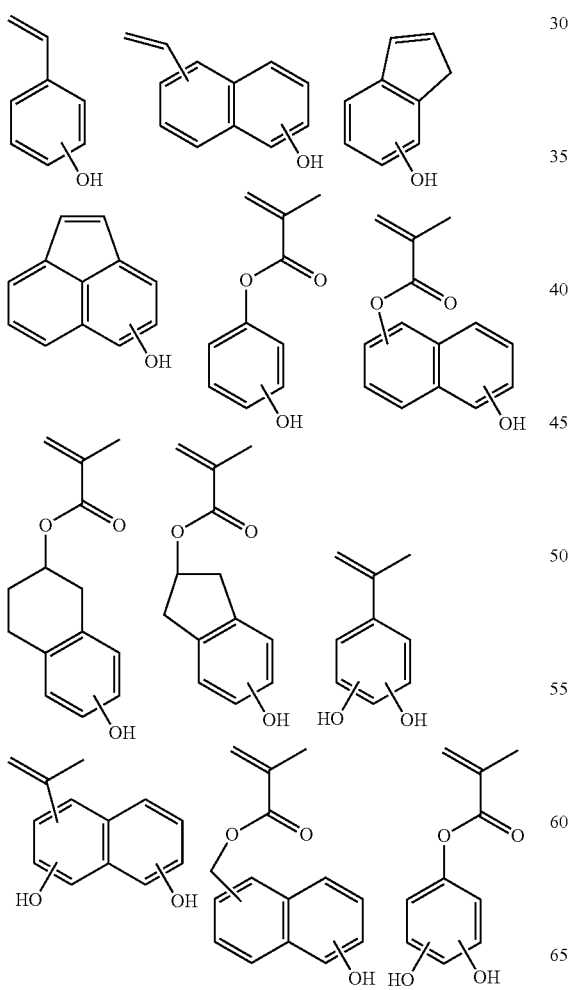

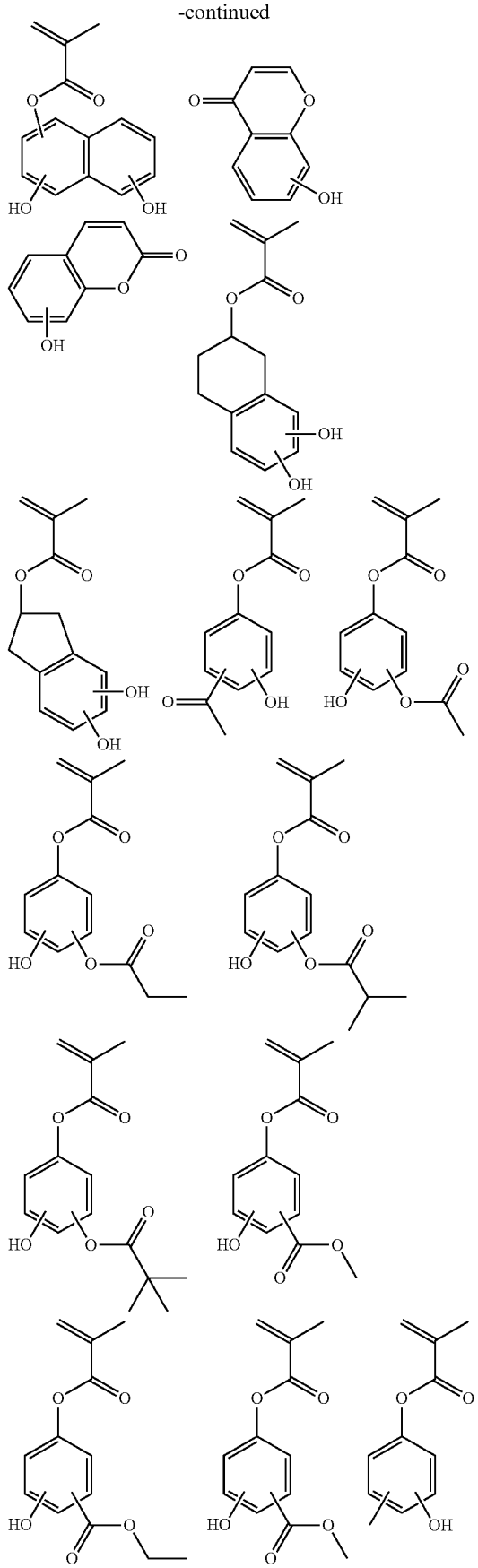

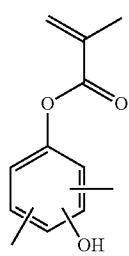
Examples of suitable monomers from which the recurring units (b) are derived are given below.
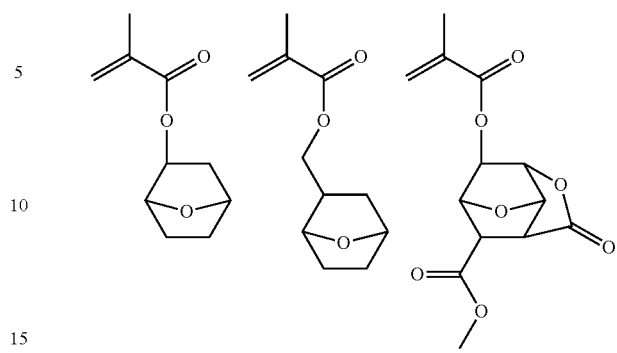
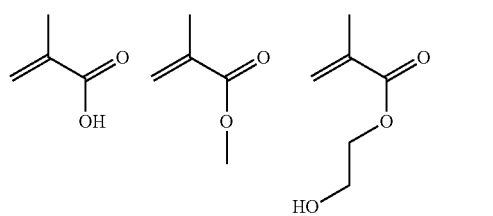
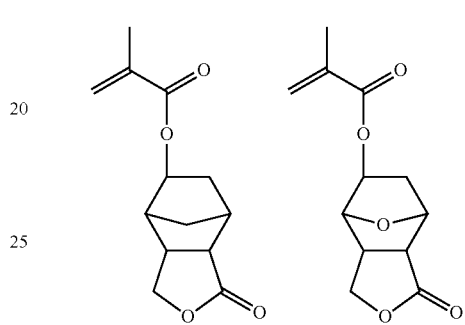
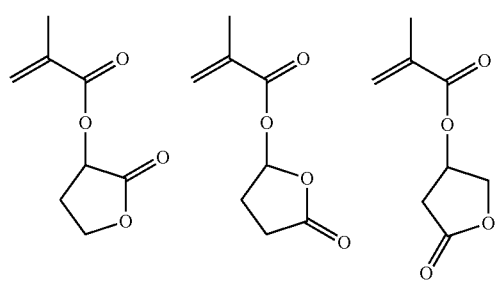
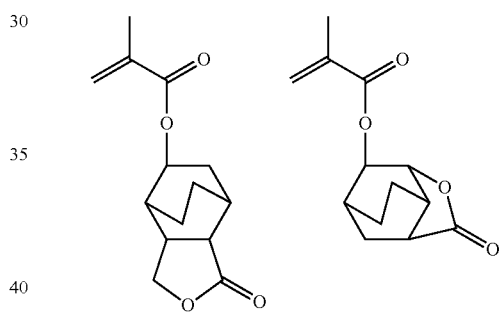
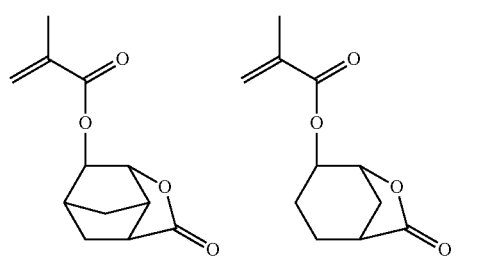
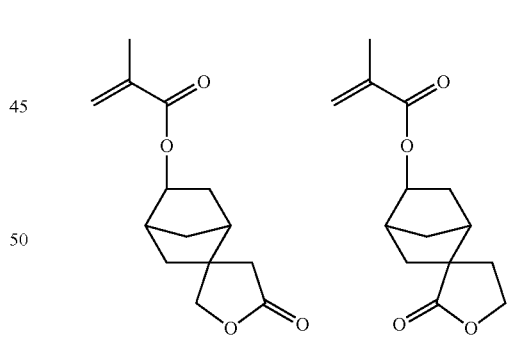
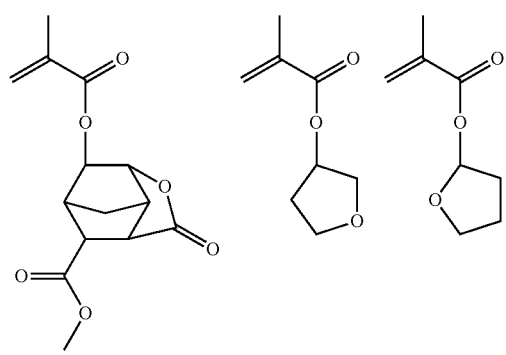
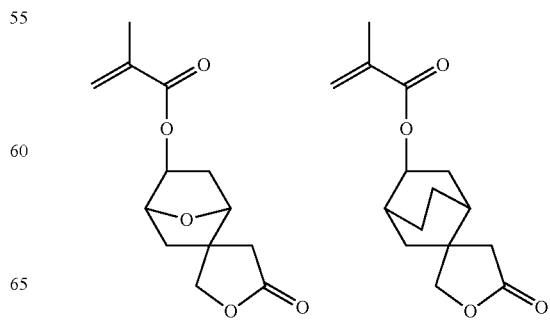

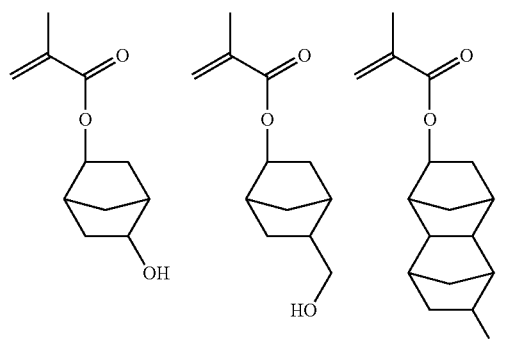
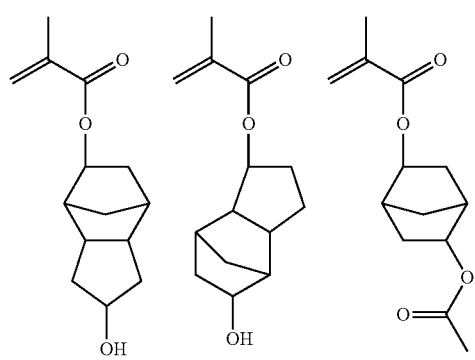
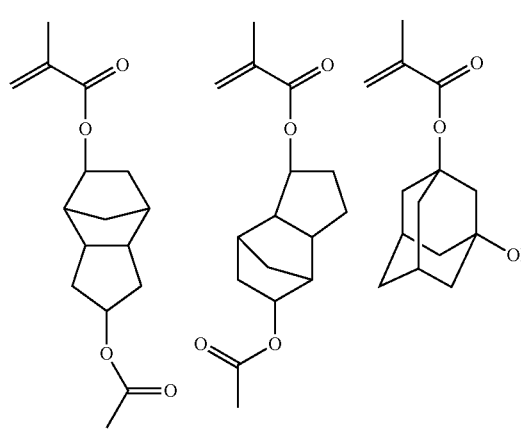
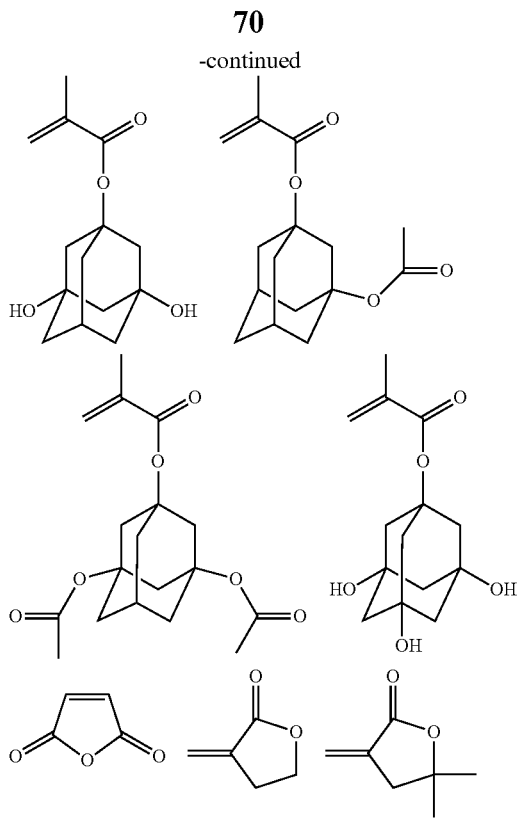
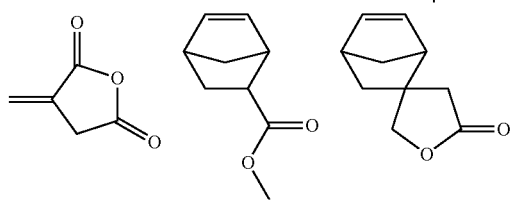
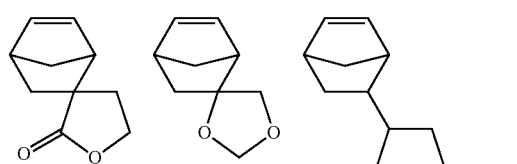
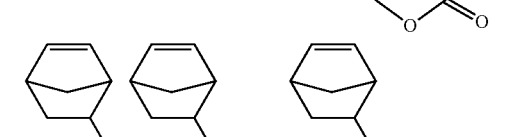
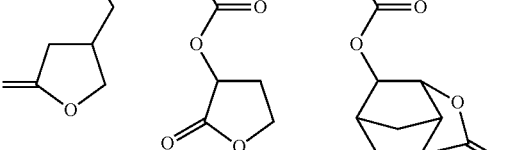
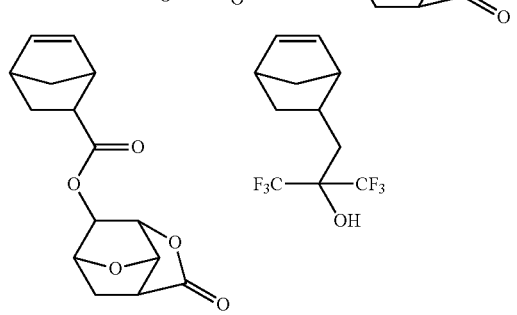

71
-continued
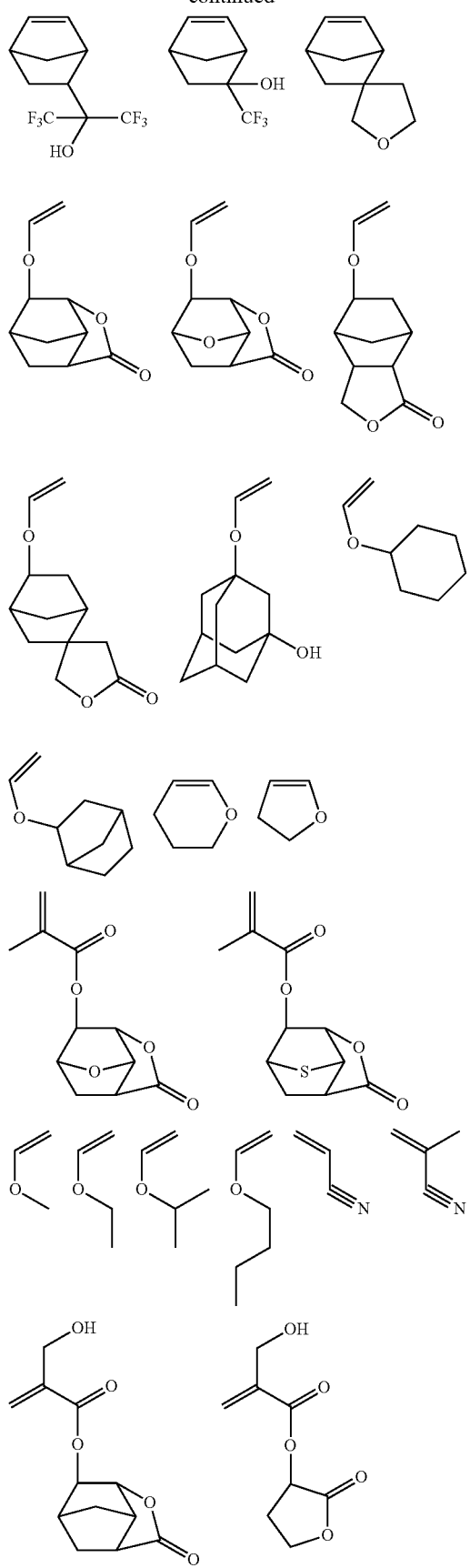
72
-continued
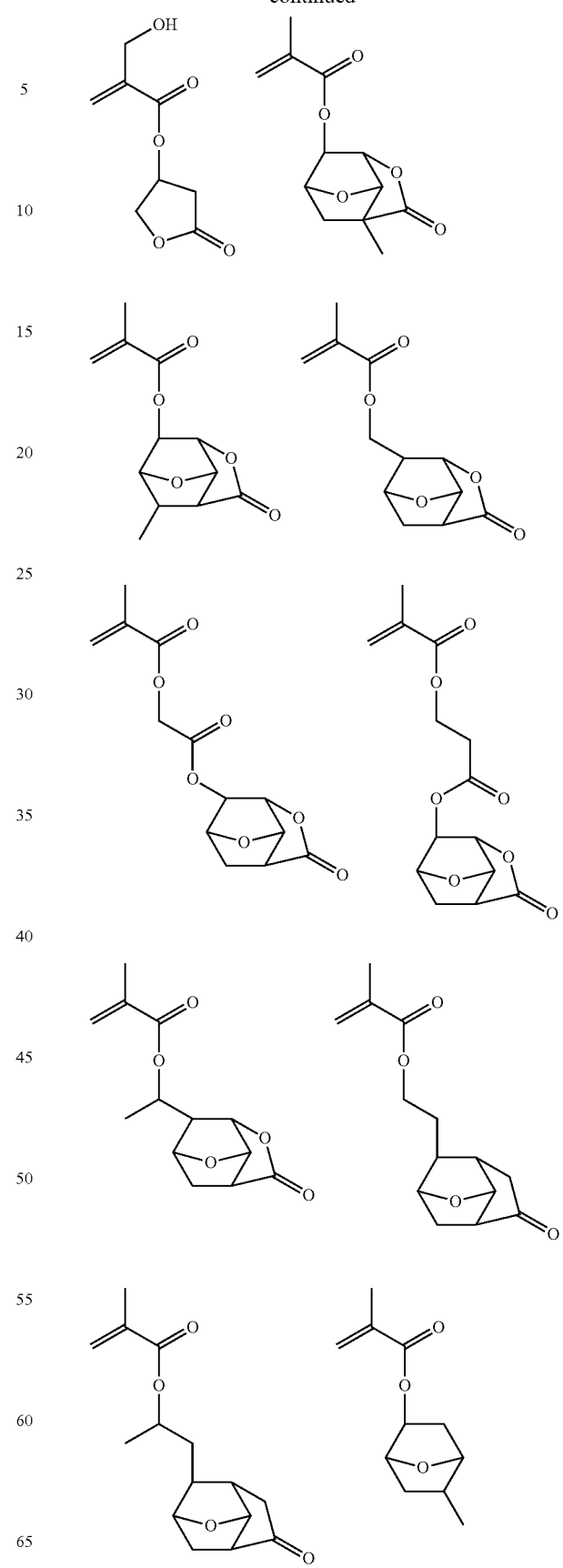

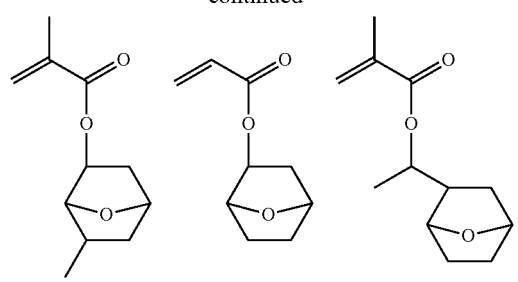
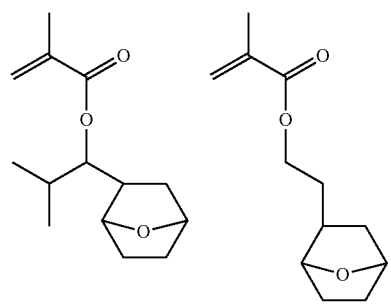
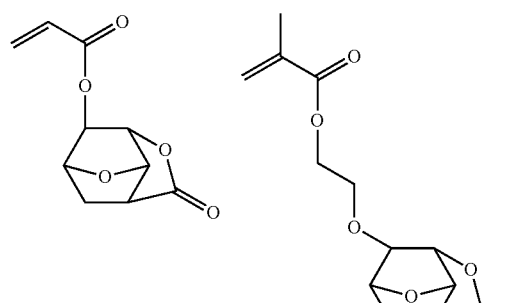
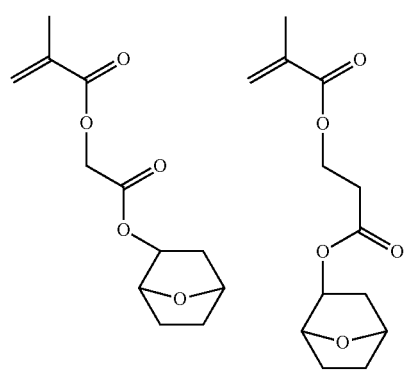
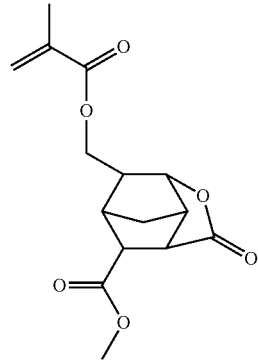
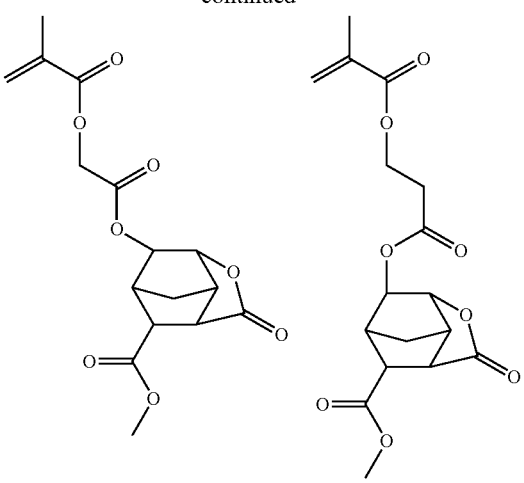
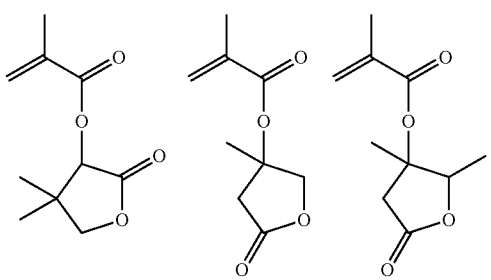
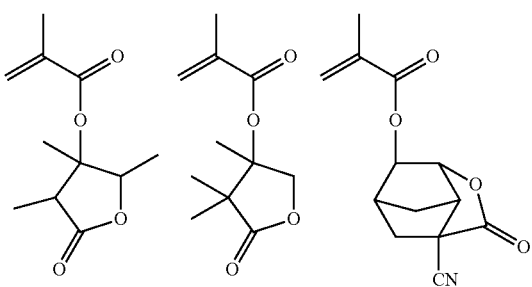
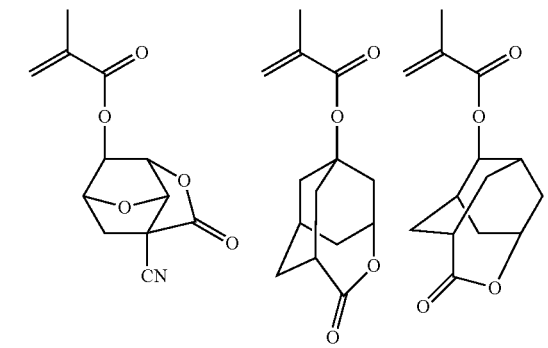
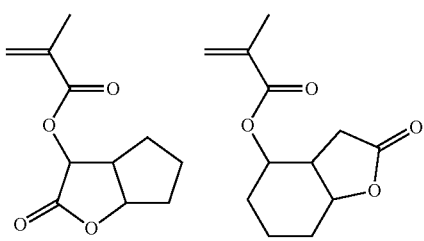

-continued
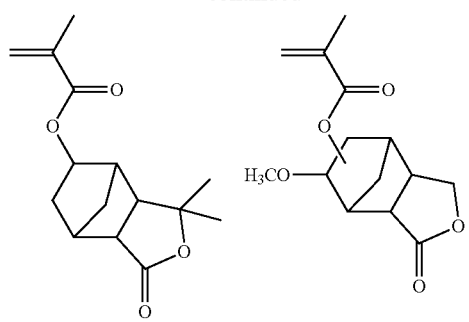
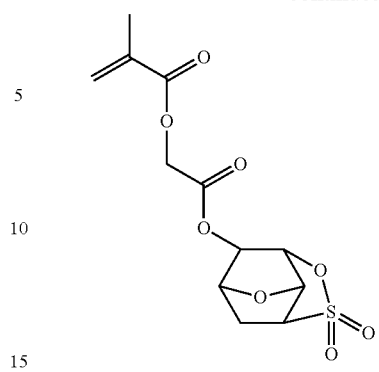
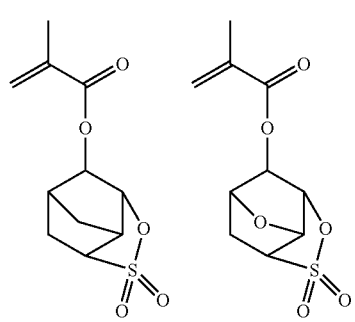
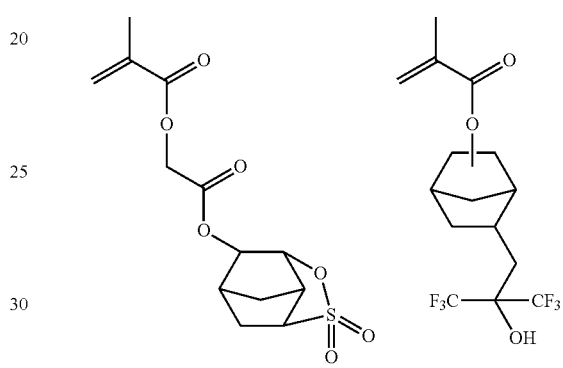
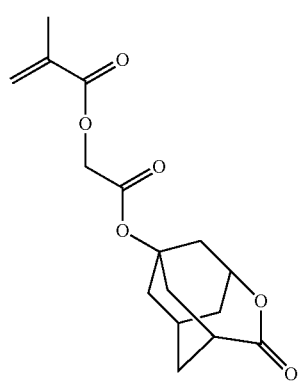
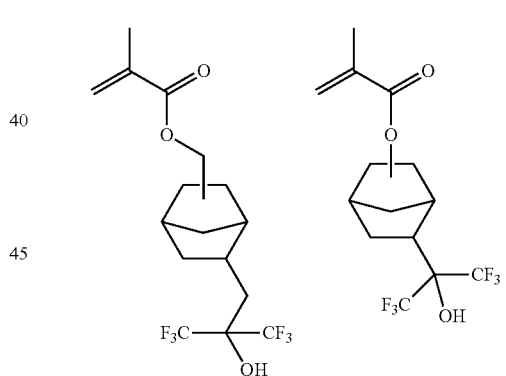
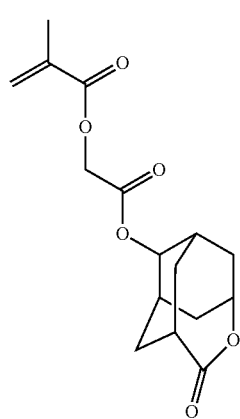
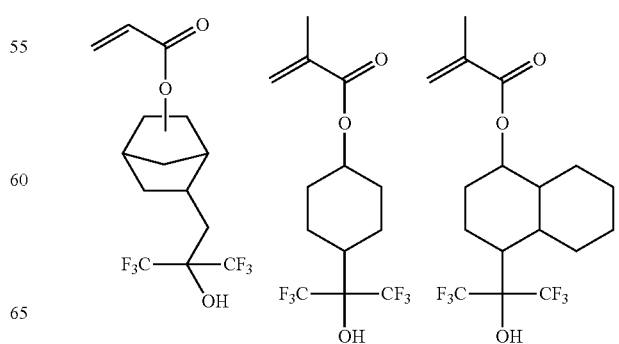

-continued
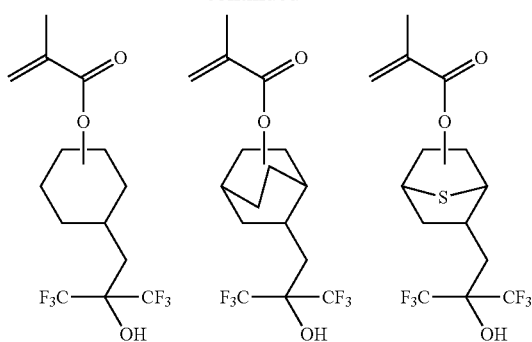
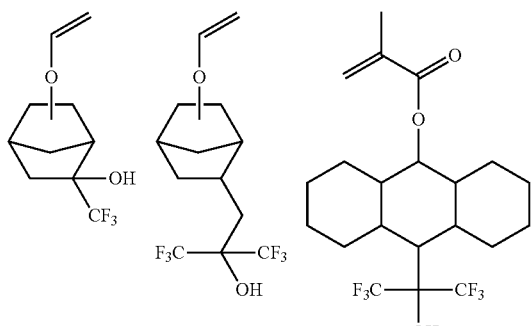
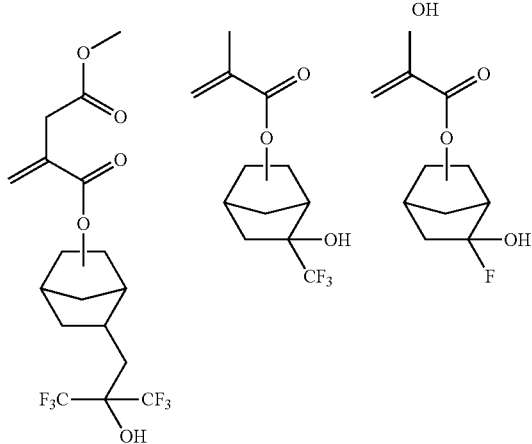
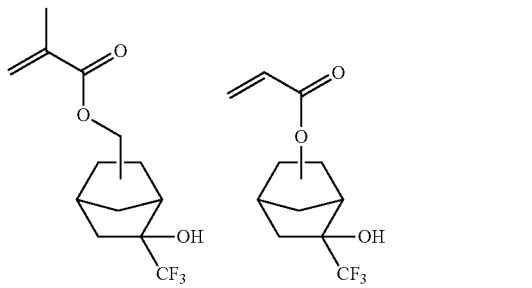
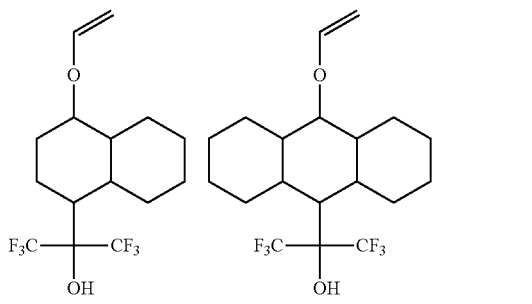
-continued
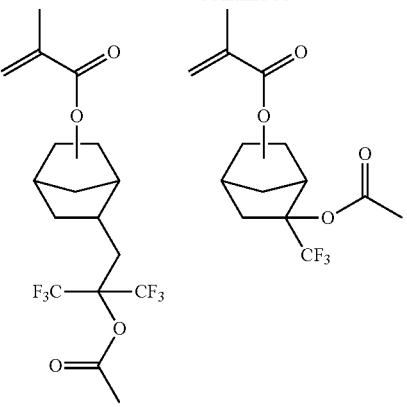
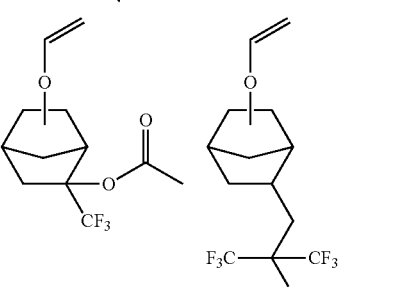
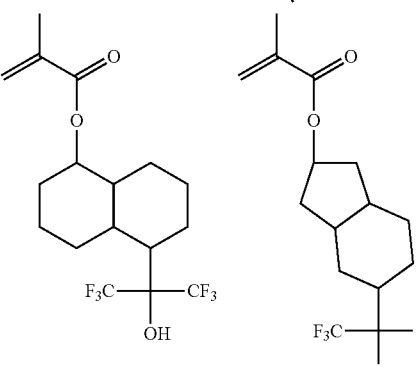
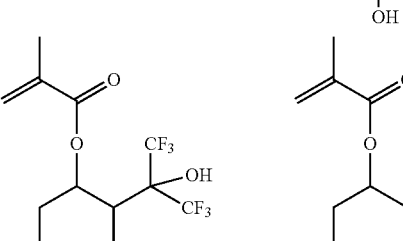
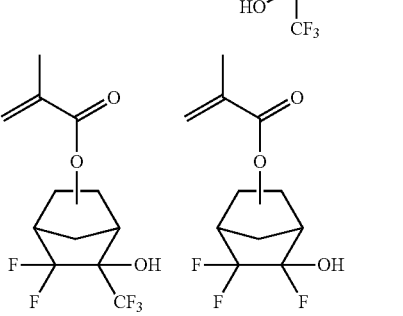

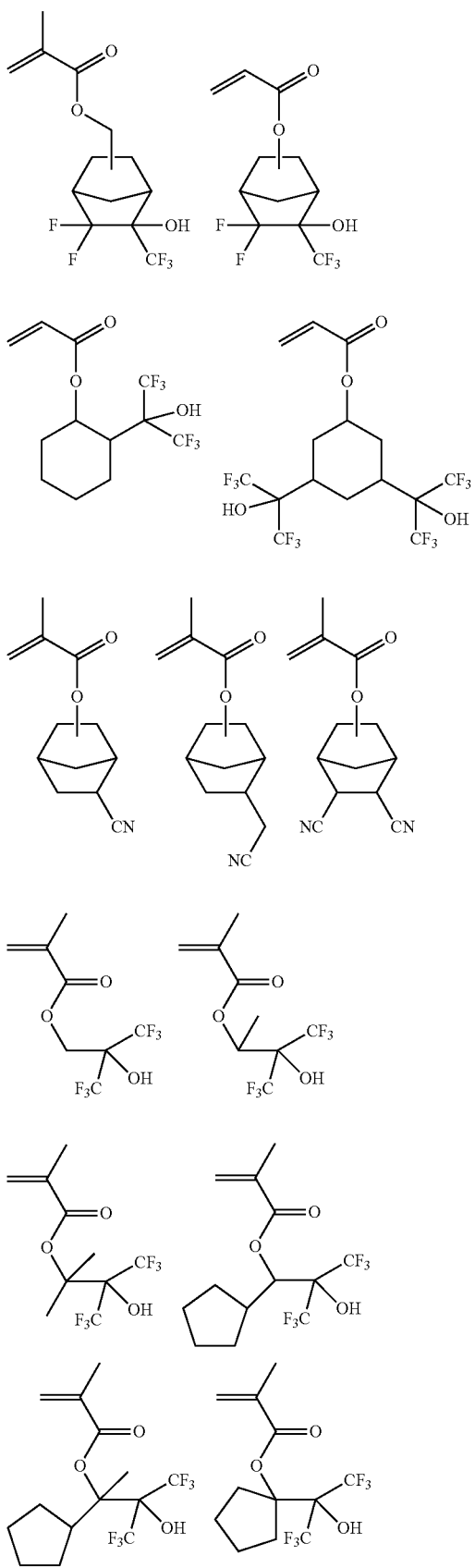
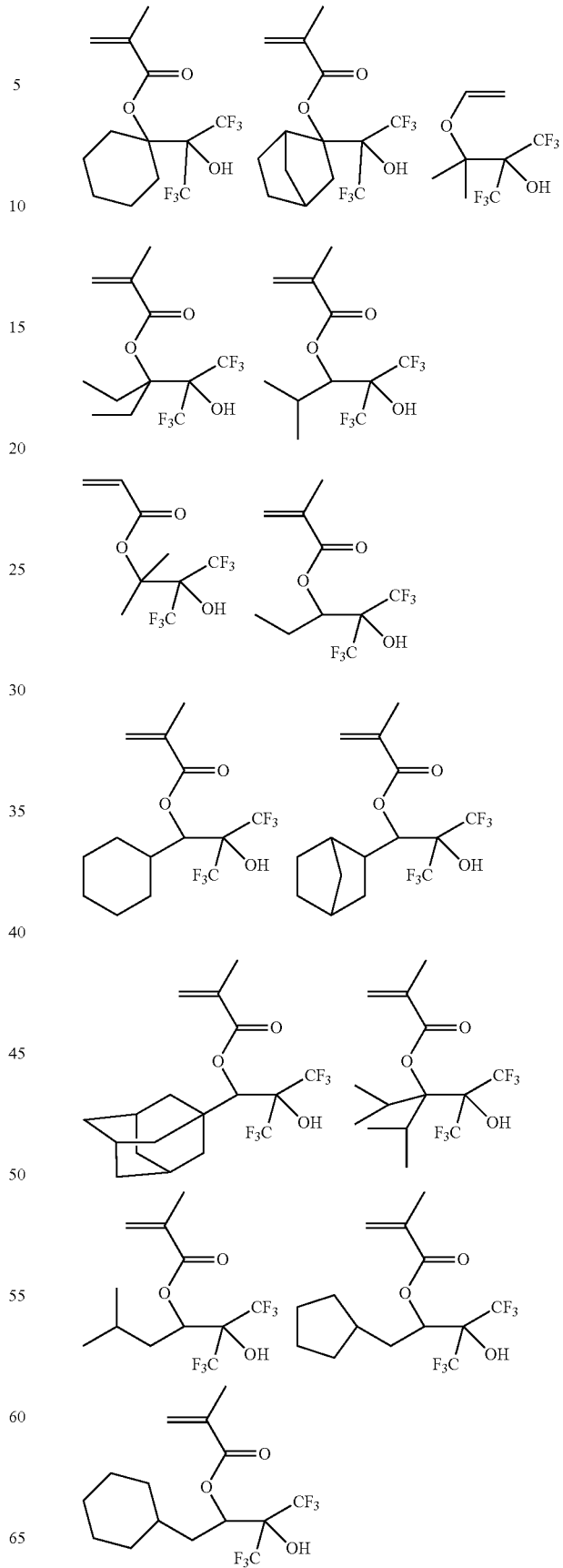

-continued
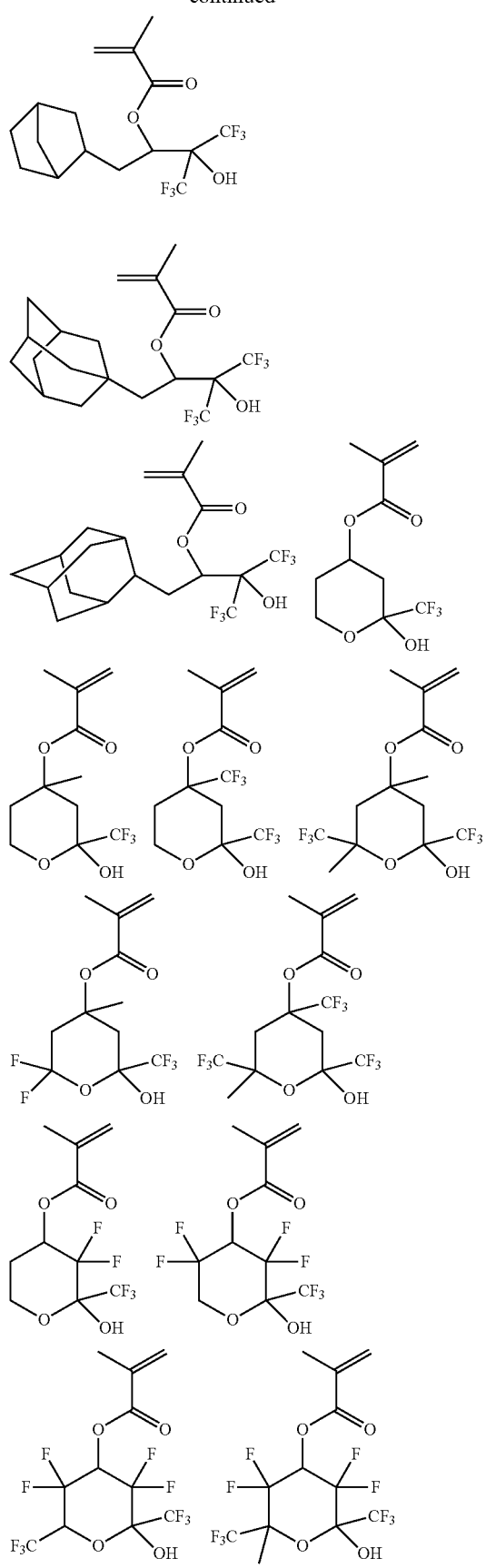
-continued
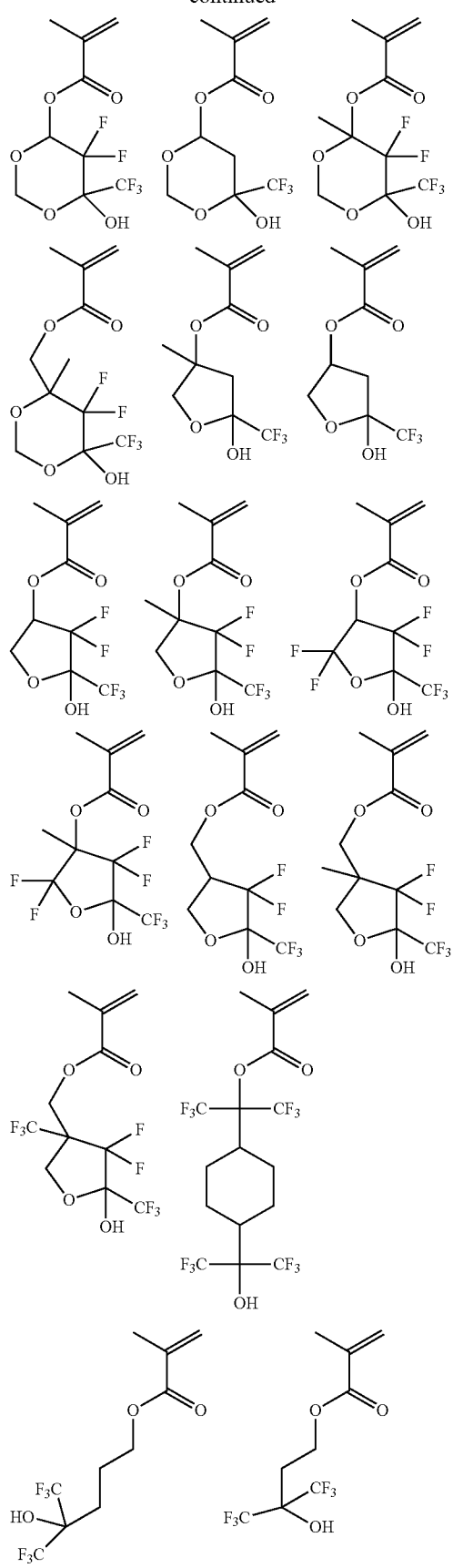

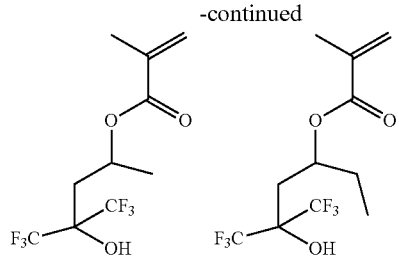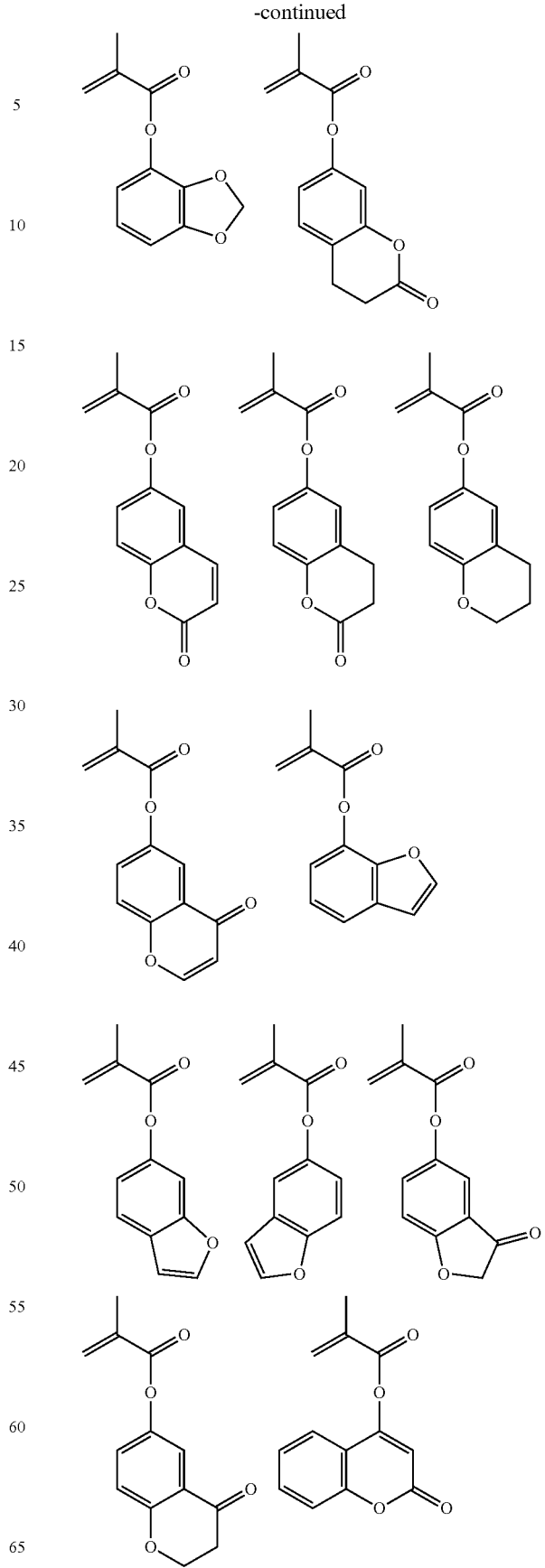

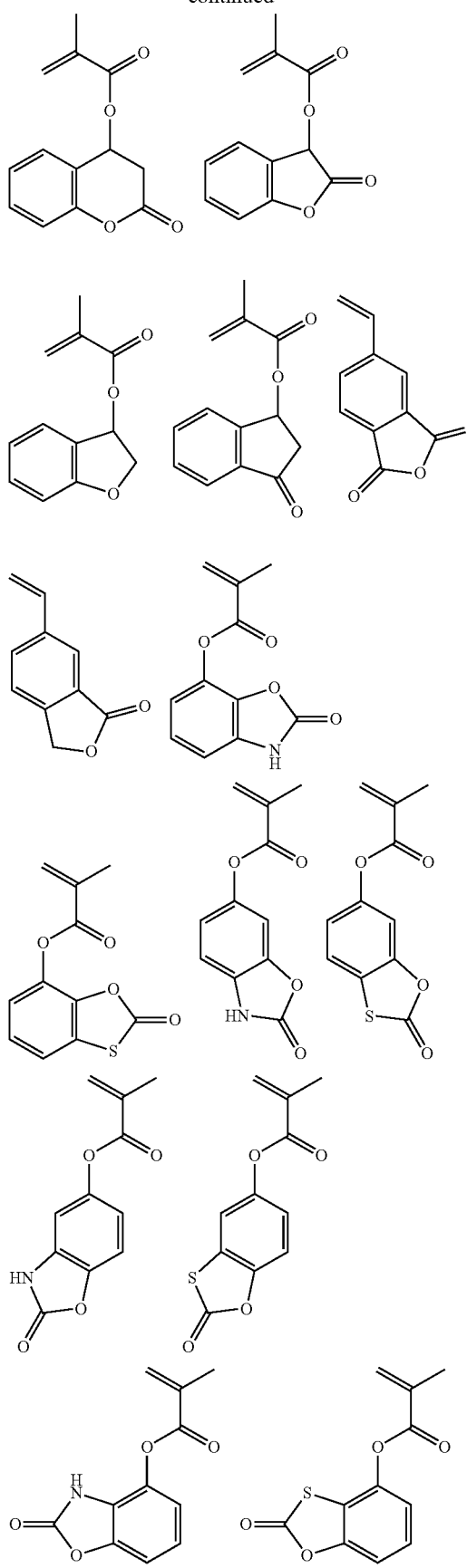
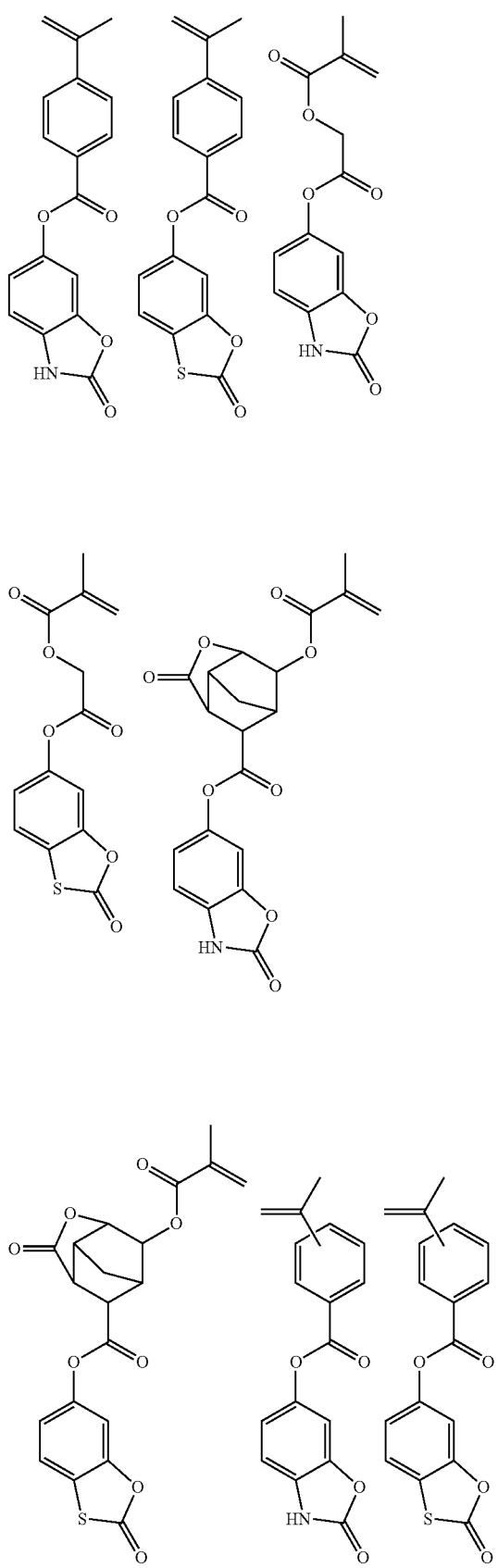

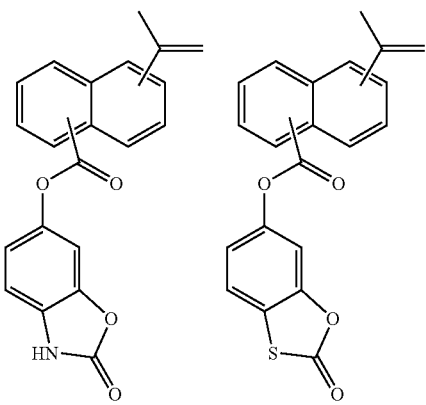

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

In another preferred embodiment, the polymer has further copolymerized therein recurring units (c) of at least one type selected from units (c1) to (c5) having the formulae (C1) to (C5).

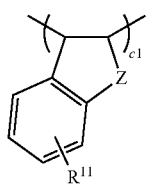 (C1)

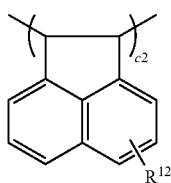 (C2)

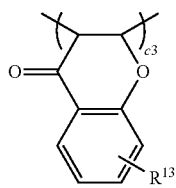 (C3)

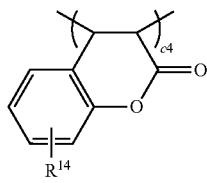 (C4)

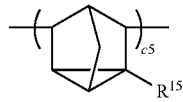 (C5)

Herein $R^{11}$ to $R^{15}$ are each independently hydrogen, a $C_1$-$C_{30}$ alkyl, $C_1$-$C_{30}$ alkyl wherein one or more or all carbon-bonded hydrogen atoms are substituted by halogen atoms, $C_1$-$C_8$ alkoxy, $C_1$-$C_8$ alkanoyl, $C_2$-$C_8$ alkoxycarbonyl, $C_6$-$C_{10}$ aryl, halogen, or 1,1,1,3,3,3-hexafluoro-2-propanol group, and Z is methylene, oxygen or sulfur, c1 to c5 are numbers in the range: $0 \leq c1 < 1.0$, $0 \leq c2 < 1.0$, $0 \leq c3 < 1.0$, $0 \leq c4 < 1.0$, $0 \leq c5 < 1.0$, and $0 \leq c1+c2+c3+c4+c5 < 1.0$.

Examples of suitable monomers from which recurring units (c1) to (c5) are derived are given below.

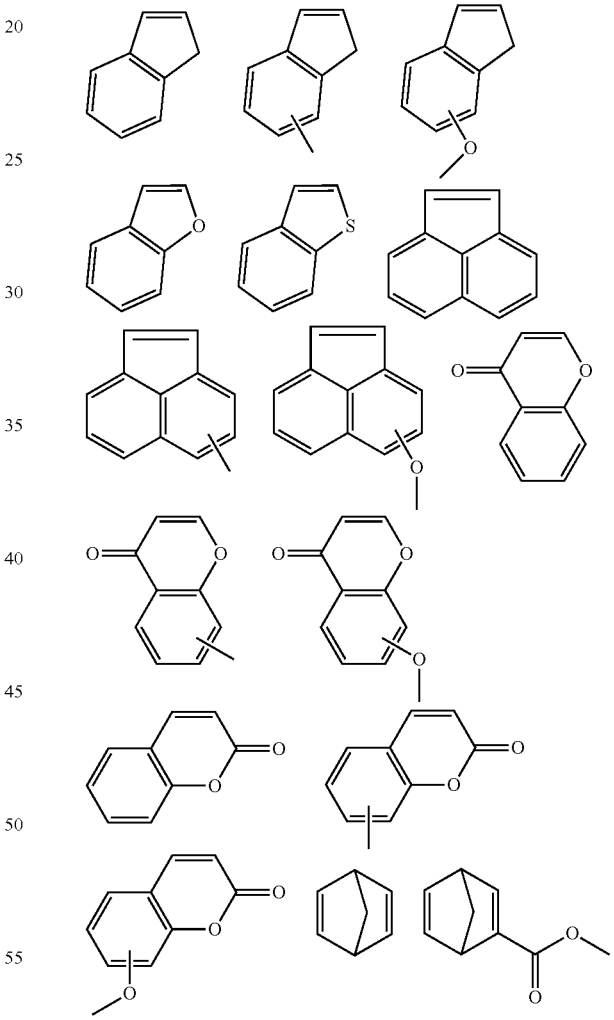

In a further preferred embodiment, the polymer may further comprise recurring units (d) derived from an acid generator in the form of an onium salt containing a polymerizable unsaturated bond. JP-A H04-230645, JP-A 2005-084365, and JP-A 2006-045311 disclose polymerizable unsaturated bond-containing sulfonium salts capable of generating a specific sulfonic acid and similar iodonium salts. JP-A 2006-178317 discloses a sulfonium salt having sulfonic acid directly attached to the main chain.

In this embodiment, the polymer comprises recurring units (d) of at least one type selected from recurring units (d1) to (d3) having the formulae (D1) to (D3).

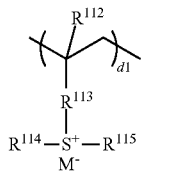
(D1)

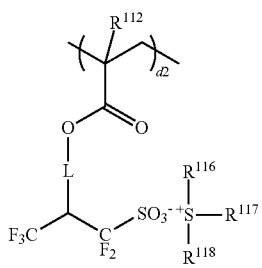
(D2)

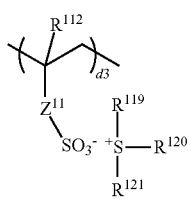
(D3)

Herein $R^{112}$ is each independently hydrogen or methyl. $R^{113}$ is a single bond, phenylene, —O—$R^{122}$—, or —C(=O)—$Z^{22}$—$R^{122}$— wherein $Z^{22}$ is oxygen or NH, and $R^{122}$ is a straight, branched or cyclic $C_1$-$C_6$ alkylene, $C_2$-$C_6$ alkenylene or phenylene group, which may contain a carbonyl, ester, ether or hydroxyl moiety. L is a single bond or —$Z^{33}$—C(=O)—O— wherein $Z^{33}$ is a straight, branched or cyclic $C_1$-$C_{20}$ divalent hydrocarbon group which may be substituted with a heteroatom. $Z^{11}$ is a single bond, methylene, ethylene, phenylene, fluorinated phenylene, or —C(=O)—$Z^{44}$—$R^{123}$—, wherein $Z^{44}$ is oxygen or NH, and $R^{123}$ is a straight, branched or cyclic $C_1$-$C_6$ alkylene, $C_2$-$C_6$ alkenylene or phenylene group, which may contain a carbonyl, ester, ether or hydroxyl moiety. $M^-$ is a non-nucleophilic counter ion. $R^{114}$, $R^{115}$, $R^{116}$, $R^{117}$, $R^{118}$, $R^{119}$, $R^{120}$, and $R^{121}$ are each independently a straight, branched or cyclic $C_1$-$C_{30}$ monovalent hydrocarbon group which may contain a heteroatom, d1, d2 and d3 are numbers in the range: $0 \le d1 \le 0.5$, $0 \le d2 \le 0.5$, $0 \le d3 \le 0.5$, and $0 \le d1+d2+d3 \le 0.5$.

Examples of the non-nucleophilic counter ion represented by $M^-$ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

The attachment of an acid generator to the polymer main chain is effective in restraining acid diffusion, thereby preventing a reduction of resolution due to blur by acid diffusion. Also edge roughness (LWR) is improved since the acid generator is uniformly dispersed.

The polymer may further comprise recurring units (e) of (meth)acrylate having substituted thereon an acid labile group $R^{41}$, represented by the following formula (E), and/or recurring units (f) of hydroxystyrene having substituted thereon an acid labile group $R^{43}$, represented by the following formula (F).

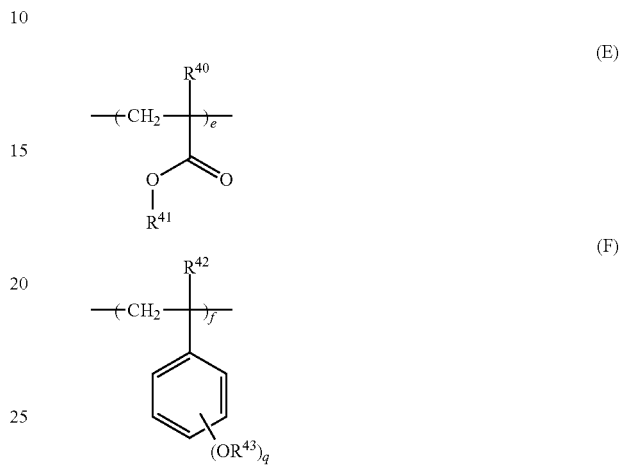

Herein $R^{40}$ and $R^{42}$ each are hydrogen or methyl, $R^{41}$ and $R^{43}$ each are an acid labile group, and q is 1 or 2.

The acid labile groups $R^{41}$ and $R^{43}$ in formulae (E) and (F) may be selected from the acid labile groups of formulae (A-1), (A-2), and (A-3).

Preferably, $R^{41}$ in formula (E) is an acid labile group of formula (A-3). In this embodiment, the preferred recurring units (e) are recurring units of (meth)acrylate having an exo-form structure represented by the following formula (A-3)-21.

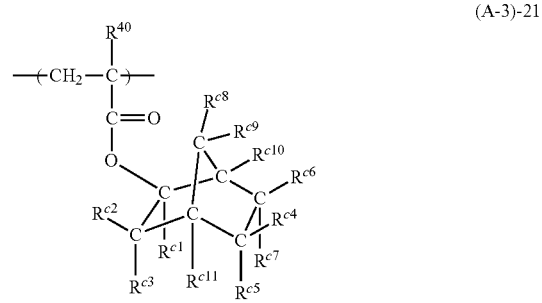
(A-3)-21

Herein, $R^{40}$ is as defined above; $R^{c1}$ is a straight, branched or cyclic $C_1$-$C_5$ alkyl group or $C_6$-$C_{20}$ aryl group in which some or all carbon-bonded hydrogen atoms may be substituted by halogen atoms; $R^{c2}$ to $R^{c7}$, $R^{c10}$ and $R^{c11}$ are each independently hydrogen or a $C_1$-$C_{15}$ monovalent hydrocarbon group which may contain a heteroatom; and $R^{c8}$ and $R^{c9}$ are hydrogen. Alternatively, a pair of $R^{c2}$ and $R^{c3}$, $R^{c4}$ and $R_{c6}$, $R^{c4}$ and $R^{c7}$, $R^{c5}$ and $R^{c7}$, $R^{c5}$ and $R^{c11}$, $R^{c6}$ and $R^{c10}$, $R^{c8}$ and $R^{c9}$, or $R^{c9}$ and $R^{c10}$ may bond together to form a ring with the carbon atom to which they are attached, and in that event, each of ring-forming $R^{c2}$ and $R^{c3}$, $R^{c4}$ and $R^{c6}$, $R^{c4}$ and $R^{c7}$, $R^{c5}$ and $R^{c7}$, $R^{c5}$ and $R^{c11}$, $R^{c6}$ and $R^{c10}$, $R^{c8}$ and $R^{c9}$, or $R^{c9}$ and $R^{c10}$ is a $C_1$-$C_{15}$ divalent hydrocarbon group which may contain a heteroatom. Also, a pair of $R^{c2}$ and $R^{c11}$, $R^{c8}$ and $R^{c11}$, or $R^{c4}$ and $R^{c6}$ which are attached to vicinal carbon atoms may bond together directly to form a double bond. The formula also represents an enantiomer.

Suitable monomers from which the recurring units having formula (A-3)-21 are derived include those described in U.S. Pat. No. 6,448,420 (JP-A 2000-327633). Illustrative non-limiting examples of suitable monomers are given below.

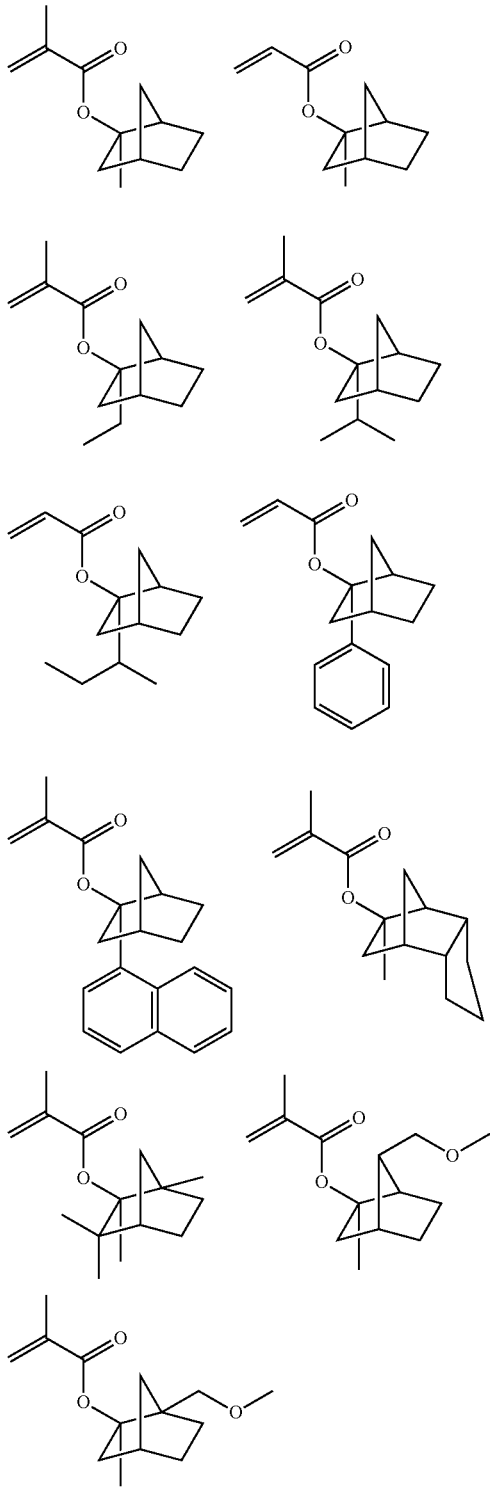

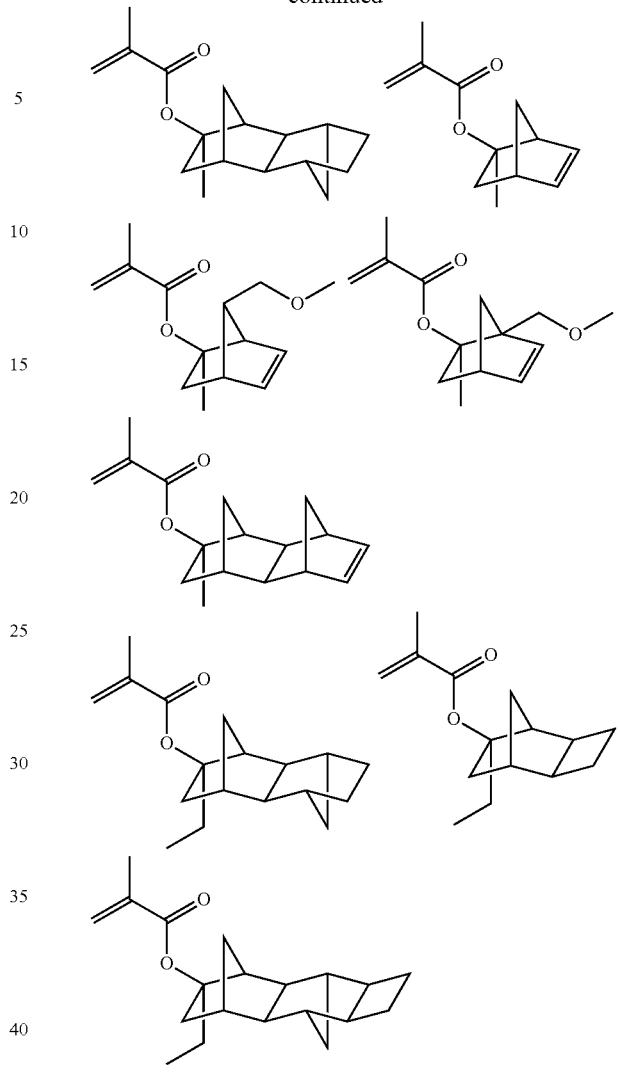

Other preferred examples of the recurring units (a) include recurring units derived from (meth)acrylates having furandiyl, tetrahydrofurandiyl or oxanorbornanediyl substituted thereon, as represented by the following formula (A-3)-22.

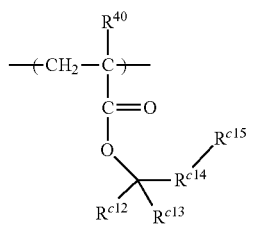

(A-3)-22

Herein, $R^{40}$ is as defined above. $R^{c12}$ and $R^{c13}$ are each independently a straight, branched or cyclic $C_1$-$C_{10}$ monovalent hydrocarbon group. Alternatively, $R^{c12}$ and $R^{c13}$ may bond together to form an aliphatic hydrocarbon ring with the carbon atom to which they are attached, and a ring-forming combination of $R^{c12}$ and $R^{c13}$ is a $C_1$-$C_{10}$ divalent hydrocarbon group, typically alkylene. $R^{c14}$ is furandiyl, tetrahydrofurandiyl or oxanorbornanediyl. $R^{c15}$ is hydrogen or a straight, branched or cyclic $C_1$-$C_{10}$ monovalent hydrocarbon group which may contain a heteroatom.
Examples of the monomers from which the recurring units having formula (A-3)-22 are derived are shown below, but not limited thereto.
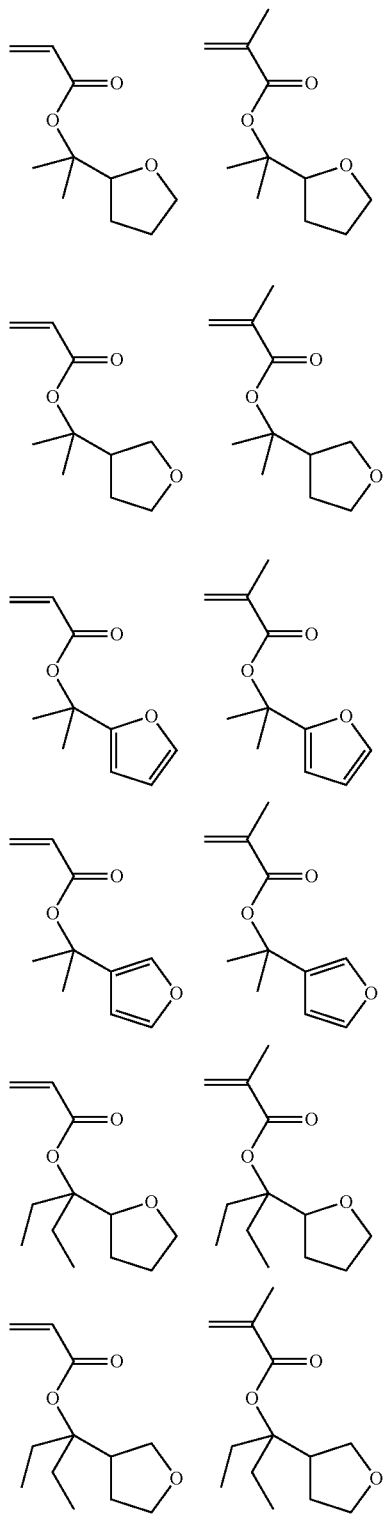
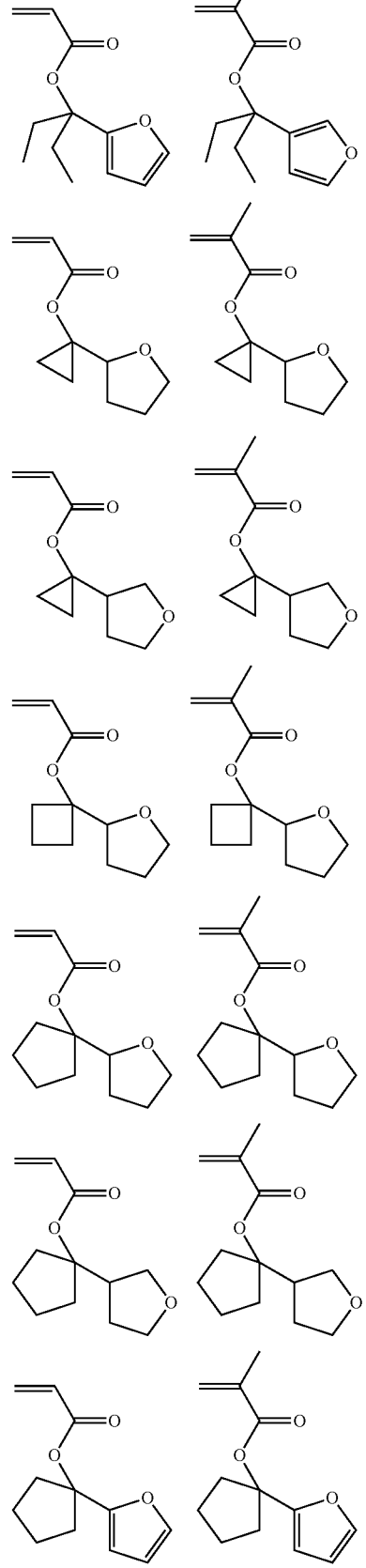

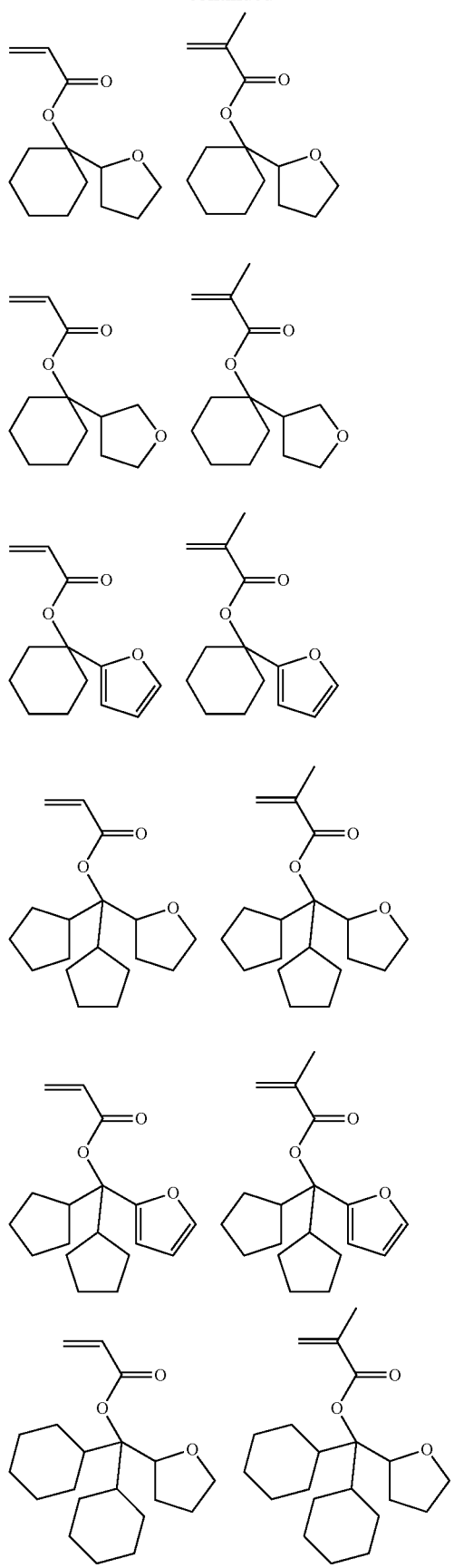
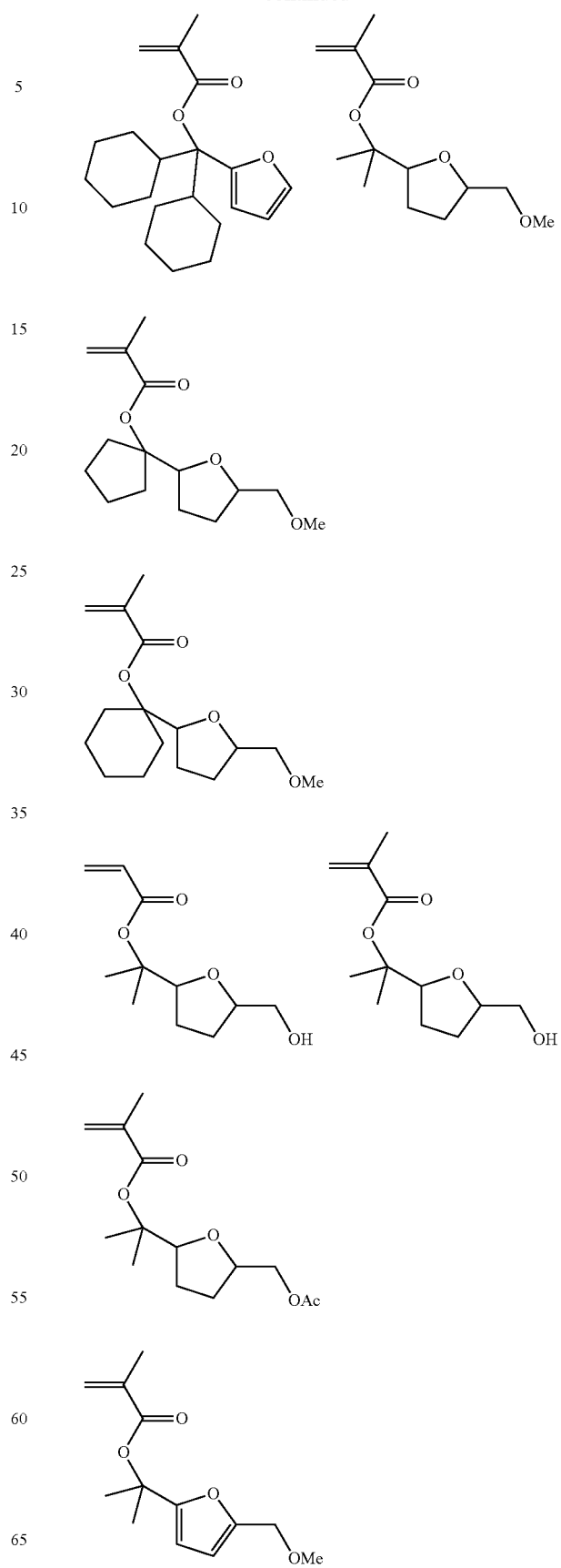

-continued
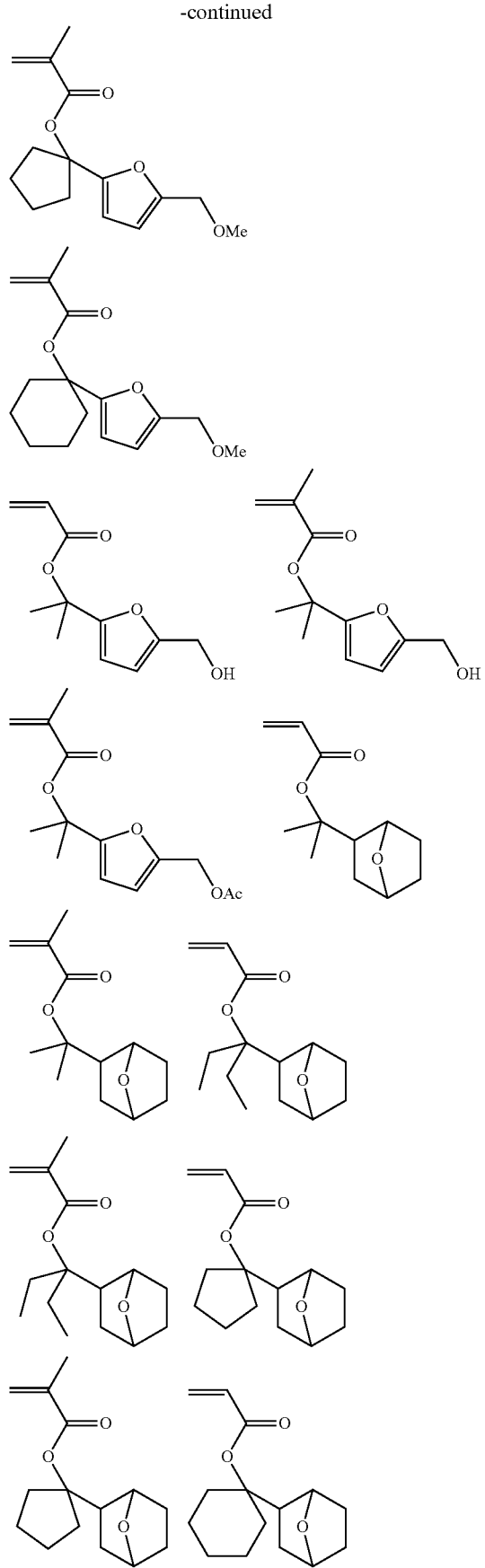
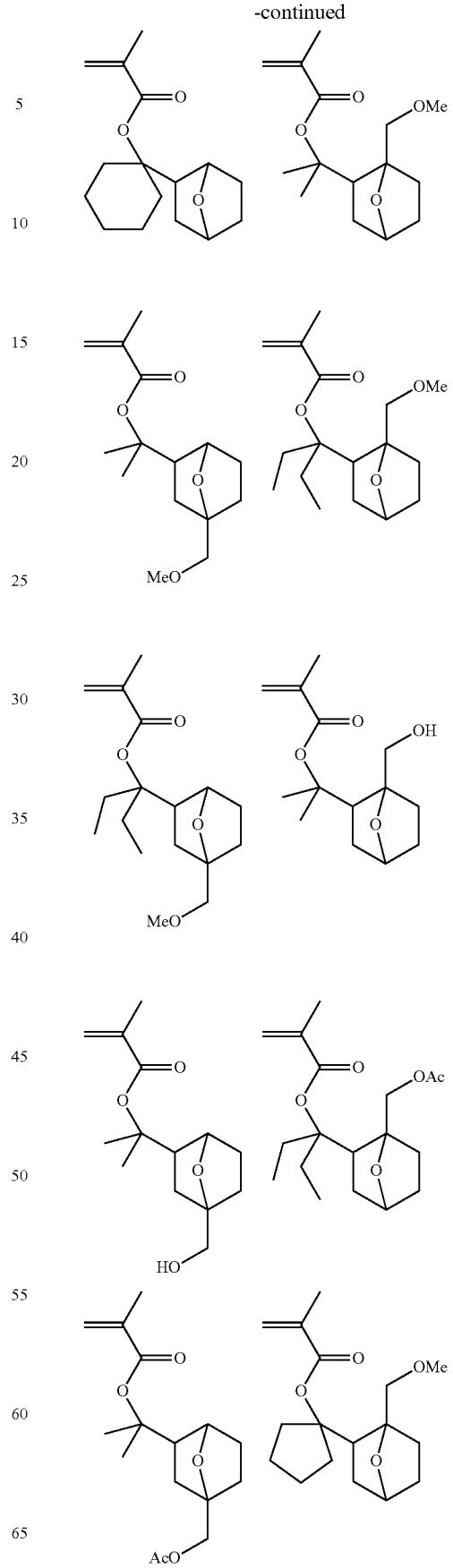

-continued

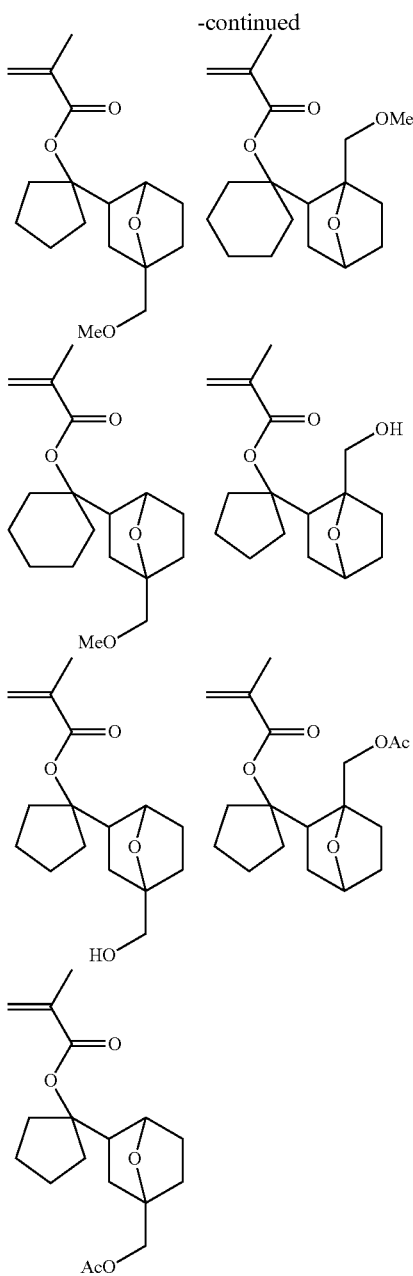

Besides the recurring units (a) to (f), additional recurring units (g) may be copolymerized in the polymer, which include recurring units derived from styrene, vinylnaphthalene, vinylanthracene, vinylpyrene, methyleneindane, and the like.

The polymer used herein may be synthesized by any desired methods, for example, by dissolving one or more monomers selected from the monomers corresponding to the recurring units (a) to (g) in an organic solvent, adding a radical polymerization initiator thereto, and effecting heat polymerization. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is typically 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the units to hydroxystyrene or hydroxyvinylnaphthalene units. For alkaline hydrolysis, a base such as aqueous ammonia or triethylamine may be used. The reaction temperature is typically −20° C. to 100° C., preferably 0° C. to 60° C., and the reaction time is typically 0.2 to 100 hours, preferably 0.5 to 20 hours.

In the polymer, recurring units (a) to (g) may be incorporated in the following molar fraction:
$0 < a \leq 1.0$, preferably $0 < a < 1.0$, more preferably $0.05 \leq a \leq 0.8$, and even more preferably $0.08 \leq a \leq 0.7$;
$0 \leq b < 1.0$, preferably $0 < b < 1.0$, more preferably $0.1 \leq b \leq 0.9$, and even more preferably $0.15 \leq b \leq 0.8$;
$0 \leq c < 1.0$, preferably $0 \leq c \leq 0.9$, and more preferably $0 \leq c \leq 0.8$;
$0 \leq d \leq 0.5$, preferably $0 \leq d \leq 0.4$, and more preferably $0 \leq d \leq 0.3$;
$0 \leq e \leq 0.5$, preferably $0 \leq e \leq 0.4$, and more preferably $0 \leq e \leq 0.3$;
$0 \leq f \leq 0.5$, preferably $0 \leq f \leq 0.4$, and more preferably $0 \leq f \leq 0.3$;
$0 \leq g \leq 0.5$, preferably $0 \leq g \leq 0.4$, and more preferably $0 \leq g \leq 0.3$;
preferably $0.2 \leq a+b+c \leq 1.0$, more preferably $0.3 \leq a+b+c \leq 1.0$; and $a+b+c+d+e+f+g=1$.

The meaning of $a+b+c=1$, for example, is that in a polymer comprising recurring units (a), (b), and (c), the sum of recurring units (a), (b), and (c) is 100 mol % based on the total amount of entire recurring units. The meaning of $a+b+c<1$ is that the sum of recurring units (a), (b), and (c) is less than 100 mol % based on the total amount of entire recurring units, indicating the inclusion of other recurring units.

The polymer serving as the base resin in the resist composition should have a weight average molecular weight (Mw) in the range of 1,000 to 500,000, and preferably 2,000 to 30,000, as measured by gel permeation chromatography (GPC) versus polystyrene standards. With too low a Mw, the resist composition may become less heat resistant. A polymer with too high a Mw may lose alkaline solubility and give rise to a footing phenomenon after pattern formation.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the polymer should preferably have a narrow dispersity (Mw/Mn) of 1.0 to 2.0, especially 1.0 to 1.5, in order to provide a resist composition suitable for micropatterning to a small feature size.

Resist Composition

The polymer is advantageously used as a base resin in a positive resist composition, typically chemically amplified positive resist composition. The positive resist composition comprises the polymer defined herein as a base resin and an organic solvent. It is understood that as the base resin, a blend of two or more inventive polymers which differ in compositional ratio, molecular weight or dispersity is acceptable as well as a blend of one or more inventive polymer and one or more conventional polymer.

Examples of the organic solvent used herein are described in JP-A 2008-111103, paragraphs [0144]-[0145] (U.S. Pat. No. 7,537,880). Exemplary solvents include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture. An appropriate amount of the organic solvent used is 50 to 10,000 parts, more preferably 100 to 5,000 parts by weight relative to 100 parts by weight of the base resin.

The positive resist composition may further include a photoacid generator in order for the composition to function as a chemically amplified positive resist composition. The PAG used herein is any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators, which may be used alone or in admixture. Preferred as the acid generated by PAG are strong acids such as sulfonic acid, bis(perfluoroalkanesulfonyl)imide and tris(perfluoromethanesulfonyl)methide.

Exemplary PAGs are described in JP-A 2008-111103, paragraphs [0122]-[0142] (U.S. Pat. No. 7,537,880). The preferred PAGs include the compounds described in JP-A 2014-001259, paragraphs [0088]-[0092], the compounds described in JP-A 2012-041320, paragraphs [0015]-[0017], and the compounds described in JP-A 2012-106986, paragraphs [0015]-[0029]. In particular, the PAGs capable of generating partially fluorinated sulfonic acids in these patent documents are used in the ArF lithography because the generated acid has an appropriate strength and diffusion length.

As the PAG used herein, those having the formulae (2) and (3) are preferred.

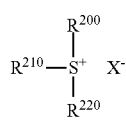
(2)

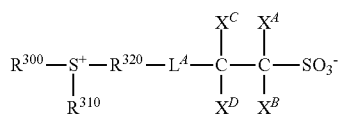
(3)

In formula (2), $R^{200}$, $R^{210}$ and $R^{220}$ are each independently a straight, branched or cyclic $C_1$-$C_{20}$ monovalent hydrocarbon group which may contain a heteroatom. Any two or more of $R^{200}$, $R^{210}$ and $R^{220}$ may bond together to form a ring with the sulfur atom to which they are attached.

In formula (2), $X^-$ is an anion of the following formula (2A), (2B), (2C) or (2D).

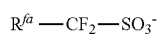
(2A)

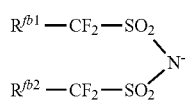
(2B)

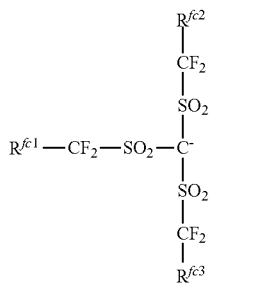
(2C)

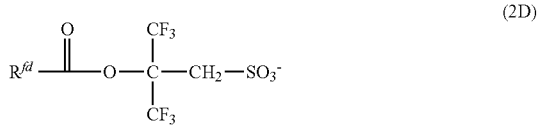
(2D)

In formula (2A), $R^{fa}$ is fluorine or a straight, branched or cyclic $C_1$-$C_{40}$ monovalent hydrocarbon group which may contain a heteroatom.

Of the anions of formula (2A), an anion having the formula (2A') is preferred.

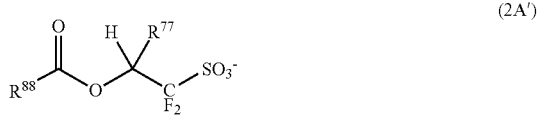
(2A')

In formula (2A'), $R^{77}$ is hydrogen or trifluoromethyl, preferably trifluoromethyl. $R^{88}$ is a straight, branched or cyclic $C_1$-$C_{38}$ monovalent hydrocarbon group which may contain a heteroatom. As the heteroatom, oxygen, nitrogen, sulfur and halogen atoms are preferred, with oxygen being most preferred. Of the monovalent hydrocarbon groups represented by $R^{88}$, those groups of 6 to 30 carbon atoms are preferred from the aspect of achieving a high resolution in forming patterns of fine feature size. Suitable monovalent hydrocarbon groups include, but are not limited to, methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoromethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, one or more hydrogen atoms may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl, cyano, carbonyl, ether bond, ester bond, sulfonic acid ester bond, carbonate bond, lactone ring, sultone ring, carboxylic anhydride or haloalkyl moiety.

With respect to the synthesis of the sulfonium salt having an anion of formula (2A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the sulfonium salt having an anion of formula (2A) are shown below, but not limited thereto.
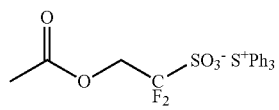
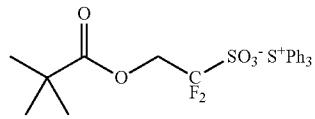
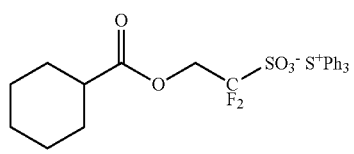
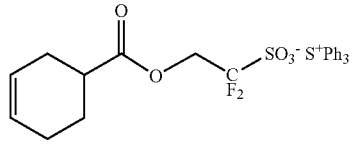
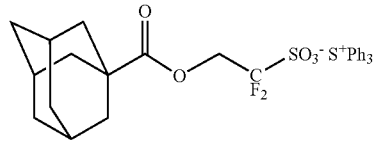
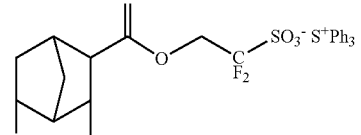
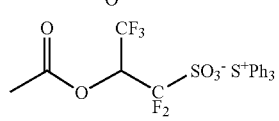
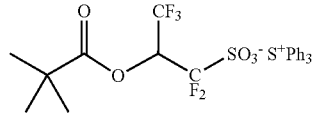
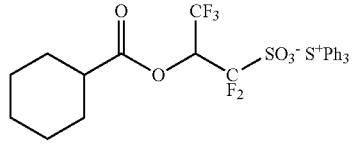
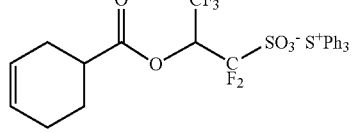
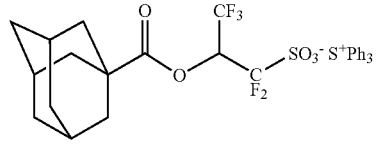
-continued
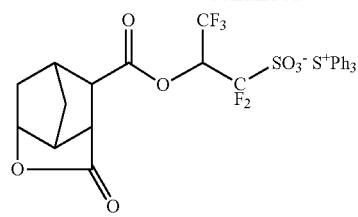
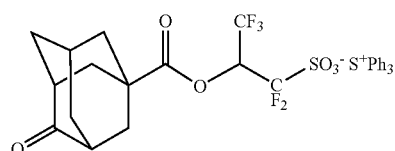
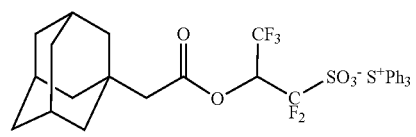
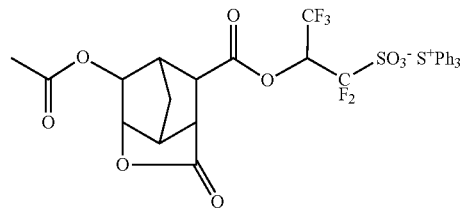
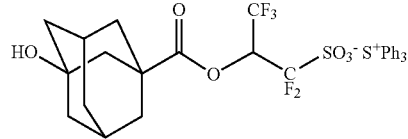
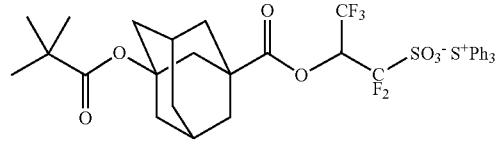
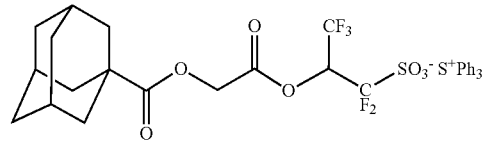
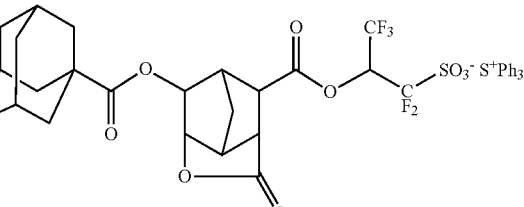
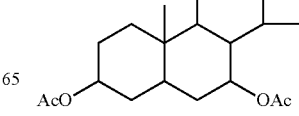

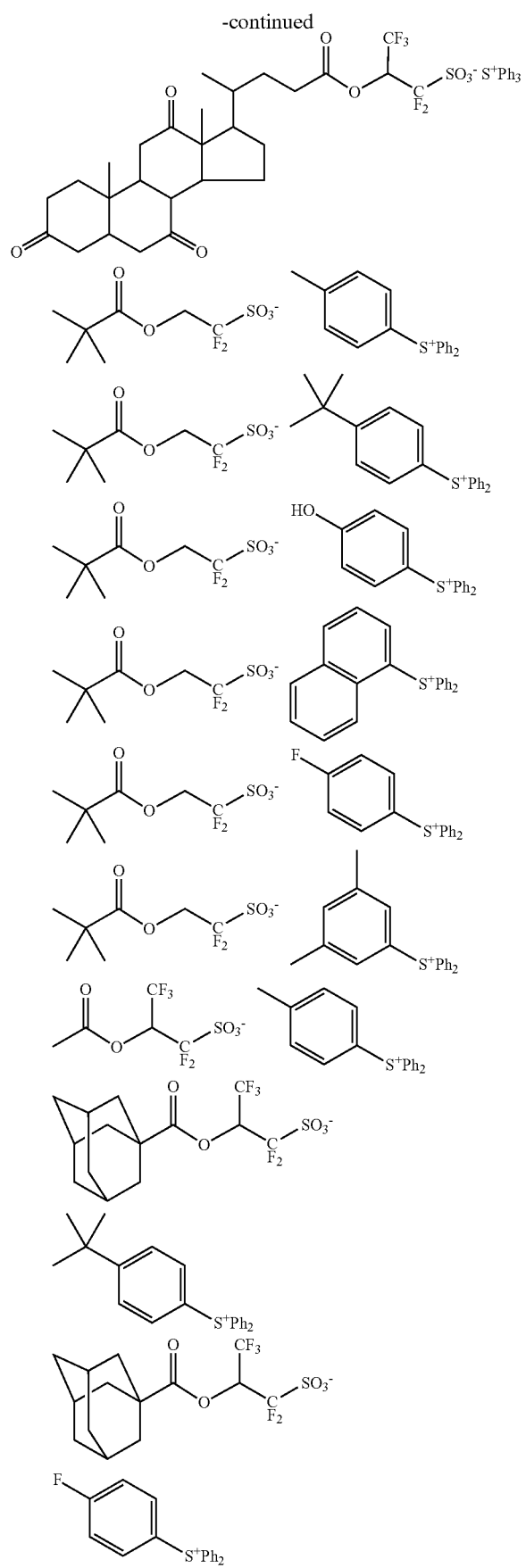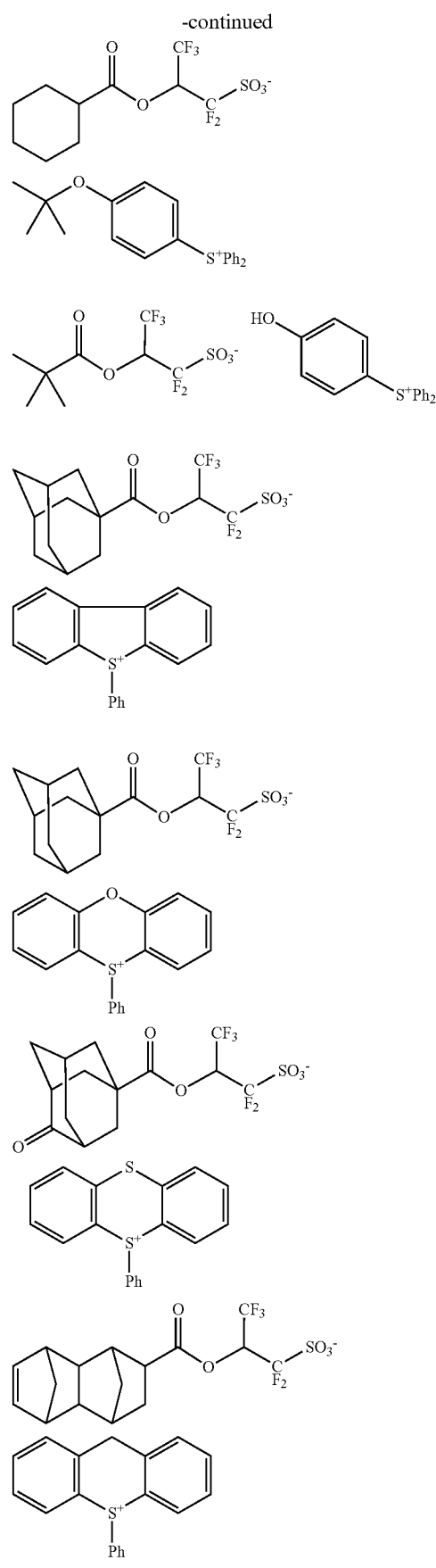

-continued
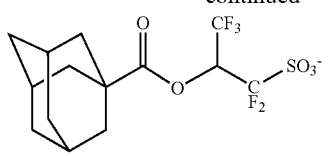
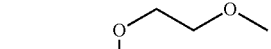
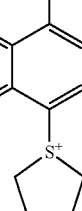
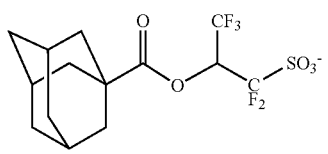
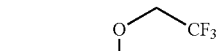
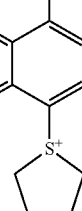
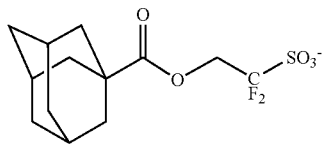
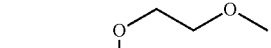
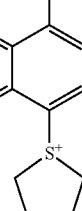
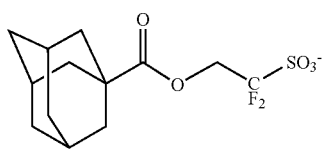
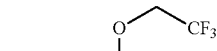
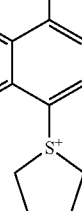
-continued
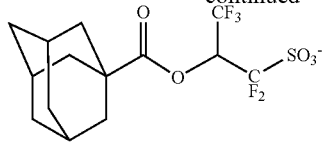
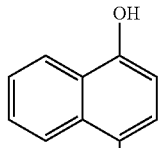
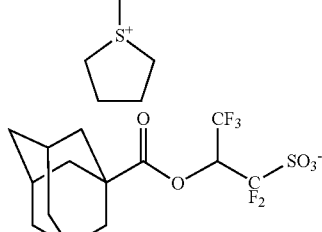
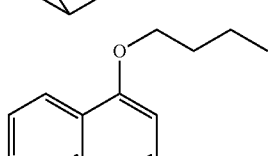
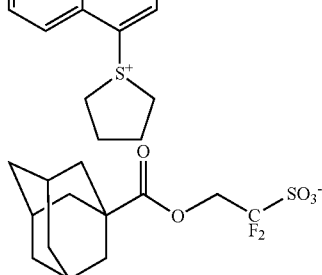
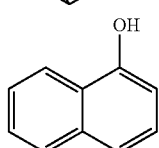
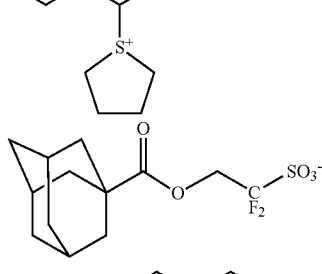
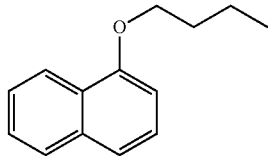
In formula (2B), $R^{fb1}$ and $R^{fb2}$ are each independently fluorine or a straight, branched or cyclic $C_1$-$C_{40}$ monovalent hydrocarbon group which may contain a heteroatom. Illustrative examples of the monovalent hydrocarbon group are as exemplified for $R^{88}$. Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: —$CF_2$—$SO_2$—$N^-$—$SO_2$—$CF_2$— to which they are attached. It is preferred to form a ring structure via a fluorinated ethylene or fluorinated propylene group.

In formula (2C), $R^{fc1}$, $R^{fc2}$ and $R^{fc3}$ are each independently fluorine or a straight, branched or cyclic $C_1$-$C_{40}$ monovalent hydrocarbon group which may contain a heteroatom. Illustrative examples of the monovalent hydrocarbon group are as exemplified for $R^{88}$. Preferably $R^{fc1}$, $R^{fc2}$ and $R^{fc3}$ are fluorine or $C_1$-$C_4$ straight fluorinated alkyl groups. Also, $R^{fc1}$ and $R^{fc2}$ may bond together to form a ring with the linkage: —$CF_2$—$SO_2$—$C^-$—$SO_2$—$CF_2$— to which they are attached. It is preferred to form a ring structure via a fluorinated ethylene or fluorinated propylene group.

In formula (2D), $R^{fd}$ is a straight, branched or cyclic $C_1$-$C_{40}$ monovalent hydrocarbon group which may contain a heteroatom. Illustrative examples of the monovalent hydrocarbon group are as exemplified for $R^{88}$.

With respect to the synthesis of the sulfonium salt having an anion of formula (2D), reference may be made to JP-A 2010-215608 and JP-A 2014-133723.

Examples of the sulfonium salt having an anion of formula (20) are shown below, but not limited thereto.

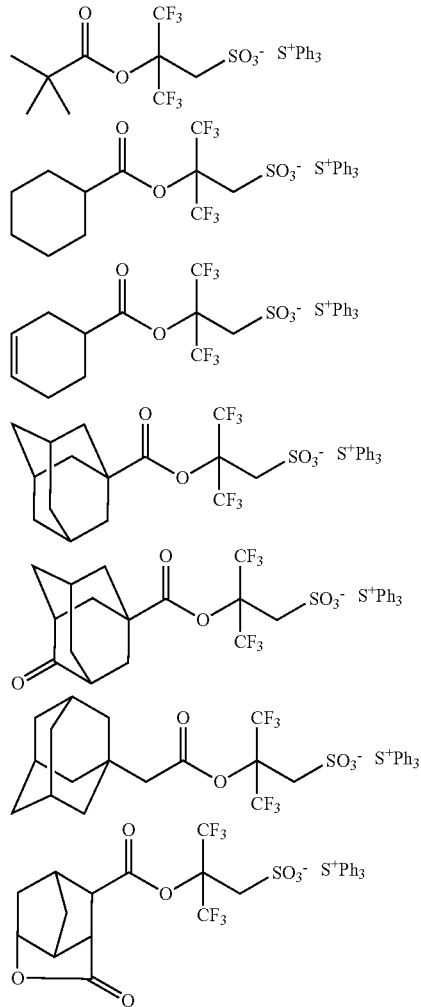
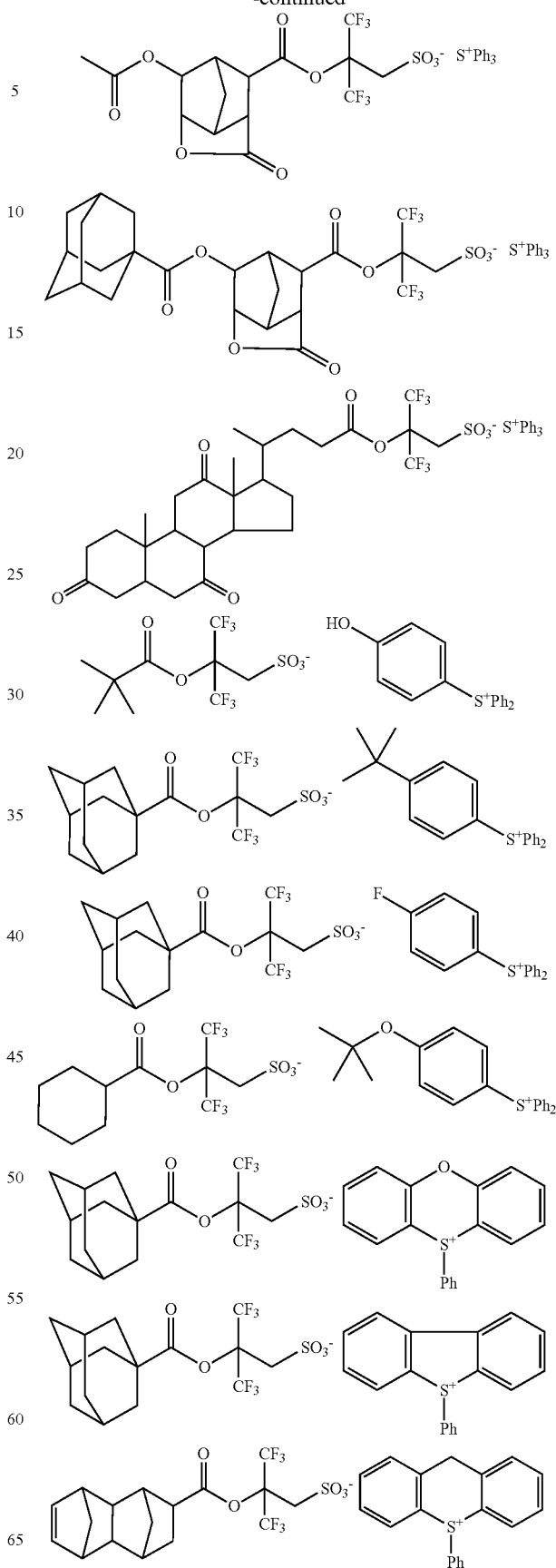

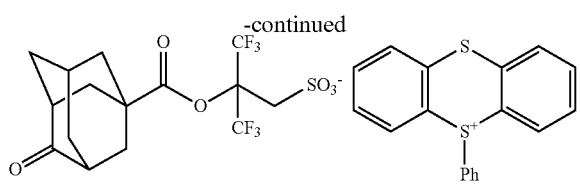

Notably, the compound having the anion of formula (20) does not have fluorine at the α-position relative to the sulfa group, but two trifluoromethyl groups at the β-position. For this reason, it has a sufficient acidity to sever the acid labile groups in the resist polymer. Thus the compound is an effective PAG.

In formula (3), $R^{300}$ and $R^{310}$ are each independently a straight, branched or cyclic $C_1$-$C_{30}$ monovalent hydrocarbon group which may contain a heteroatom. $R^{320}$ is a straight, branched or cyclic $C_1$-$C_{30}$ divalent hydrocarbon group which may contain a heteroatom. Any two or more of $R^{300}$, $R^{310}$ and $R^{320}$ may bond together to form a ring with the sulfur atom to which they are attached. $L^A$ is a single bond or a straight, branched or cyclic $C_1$-$C_{20}$ divalent hydrocarbon group which may contain a heteroatom. $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl.

Examples of the monovalent hydrocarbon group are as exemplified below for $R^{P1}$.

Suitable divalent hydrocarbon groups include straight alkane-diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; saturated cyclic divalent hydrocarbon groups such as cyclopentanediyl, cyclohexanediyl, norbornanediyl and adamantanediyl; and unsaturated cyclic divalent hydrocarbon groups such as phenylene and naphthylene. In these groups, one or more hydrogen atom may be replaced by an alkyl moiety such as methyl, ethyl, propyl, n-butyl or t-butyl; one or more hydrogen atom may be replaced by a moiety containing a heteroatom such as oxygen, sulfur, nitrogen or halogen; or a moiety containing a heteroatom such as oxygen, sulfur or nitrogen may intervene between carbon atoms, so that the group may contain a hydroxyl, cyano, carbonyl, ether bond, ester bond, sulfonic acid ester bond, carbonate bond, lactone ring, sultone ring, carboxylic anhydride or haloalkyl moiety.

Of the PAGs having formula (3), those having formula (3') are preferred.

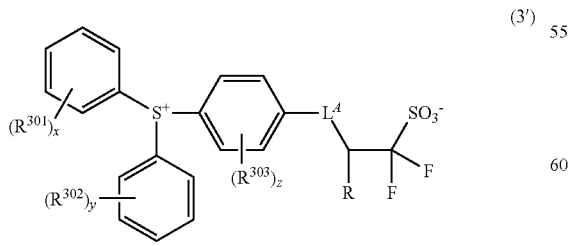

(3')

In formula (3'), $L^A$ is as defined above. R is hydrogen or trifluoromethyl, preferably trifluoromethyl. $R^{301}$, $R^{302}$ and $R^{303}$ are each independently hydrogen or a straight, branched or cyclic $C_1$-$C_{20}$ monovalent hydrocarbon group which may contain a heteroatom. Suitable monovalent hydrocarbon groups are as described above for $R^{88}$. The subscripts x and y are each independently an integer of 0 to 5, and z is an integer of 0 to 4.

Examples of the PAG having formula (3) are shown below, but not limited thereto. Notably, R is as defined above.

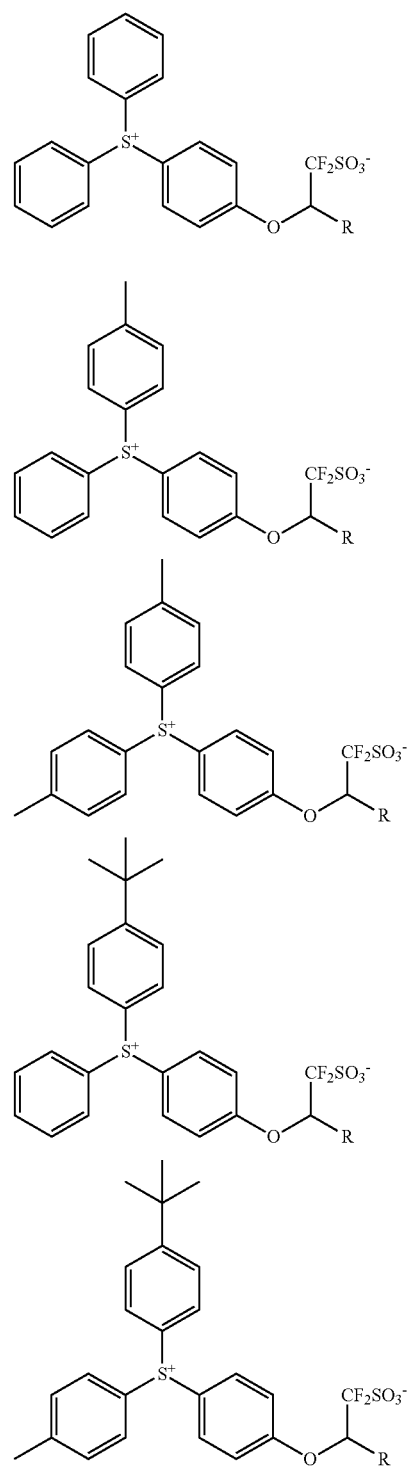

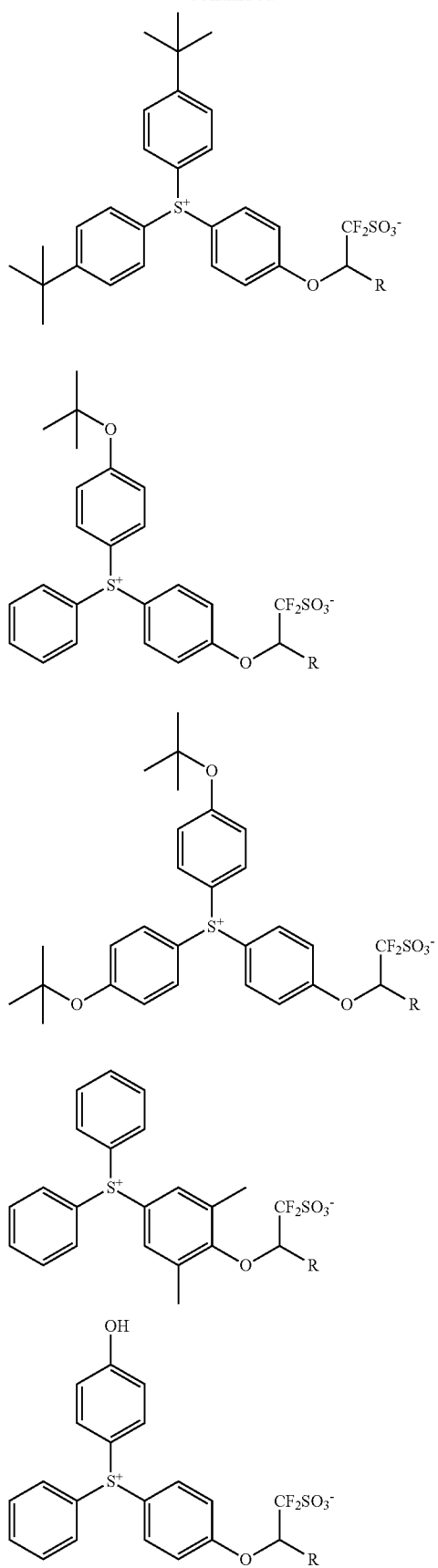
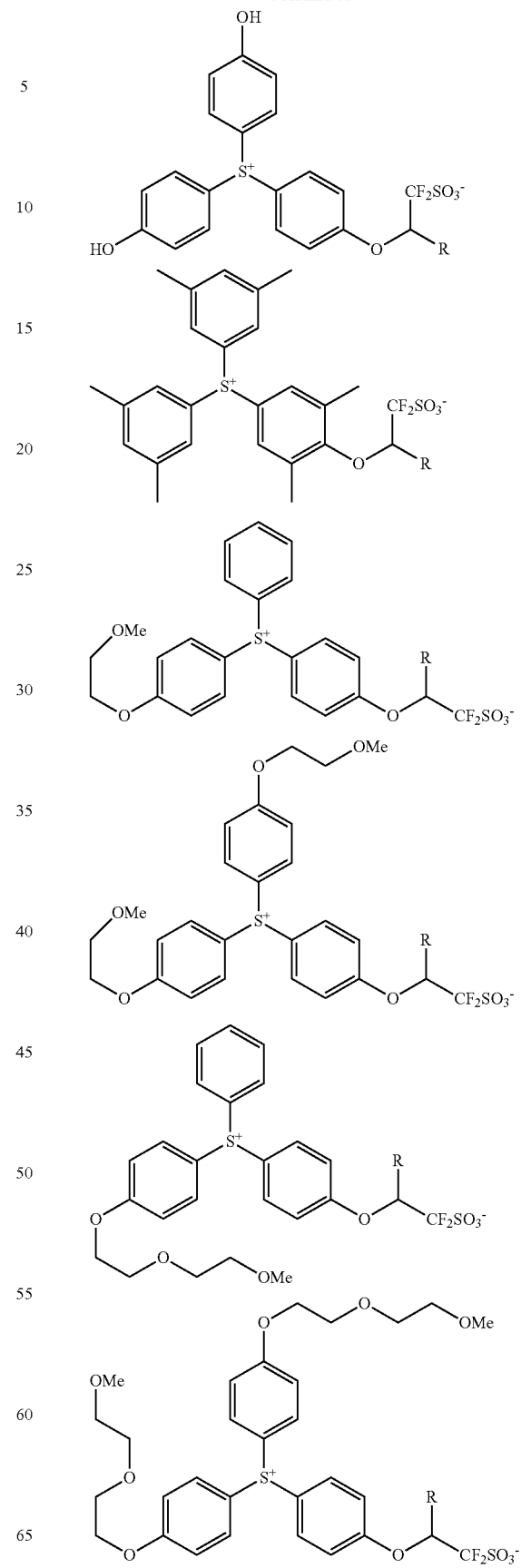

115
-continued
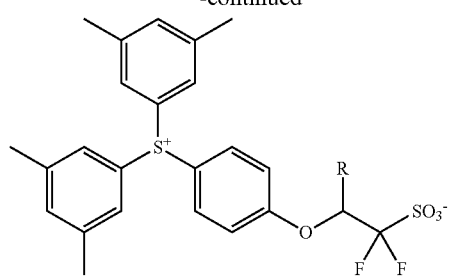
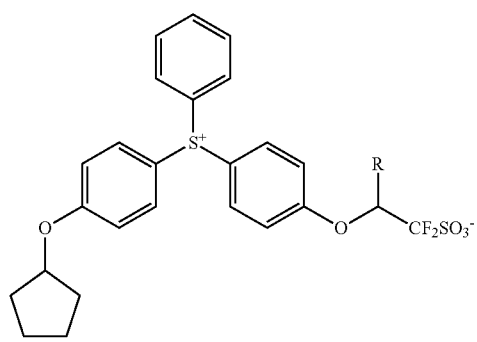
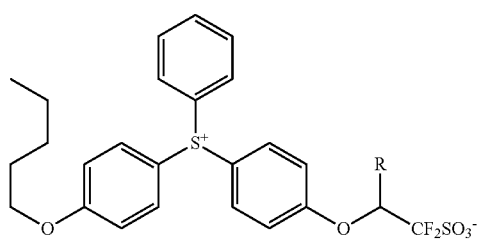
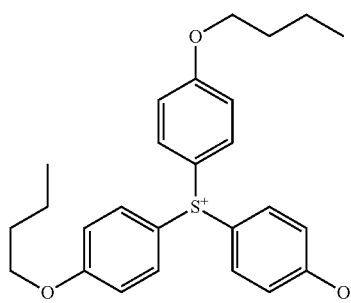
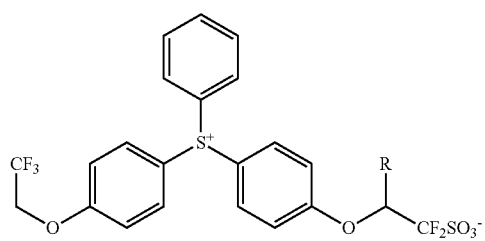
116
-continued
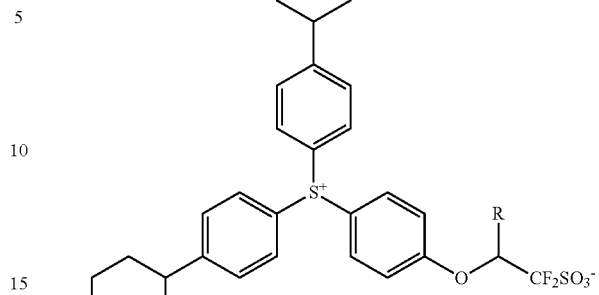
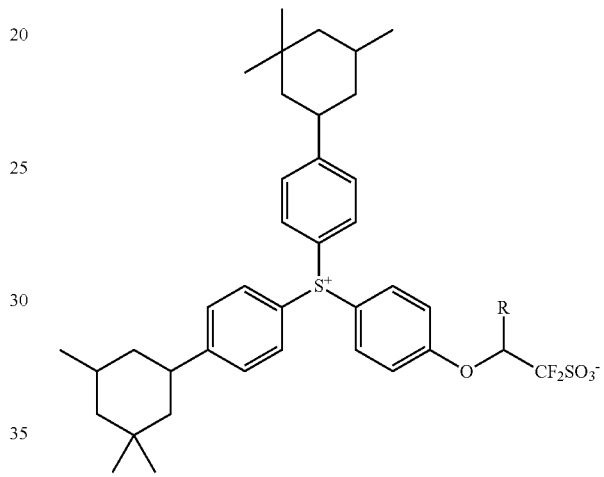
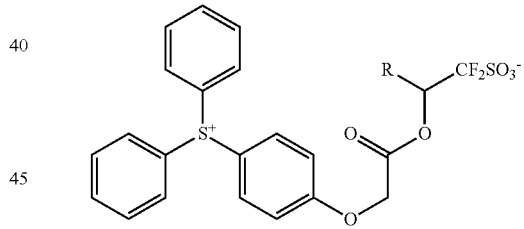
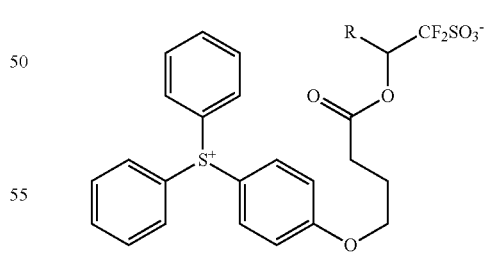
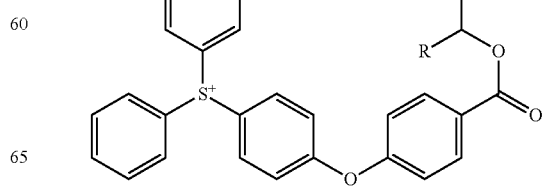

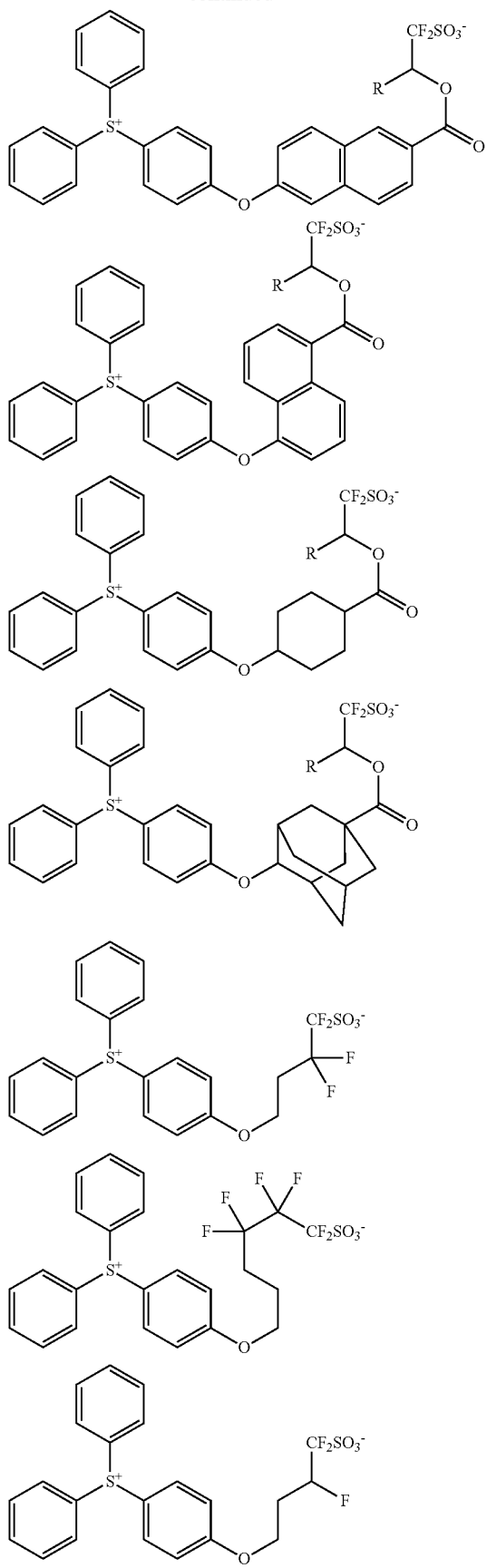
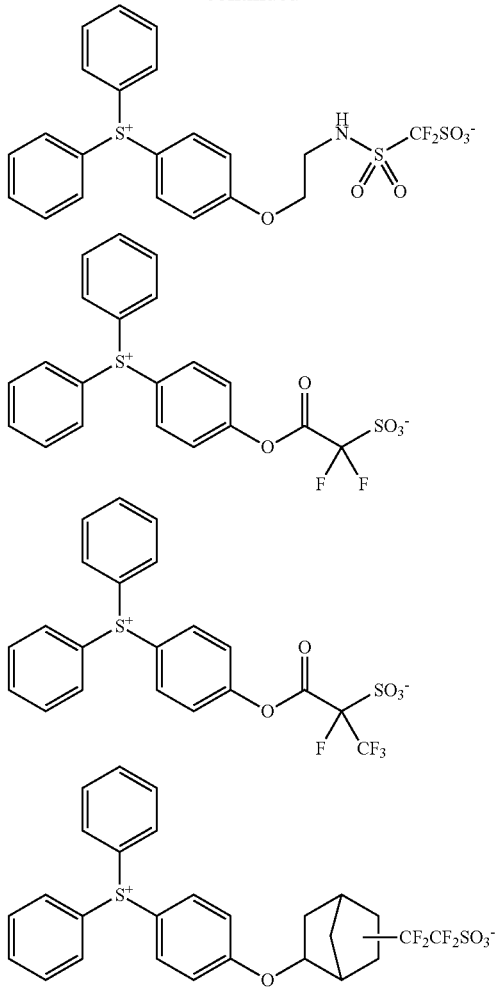

Of the foregoing PAGs, those having an anion of formula (2A') or (2D) are especially preferred because of reduced acid diffusion and high solubility in the resist solvent. Also those having an anion of formula (3') are especially preferred because of extremely reduced acid diffusion.

The PAG is preferably added in an amount of 0 to 100 parts, more preferably 0.01 to 100 parts, and even more preferably 0.1 to 80 parts by weight per 100 parts by weight of the base resin. This range maintains the transmittance of a resist film fully high and causes no or little degradation of resolution. The PAGs may be used alone or in admixture. Notably, the transmittance of a resist film may be controlled by using a PAG having a low transmittance at the exposure wavelength and adjusting the amount of the PAG added.

Also a sulfonium or iodonium salt having the following formula (H) may be used as the PAG.

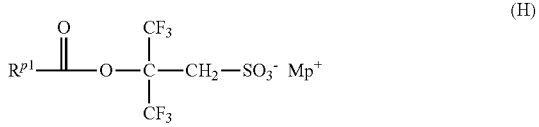

(H)

Herein $R^{p1}$ is a straight, branched or cyclic $C_1$-$C_{40}$ monovalent hydrocarbon group which may contain a heteroatom. $Mp^+$ is an onium cation having the formula (H1) or (H2):

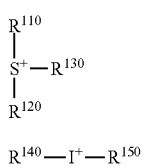

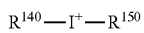

wherein $R^{110}$, $R^{120}$, $R^{130}$, $R^{140}$ and $R^{150}$ are each independently a straight, branched or cyclic $C_1$-$C_{40}$ monovalent hydrocarbon group which may contain a heteroatom, or a pair of $R^{110}$ and $R^{120}$, or $R^{140}$ and $R^{150}$ may bond together to form a ring with the sulfur or iodine atom to which they are attached.

In formula (H), suitable hydrocarbon groups $R^{p1}$ include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl and anthracenyl. In these groups, one or more hydrogen atoms may be substituted by a heteroatom such as oxygen, sulfur, nitrogen or halogen, or one or more carbon atoms may be substituted by a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety.

In formulae (H1) and (H2), suitable monovalent hydrocarbon groups represented by $R^{110}$, $R^{120}$, $R^{130}$, $R^{140}$ and $R^{150}$ are the same as exemplified above for $R^{p1}$. It is preferred that at least one of $R^{110}$, $R^{120}$ and $R^{130}$ in formula (H1) be an aromatic hydrocarbon group, and that at least one of $R^{140}$ and $R^{150}$ in formula (H2) be an aromatic hydrocarbon group.

With respect to the synthesis and examples of the sulfonium or iodonium salt having formula (H), reference may be made to JP-A 2010-215608, JP-A 2014-133723, and JP-A 2014-133725.

The anion of the compound having formula (H) does not have fluorine at α-position relative to the sulfo group, but two trifluoromethyl at β-position. For this reason, it has a sufficient acidity to sever the acid labile groups in the resist polymer. Thus the compound is an effective PAG.

The sulfonium or iodonium salt having formula (H) is preferably added in an amount of 0 to 40 parts, more preferably 0.1 to 20 parts by weight per 100 parts by weight of the base resin. Too large amounts may cause degradation of resolution or leave foreign particles after resist development or during stripping.

The positive resist composition may further comprise a dissolution regulator. Inclusion of a dissolution regulator may lead to an increased difference in dissolution rate between exposed and unexposed areas and a further improvement in resolution. Exemplary dissolution regulators are described in JP-A 2008-122932, paragraphs [0155]-[0178] (US 2008090172). The dissolution regulators may be used alone or in admixture. An appropriate amount of the dissolution regulator is 0 to 50 parts, more preferably 0 to 40 parts by weight per 100 parts by weight of the base resin. As long as the amount of the dissolution regulator is up to 50 parts by weight, there is little risk of the pattern film being slimmed to invite a drop of resolution.

To the resist composition, a quencher may be added if desired. An onium salt having a nitrogen-containing substituent group may be used as the quencher. This compound functions as a quencher in the unexposed region, but as a so-called photo-degradable base in the exposed region because it loses the quencher function in the exposed region due to neutralization thereof with the acid generated therein. Using a photo-degradable base, the contrast between exposed and unexposed regions can be further enhanced. With respect to the photo-degradable base, reference may be made to JP-A 2009-109595, JP-A 2012-046501, and JP-A 2013-209360, for example.

An appropriate amount of the photo-degradable base is 0 to 40 parts, and when used, preferably 0.1 to 40 parts, more preferably 0.1 to 20 parts by weight, per 100 parts by weight of the base resin. Too large amounts may cause degradation of resolution or leave foreign particles after resist development or during stripping.

To the resist composition, an amine compound may be added as the quencher if necessary. As used herein, the quencher is a compound capable of holding down the diffusion rate of acid when the acid generated by the PAG diffuses in the resist film. Suitable quenchers include primary, secondary and tertiary amine compounds, specifically amine compounds having a hydroxyl, ether bond, ester bond, lactone ring, cyano or sulfonic acid ester bond, as described in JP-A 2008-111103, paragraphs [0146]-[0164] (U.S. Pat. No. 7,537,880). Also included are compounds having a primary or secondary amine moiety protected as a carbamate group, as described in JP 3790649. The protected amine compounds are effective when a base labile component is present in the resist composition.

The basic compound is preferably used in an amount of 0 to 100 parts, more preferably 0.001 to 50 parts by weight per 100 parts by weight of the base resin.

Onium salts having the formulae (Ja) and (Jb) are also useful as the quencher.

Herein $R^{q1}$ is hydrogen or a straight $C_1$-$C_{40}$ or branched or cyclic $C_3$-$C_{40}$ monovalent hydrocarbon group which may contain a heteroatom. Notably, those groups wherein the hydrogen atom bonded to the carbon atom at α- and/or β-position relative to the sulfo group is replaced by fluorine or fluoroalkyl are excluded. $R^{q2}$ is hydrogen or a straight, branched or cyclic $C_1$-$C_{40}$ monovalent hydrocarbon group which may contain a heteroatom. Mq$^+$ is an onium cation having the formula (J1), (J2) or (33).

Herein $R^{410}$, $R^{420}$, $R^{430}$, $R^{440}$, $R^{450}$, $R^{460}$, $R^{470}$, $R^{480}$, and $R^{490}$ are each independently a straight, branched or cyclic $C_1$-$C_{40}$ monovalent hydrocarbon group which may contain a heteroatom, or a pair of $R^{410}$ and $R^{420}$, or $R^{460}$ and $R^{470}$ may bond together to form a ring with the sulfur or nitrogen atom to which they are attached.

Suitable groups $R^{q1}$ include hydrogen, methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl and anthracenyl. In these hydrocarbon groups, one or more hydrogen atoms may be substituted by a heteroatom such as oxygen, sulfur, nitrogen or halogen, or one or more carbon atoms may be substituted by a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety.

Examples of group $R^{q2}$ include the substituent groups exemplified above for $R^{q1}$ as well as fluorinated alkyl groups such as trifluoromethyl and trifluoroethyl, and fluorinated aryl groups such as pentafluorophenyl and 4-trifluoromethylphenyl.

Examples of the anion moiety in formulae (Ja) and (Jb) include the following structures, but are not limited thereto.

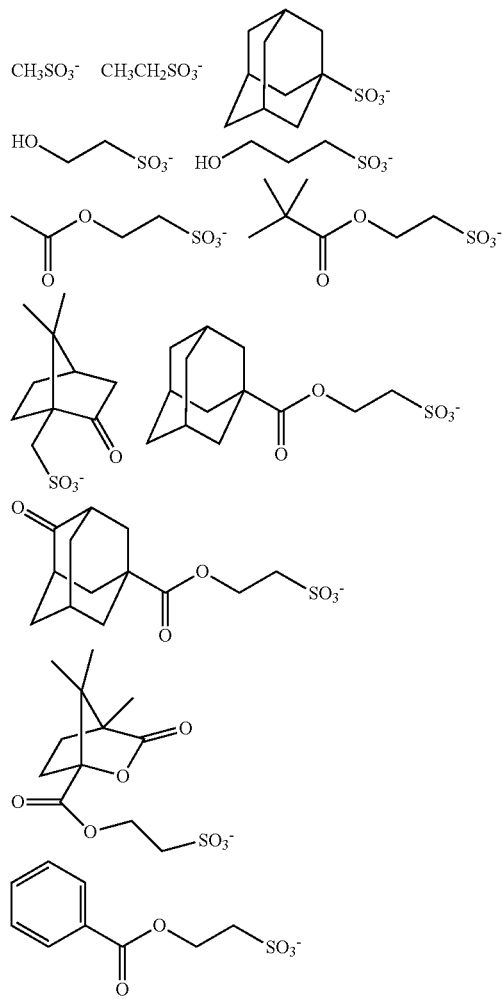
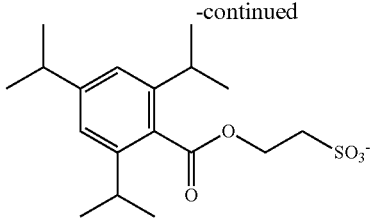
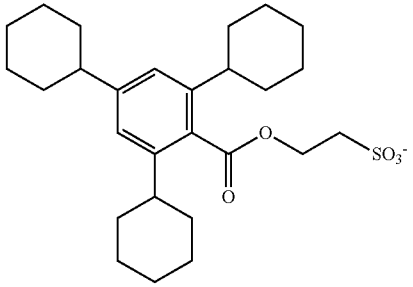
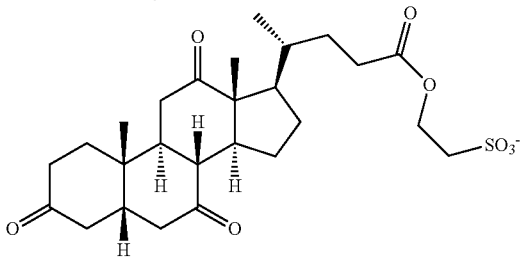
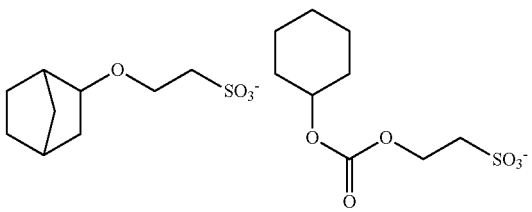
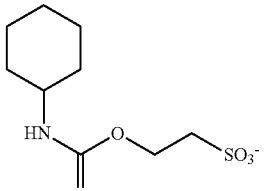
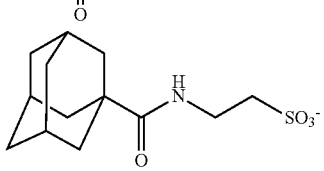
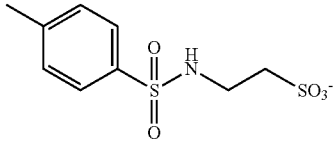
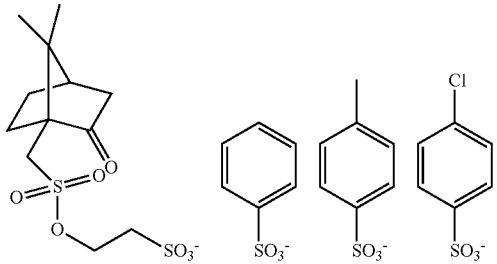

123
-continued
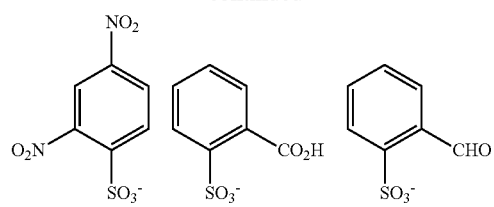
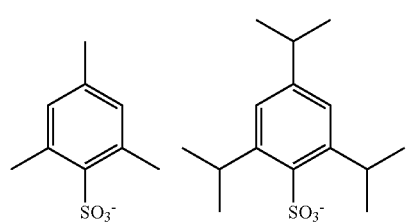
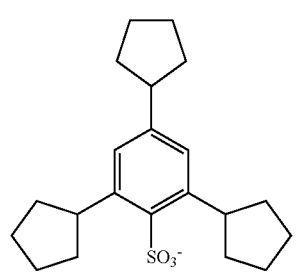
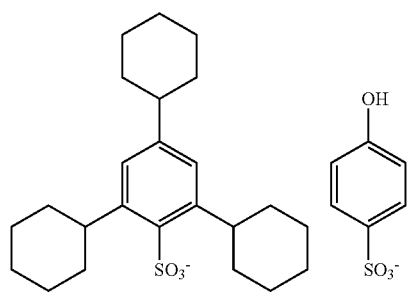
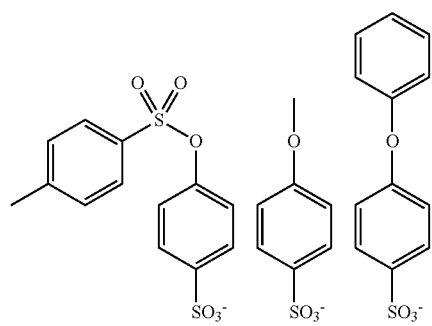
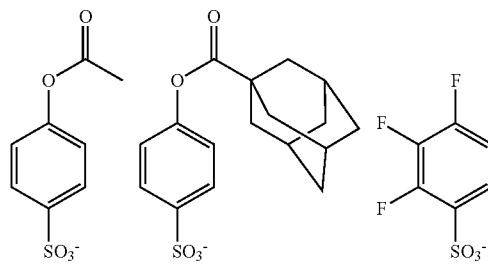
124
-continued
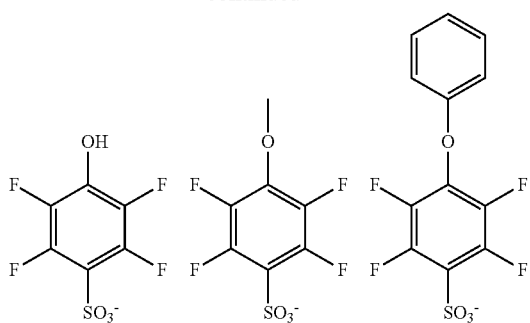
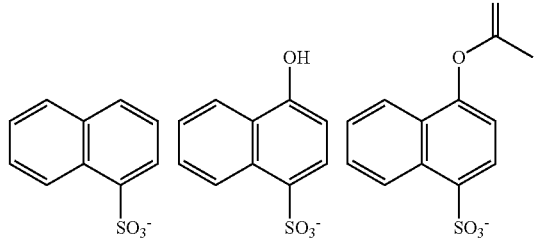
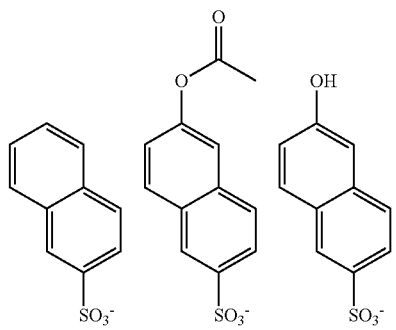
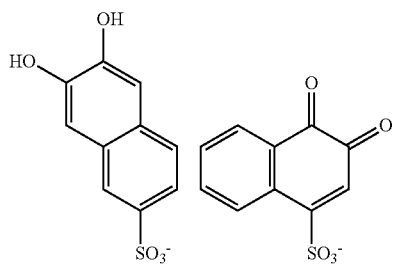
$CH_3CO_2^-$  $CH_3CH_2CO_2^-$  $CH_3CH(CH_3)CO_2^-$
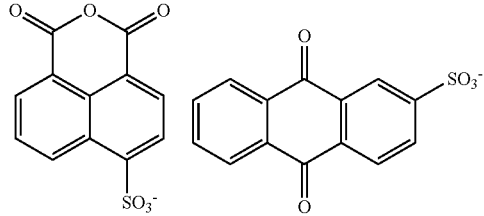
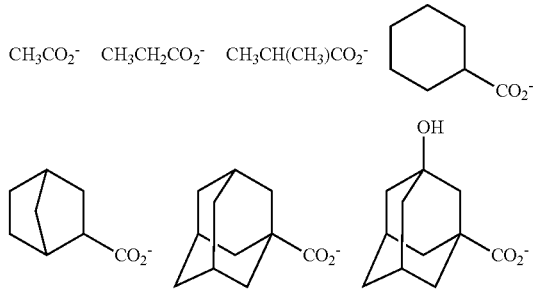

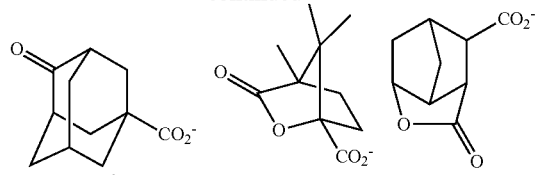
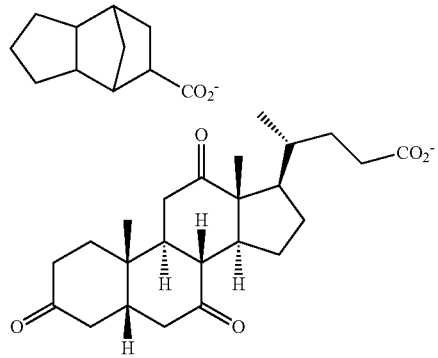
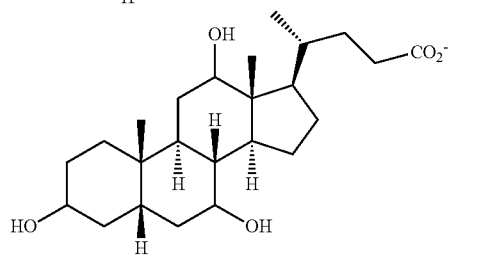
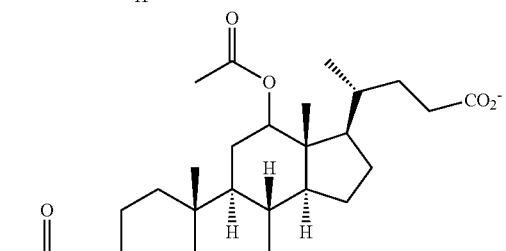
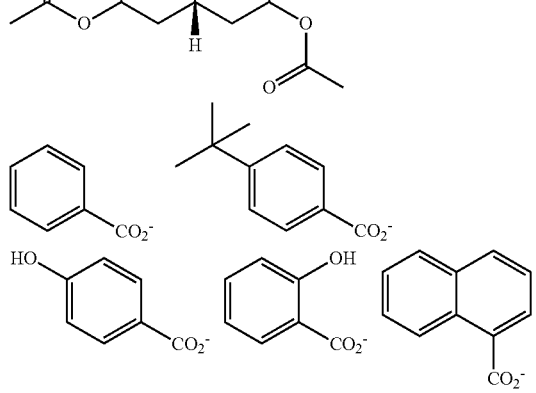
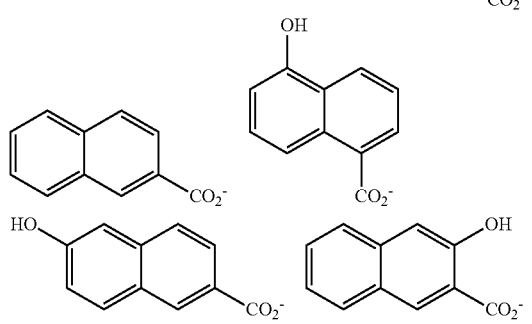
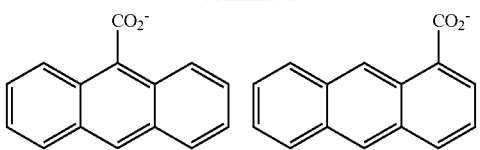
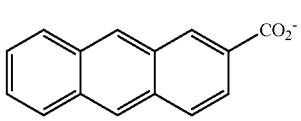
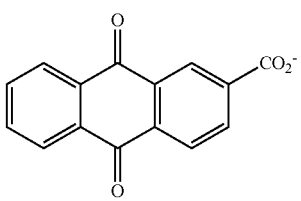
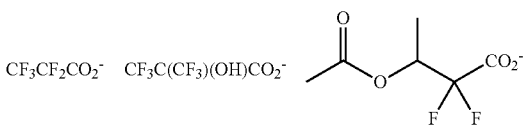
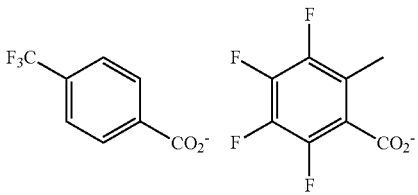
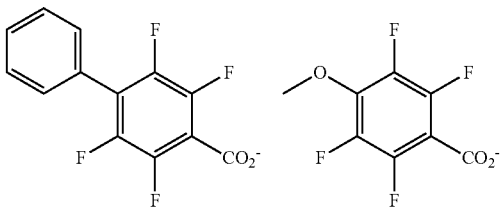
In formulae (J1), (J2) and (J3), examples of groups $R^{410}$ to $R^{490}$ include the same hydrocarbon groups as exemplified for $R^{q1}$ in formula (Ja).
Examples of the cation moiety ($Mq^+$) in formulae (Ja) and (Jb) include the following structures, but are not limited thereto.
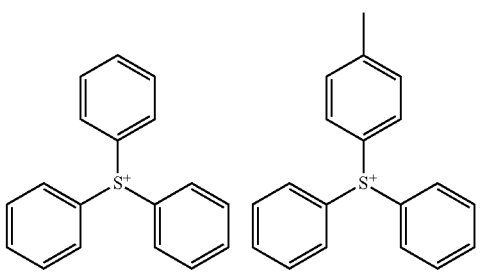

-continued
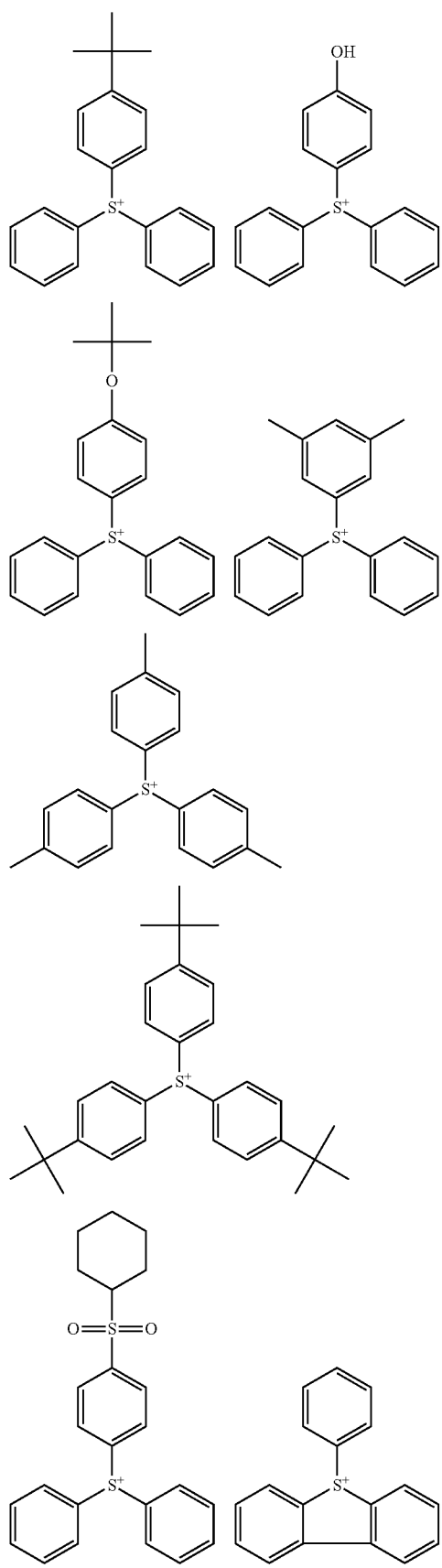
-continued
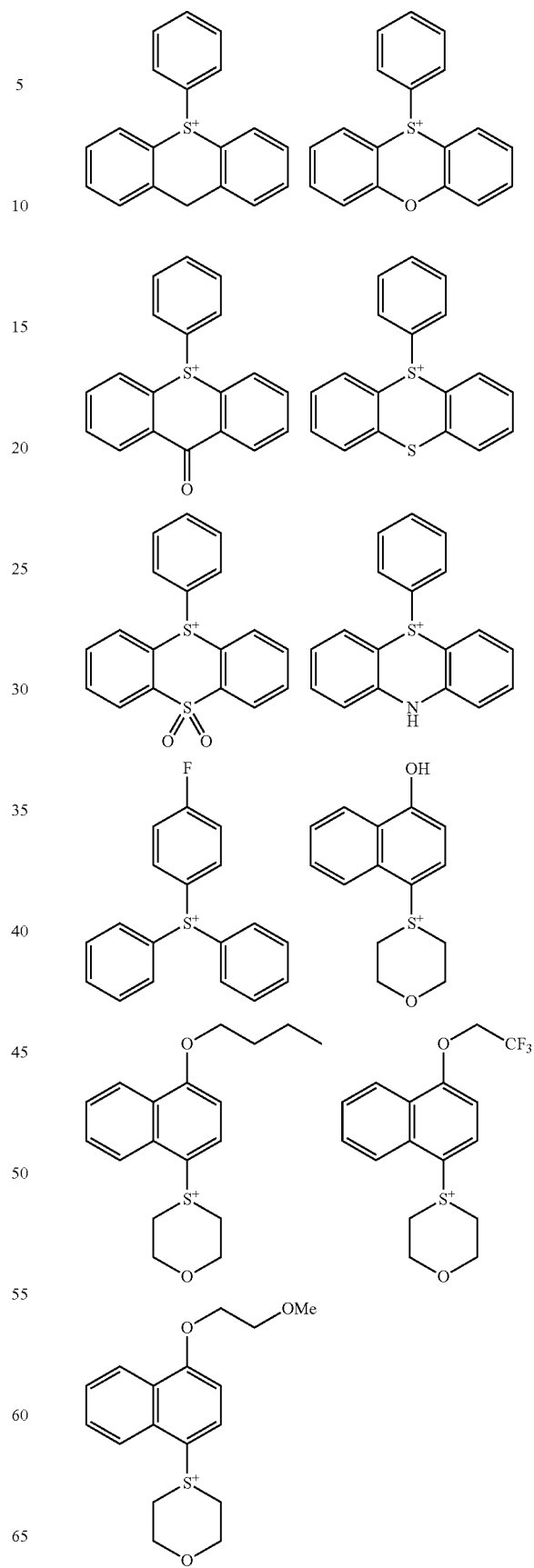

-continued

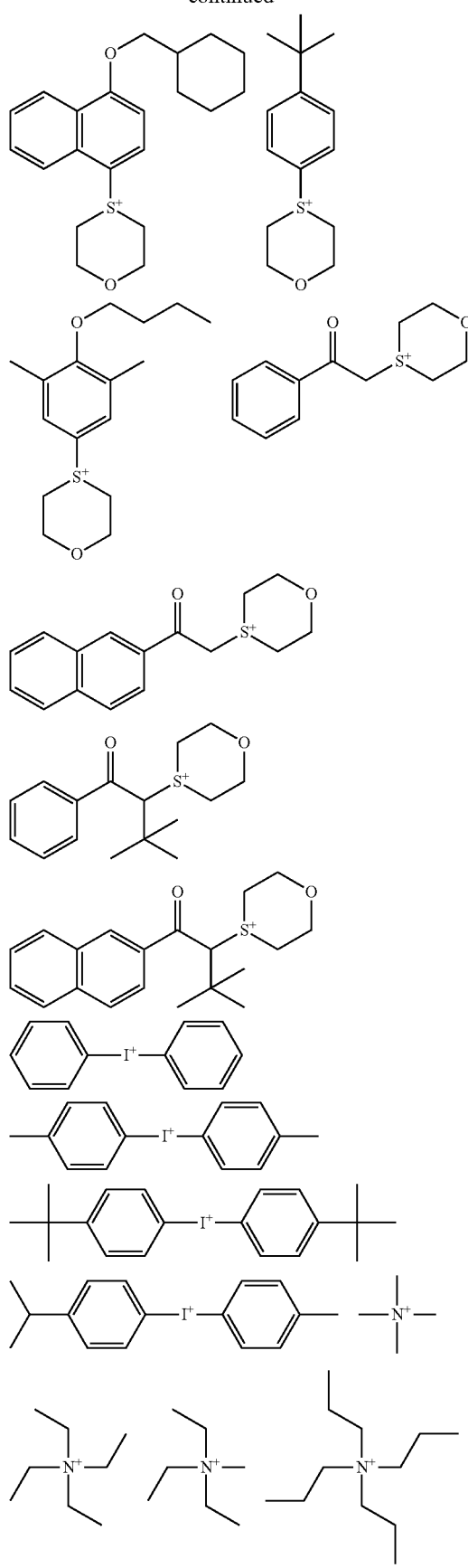

-continued

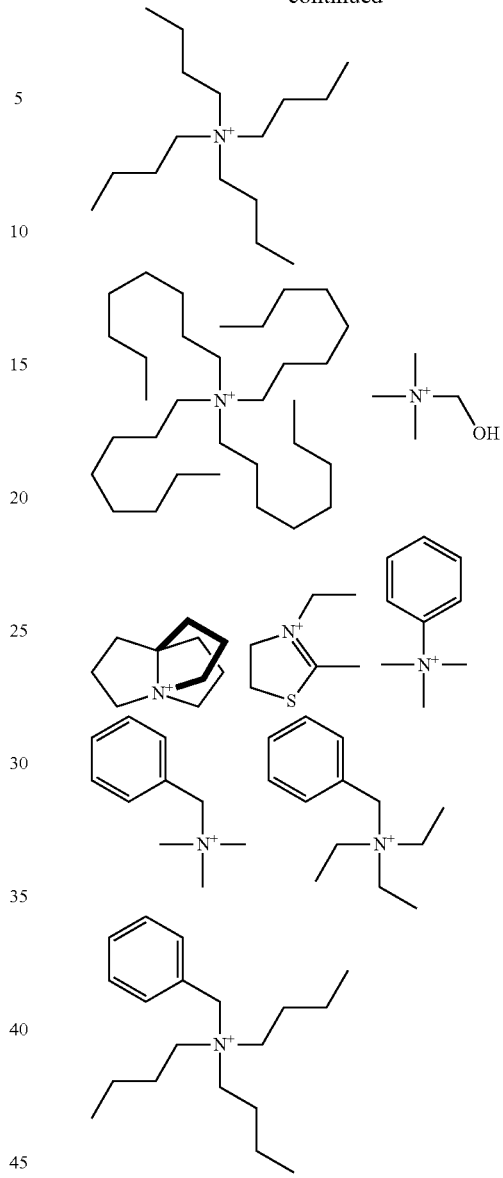

Examples of the onium salt having formula (Ja) or (Jb) include any combinations of the anion structure with the cation structure, both exemplified above. These onium salts may be readily prepared via ion exchange reaction by any well-known organic chemistry techniques. With respect to the ion exchange reaction, reference may be made to JP-A 2007-145797.

The onium salt having formula (Ja) or (Jb) functions as the quencher because the counter anion of the onium salt is a conjugated base of weak acid. As used herein, the weak acid indicates an acidity insufficient to deprotect an acid labile group from an acid labile group-containing unit in the base resin. The onium salt having formula (Ja) or (Jb) functions as a quencher when used in combination with an onium salt type PAG having a conjugated base of a strong acid, typically a sulfonic acid which is fluorinated at α-position as the counter anion. In a system using a mixture of an onium salt capable of generating a strong acid (e.g., α-position fluorinated sulfonic acid) and an onium salt capable of generating a weak acid (e.g., α-position nonfluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If a PAG capable of generating a strong acid is an onium salt, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

An appropriate amount of the onium salt having formula (Ja) or (Jb) added is 0 to 40 parts by weight, and when used, 0.1 to 40 parts, more preferably 0.1 to 20 parts by weight per 100 parts by weight of the base resin. An excessive amount may bring about a drop of resolution, and leave foreign particles after resist development or during separation.

To the positive resist composition, a surfactant may be added. Inclusion of a surfactant may facilitate or control the coating operation of the resist composition. Exemplary surfactants are described in JP-A 2008-111103, paragraphs [0165]-[0166]. An appropriate amount of the surfactant added is 0 to 10 parts, preferably 0.0001 to 5 parts by weight per 100 parts by weight of the base resin.

To the positive resist composition, an acetylene alcohol may be added. Exemplary acetylene alcohols are described in JP-A 2008-122932, paragraphs [0179]-[0182]. An appropriate amount of the acetylene alcohol added is 0 to 2%, preferably 0.02 to 1% by weight of the resist composition. As long as the amount of acetylene alcohol is 2 wt % or less, the resolution of the resist composition may not be adversely affected.

Also useful are quenchers of polymer type as described in JP-A 2008-239918. The polymeric quencher segregates at the resist surface after coating and thus enhances the rectangularity of resist pattern. When a protective film is applied as is often the case in the immersion lithography, the polymeric quencher is also effective for preventing any film thickness loss of resist pattern or rounding of pattern top. When the polymeric quencher is added, its amount is arbitrary as long as the benefits of the invention are not impaired.

The inventive polymer is advantageously used as a base resin in a positive resist composition. Specifically, the polymer is used as a base resin and combined with an organic solvent and optionally a PAG, dissolution regulator, basic compound, surfactant or the like to formulate a positive resist composition. This positive resist composition has a very high sensitivity in that the dissolution rate in developer of the polymer in exposed areas is accelerated by catalytic reaction. In addition, the resist film has a high dissolution contrast, resolution, exposure latitude, and process adaptability, and provides a good pattern profile after exposure, yet better etch resistance, and minimal proximity bias because of restrained acid diffusion. By virtue of these advantages, the composition is fully useful in commercial application and suited as a pattern-forming material for the fabrication of VLSIs or photomasks. Particularly when a PAG is incorporated to formulate a chemically amplified positive resist composition capable of utilizing acid catalyzed reaction, the composition has a higher sensitivity and is further improved in the properties described above.

Process

The positive resist composition, typically chemically amplified positive resist composition is used in the fabrication of various integrated circuits. Pattern formation using the resist composition may be performed by well-known lithography processes. The process generally involves coating, prebake, exposure, and development. If necessary, any additional steps may be added.

The positive resist composition is first applied onto a substrate on which an integrated circuit is to be formed (e.g., Si, $SiO_2$, SiN, SiON, TiN, WSi, BPSG, SDG, or organic antireflective coating) or a substrate on which a mask circuit is to be formed (e.g., Cr, CrO, CrON, MoSi, or $SiO_2$) by a suitable coating technique such as spin coating, roll coating, flow coating, dip coating, spray coating or doctor coating. The coating is prebaked on a hot plate at a temperature of 60 to 150° C. for 10 seconds to 30 minutes, preferably 80 to 120° C. for 30 seconds to 20 minutes. The resulting resist film is generally 0.1 to 2.0 µm thick.

The resist film is then exposed to a desired pattern of high-energy radiation such as UV, deep-UV, x-ray, excimer laser light, γ-ray, synchrotron radiation, EUV (soft x-ray) or EB, directly or through a mask. The exposure dose is preferably about 1 to 200 $mJ/cm^2$, more preferably about 10 to 100 $mJ/cm^2$, or 0.1 to 100 $\mu C/cm^2$, more preferably 0.5 to 50 $\mu C/cm^2$. The resist film is further baked (PEB) on a hot plate at 60 to 150° C. for 10 seconds to 30 minutes, preferably 80 to 120° C. for 30 seconds to 20 minutes.

Thereafter the resist film is developed in a developer in the form of an aqueous base solution for 3 seconds to 3 minutes, preferably 5 seconds to 2 minutes by conventional techniques such as dip, puddle or spray techniques. Suitable developers are 0.1 to 10 wt %, preferably 2 to 10 wt %, more preferably 2 to 5 wt % aqueous solutions of tetramethylammonium hydroxide (TMAH), tetraethylammonium hydroxide (TEAH), tetrapropylammonium hydroxide (TPAH) and tetrabutylammonium hydroxide (TBAH). The resist film in the exposed area is dissolved in the developer whereas the resist film in the unexposed area is not dissolved. In this way, the desired positive pattern is formed on the substrate. It is appreciated that the resist composition of the invention is best suited for micro-patterning using such high-energy radiation as EB, EUV (soft x-ray), x-ray, γ-ray and synchrotron radiation among others.

Although TMAH aqueous solution is generally used as the developer, TEAH, TPAH and TBAH having a longer alkyl chain are effective in inhibiting the resist film from being swollen during development and thus preventing pattern collapse. JP 3429592 describes an example using an aqueous TBAH solution for the development of a polymer comprising recurring units having an alicyclic structure such as adamantane methacrylate and recurring units having an acid labile group such as t-butyl methacrylate, the polymer being water repellent due to the lack of hydrophilic groups.

The TMAH developer is most often used as 2.38 wt % aqueous solution, which corresponds to 0.26N. The TEAH, TPAH, and TBAH aqueous solutions should preferably have an equivalent normality. The concentration of TEAH, TPAH, and TBAH that corresponds to 0.26N is 3.84 wt %, 5.31 wt %, and 6.78 wt %, respectively.

When a pattern with a line size of 32 nm or less is resolved by the EB and EUV lithography, there arises a phenomenon that lines become wavy, lines merge together, and merged lines collapse. It is believed that this phenomenon occurs because lines are swollen in the developer and the thus expanded lines merge together. Since the swollen lines containing liquid developer are as soft as sponge, they readily collapse under the stress of rinsing. For this reason, the developer using a long-chain alkyl developing agent is effective for preventing film swell and hence, pattern collapse.

EXAMPLE

Examples and Comparative Examples are given below for further illustrating the invention, but they should not be construed as limiting the invention thereto. All parts (pbw) are by weight. Mw is a weight average molecular weight as measured versus polystyrene standards by GPC using tetrahydrofuran (THF) solvent. IR spectroscopy was measured by NICOLET 6700 (Thermo Fisher Scientific Inc.) and $^1$H-NMR spectroscopy by ECA-600 (JEOL Ltd.).

Synthesis of Monomers

Example 1-1

Example 1-1-1

Synthesis of Alcohol 1

In nitrogen atmosphere, a solution of Chloride 1 (203.1 g) and 1,2-dibromoethane (1.2 g) in THF (183 g) was added dropwise to a suspension of magnesium (28.1 g) in THF (30 g) at a temperature of 65-80° C. Stirring was continued at the temperature for 12 hours, obtaining Grignard reagent 1. The reaction solution was cooled to room temperature, to which a solution of ethyl formate (37.0 g) in THF (240 g) was added dropwise at a temperature of 20-40° C. Stirring was continued at the temperature for 3 hours. A 15 wt % ammonium chloride aqueous solution (1,300 g) was added dropwise to the reaction solution to quench the reaction. This was followed by ordinary aqueous workup and recrystallization from an ethyl acetate/n-hexane mixture, obtaining Alcohol 1 (138 g, yield 84%). It was analyzed by $^1$H-NMR spectroscopy.

$^1$H-NMR (600 MHz in DMSO-d$_6$):
δ=7.24 (4H, d), 6.89 (4H, d), 5.73 (1H, d), 5.61 (1H, d), 1.24 (18H, s) ppm

Example 1-1-2

Synthesis of Monomer 1

Alcohol 1 (137 g), triethylamine (59.4 g) and 4-(dimethylamino)pyridine (1.5 g) were added to toluene (200 g). To the solution which was heated at an internal temperature of 40-50° C., Esterifying agent 1 (74.3 g) was added dropwise. The solution was stirred at 50° C. for 2 hours. The reaction solution was ice cooled, to which a saturated sodium hydrogencarbonate aqueous solution was added dropwise to quench the reaction. This was followed by ordinary aqueous workup and recrystallization from an ethyl acetate/methanol mixture, obtaining Monomer 1 (146 g, yield 87%). It was analyzed by IR and $^1$H-NMR spectroscopy.

IR (D-ATR); ν=2976, 2930, 1709, 1637, 1605, 1505, 1365, 1290, 1238, 1174, 1157, 1107, 1014, 897, 859 cm$^{-1}$
$^1$H-NMR (600 MHz in DMSO-d$_6$):
δ=7.28 (4H, d), 6.93 (4H, d), 6.80 (1H, s), 6.17 (1H, s), 5.71 (1H, m), 1.92 (3H, s), 1.26 (18H, s) ppm Example 1-2

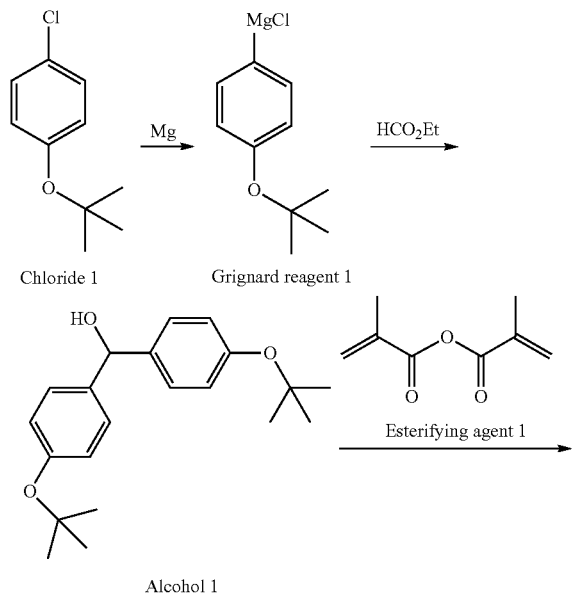

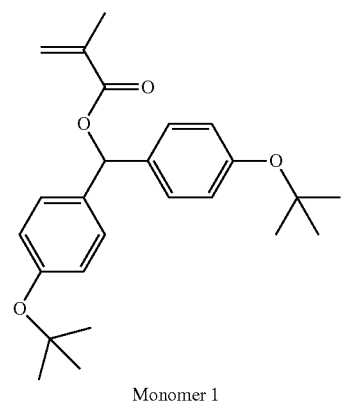

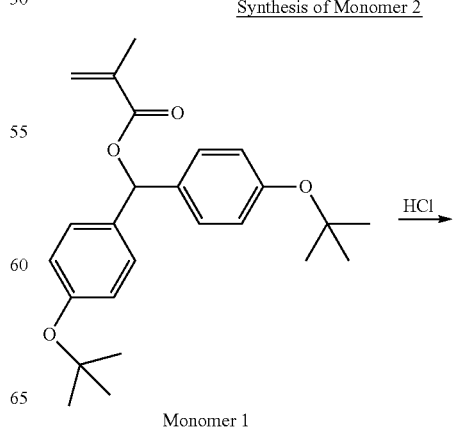

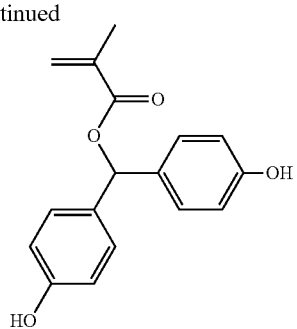

Monomer 2

In nitrogen atmosphere, 10 wt % hydrochloric acid (6.0 g) was added dropwise to a solution of Monomer 1 (10.0 g) in acetone (40 g) at a temperature of 20-30° C. Stirring was continued at the temperature for 4 hours. Ethyl acetate (50 g) was added to the reaction solution. This was followed by ordinary aqueous workup and recrystallization from an ethyl acetate/n-hexane mixture, obtaining Monomer 2 (3.3 g, yield 46%).

Example 1-3

Synthesis of Monomer 3

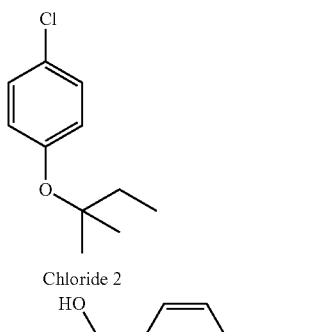

Chloride 2

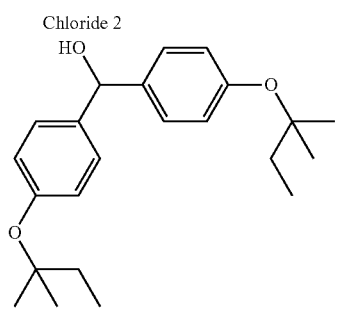

Alcohol 2

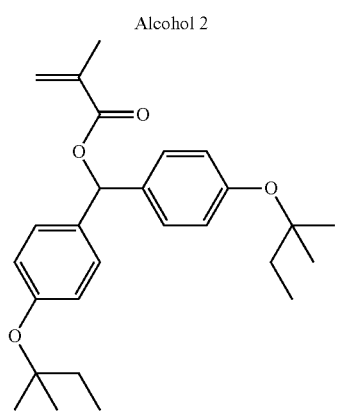

Monomer 3

Example 1-3-1

Synthesis of Alcohol 2

Alcohol 2 was obtained by the same procedure as in Example 1-1-1 aside from using Chloride 2 instead of Chloride 1. Yield 81%.

Example 1-3-2

Synthesis of Monomer 3

Monomer 3 was obtained by the same procedure as in Example 1-1-2 aside from using Alcohol 2 instead of Alcohol 1. Yield 86%.

Example 1-4

Synthesis of Monomer 4

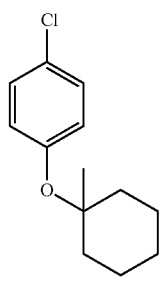

Chloride 3

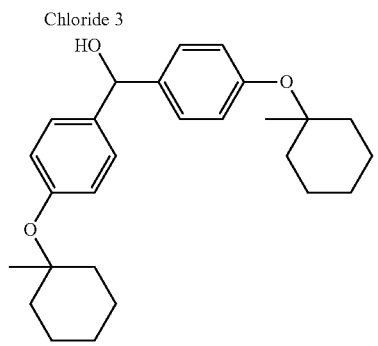

Alcohol 3

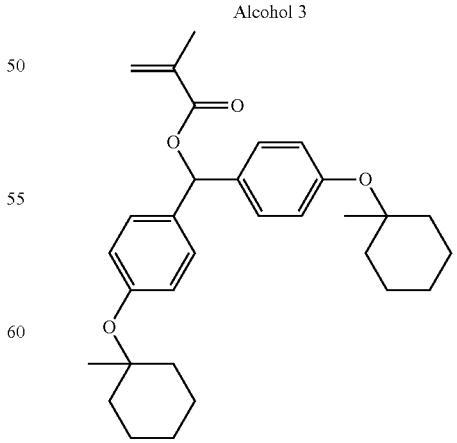

Monomer 4

Example 1-4-1

Synthesis of Alcohol 3

Alcohol 3 was obtained by the same procedure as in Example 1-1-1 aside from using Chloride 3 instead of Chloride 1. Yield 81%. It was analyzed by $^1$H-NMR spectroscopy.

$^1$H-NMR (600 MHz in DMSO-$d_6$):

δ=7.22 (4H, app d), 6.89 (4H, app d), 5.72 (1H, d), 5.59 (1H, d), 1.59-1.78 (8H, m), 1.36-1.47 (10H, m), 1.25-1.33 (2H, m), 1.17 (6H, s) ppm

Example 1-4-2

Synthesis of Monomer 4

Monomer 4 was obtained by the same procedure as in Example 1-1-2 aside from using Alcohol 3 instead of Alcohol 1. Yield 80%. It was analyzed by IR and $^1$H-NMR spectroscopy.

IR (D-ATR): ν=2932, 2859, 1719, 1637, 1607, 1506, 1447, 1375, 1290, 1227, 1153, 1106, 1011, 964, 895, 848 cm$^{-1}$ $^1$H-NMR (600 MHz in DMSO-$d_6$):

δ=7.27 (4H, d), 6.93 (4H, d), 6.79 (1H, s), 6.17 (1H, s), 5.73 (1H, s), 1.91 (3H, s), 1.73-1.79 (4H, m), 1.57-1.64 (4H, m), 1.36-1.46 (10H, m), 1.25-1.32 (2H, m), 1.18 (6H, s) ppm

Example 1-5

Synthesis of Monomer 5

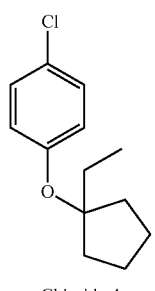

Chloride 4

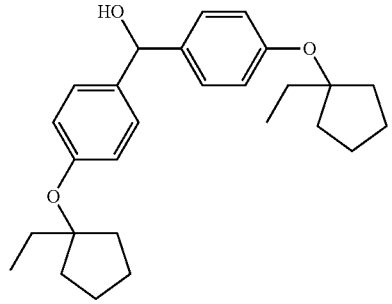

Alcohol 4

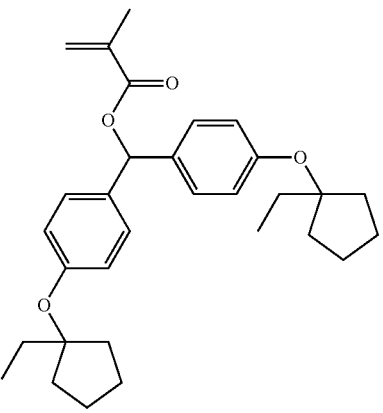

Monomer 5

Example 1-5-1

Synthesis of Alcohol 4

Alcohol 4 was obtained by the same procedure as in Example 1-1-1 aside from using Chloride 4 instead of Chloride 1. Yield 82%.

Example 1-5-2

Synthesis of Monomer 5

Monomer 5 was obtained by the same procedure as in Example 1-1-2 aside from using Alcohol 4 instead of Alcohol 1. Yield 85%.

Example 1-6

Synthesis of Monomer 6

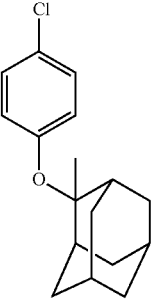

Chloride 5

139
-continued

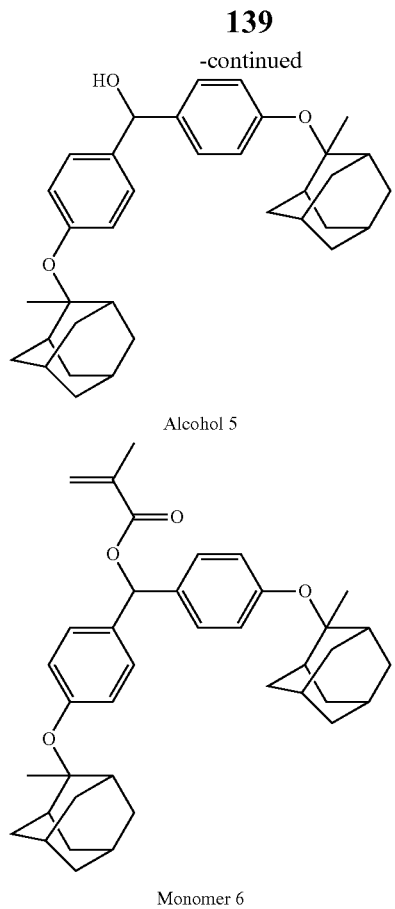

Alcohol 5

Monomer 6

Example 1-6-1

Synthesis of Alcohol 5

Alcohol 5 was obtained by the same procedure as in Example 1-1-1 aside from using Chloride 5 instead of Chloride 1. Yield 87%.

Example 1-6-2

Synthesis of Monomer 6

Monomer 6 was obtained by the same procedure as in Example 1-1-2 aside from using Alcohol 5 instead of Alcohol 1. Yield 79%.

Example 1-7

Synthesis of Monomer 7

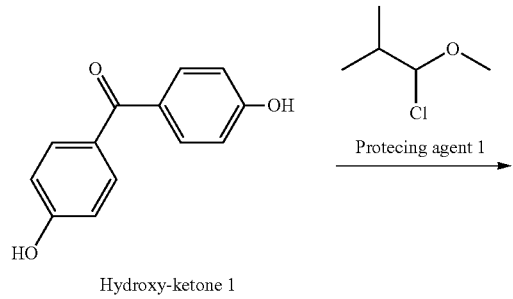

Hydroxy-ketone 1

140
-continued

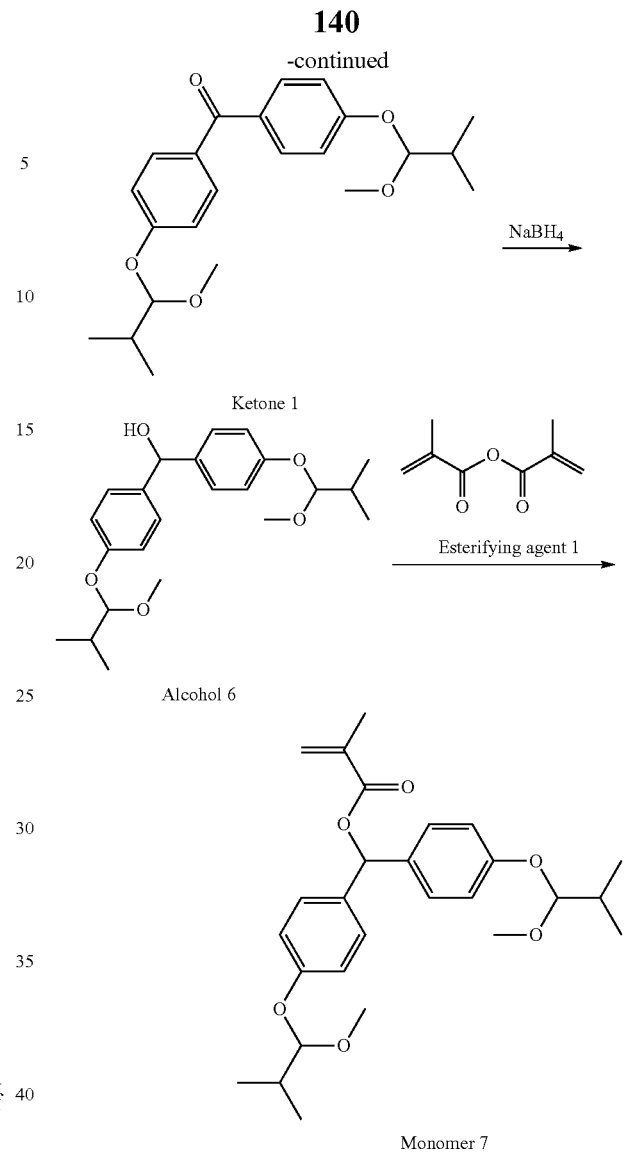

Ketone 1

Alcohol 6

Monomer 7

Example 1-7-1

Synthesis of Ketone 1

In nitrogen atmosphere, Hydroxy-ketone 1 (10.0 g) and triethylamine (13.2 g) were mixed with acetonitrile (50 ml). Below 20° C., Protecting agent 1 (13.7 g) was added dropwise. Stirring was continued at room temperature for 4 hours. Water (30 ml) was added to the reaction solution to quench the reaction. This was followed by ordinary aqueous workup. The product was purified by silica gel column chromatography, obtaining Ketone 1 (16.6 g, yield 92%).

Example 1-7-2

Synthesis of Alcohol 6

A solution of Ketone 1 (16.0 g) in THF (15 g) was added dropwise to a suspension of sodium borohydride (1.3 g) in water (10 g) and methanol (30 g) at a temperature of 20-40° C. Stirring was continued at 40° C. for 2 hours. This was followed by ordinary aqueous workup. The product was purified by silica gel column chromatography, obtaining Alcohol 6 (13.7 g, yield 85%). It was analyzed by $^1$H-NMR spectroscopy.

$^1$H-NMR (600 MHz in DMSO-$d_6$)%

δ=7.24 (4H, app d), 6.95 (4H, app d), 5.69 (1H, d), 5.59 (1H, d), 4.90 (2H, d), 3.24 (6H, s), 2.00 (2H, sept), 0.91 (12H, t) ppm Example 1-7-3

Synthesis of Monomer 7

Monomer 7 was obtained by the same procedure as in Example 1-1-2 aside from using Alcohol 6 instead of Alcohol 1. Yield 86%. It was analyzed by IR and $^1$H-NMR spectroscopy.

IR (D-ATR): ν=2962, 2929, 2875, 1717, 1637, 1610, 1509, 1471, 1391, 1291, 1239, 1206, 1154, 1096, 1004, 952, 901, 831 cm$^{-1}$ $^1$H-NMR (600 MHz in DMSO-$d_6$):

δ=7.31 (4H, app d), 7.00 (4H, app d), 6.77 (1H, s), 6.17 (1H, s), 5.73 (1H, m), 4.94 (2H, d), 3.24 (6H, d), 2.01 (2H, sept), 1.92 (3H, s), 0.93 (12H, t) ppm Example 1-8

Synthesis of Monomer 8

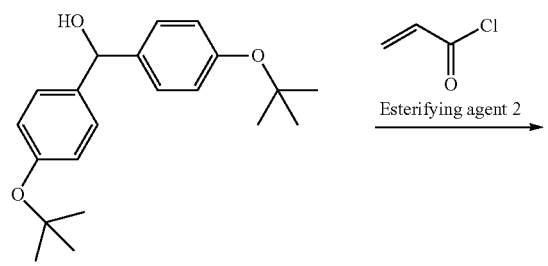

Monomer 8 was obtained by the same procedure as in Example 1-1-2 aside from using Esterifying agent 2 instead of Esterifying agent 1. Yield 81%.

Example 1-9

Synthesis of Monomer 9

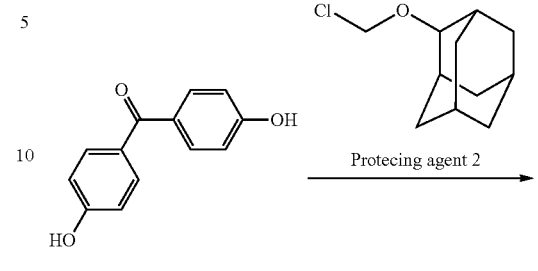

Example 1-9-1

Synthesis of Ketone 2

In nitrogen atmosphere, Hydroxy-ketone 1 (21.4 g) and triethylamine (10.1 g) were mixed with acetonitrile (200 ml). Below 20° C., Protecting agent 2 (10.0 g) was added dropwise. Stirring was continued at room temperature for 4 hours. Water (100 ml) was added to the reaction solution to quench the reaction. This was followed by ordinary workup. The product was purified by silica gel column chromatography, obtaining Ketone 2 (23.8 g, yield 63%).

Example 1-9-2

Synthesis of Alcohol 7

A solution of Ketone 2 (18.0 g) in THF (30 g) was added dropwise to a suspension of sodium borohydride (1.1 g) in water (10 g) and methanol (30 g) at a temperature of 20-40° C. Stirring was continued at 40° C. for 2 hours. This was followed by ordinary aqueous workup. The product was purified by silica gel column chromatography, obtaining Alcohol 7 (15.8 g, yield 83%).

Example 1-9-3

Synthesis of Monomer 9

Monomer 9 was obtained by the same procedure as in Example 1-1-2 aside from using Alcohol 7 instead of Alcohol 1. Yield 81%.

Example 1-10

Synthesis of Monomer 10

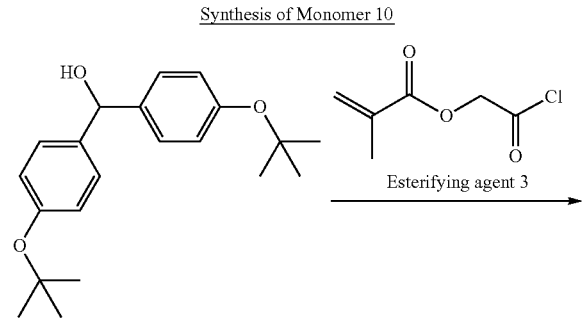

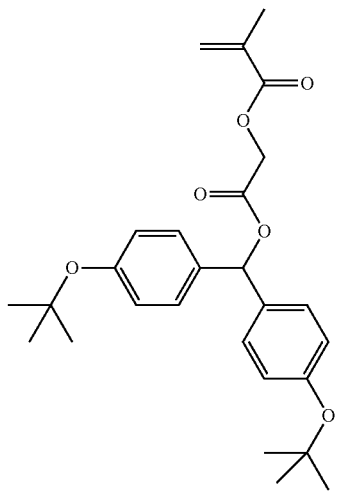

Monomer 10

Monomer 10 was obtained by the same procedure as in Example 1-1-2 aside from using Esterifying agent 3 instead of Esterifying agent 1. Yield 76%.

Example 1-11

Synthesis of Monomer 11

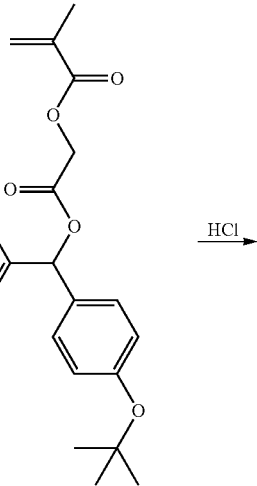

Monomer 10

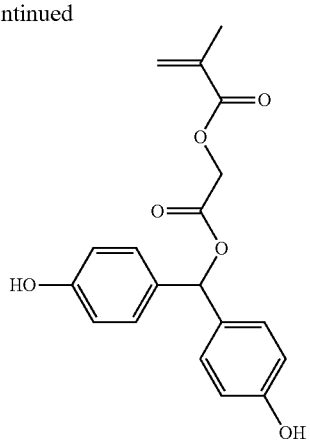

Monomer 11

Monomer 11 was obtained by the same procedure as in Example 1-2 aside from using Monomer 10 instead of Monomer 1. Yield 43%.

Example 1-12

Synthesis of Monomer 12

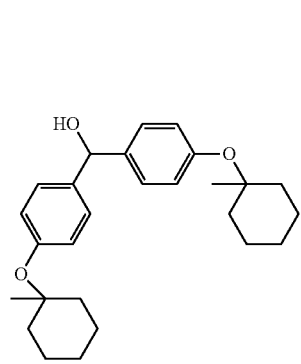

Alcohol 3

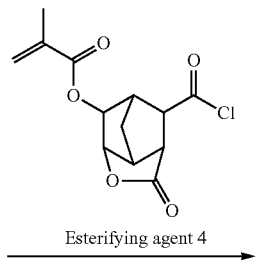

Esterifying agent 4

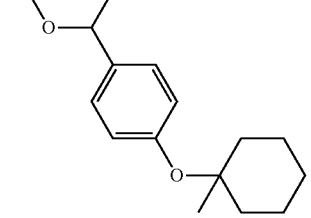

Monomer 12

Monomer 12 was obtained by the same procedure as in Example 1-4-2 aside from using Esterifying agent 4 instead of Esterifying agent 1. Yield 82%.

Example 1-13

Synthesis of Monomer 13

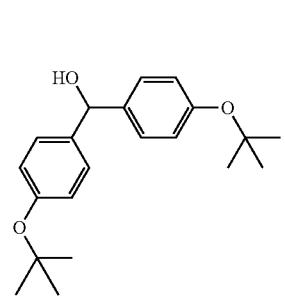

Alcohol 1

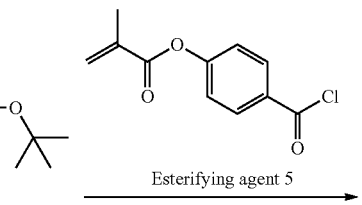

Esterifying agent 5

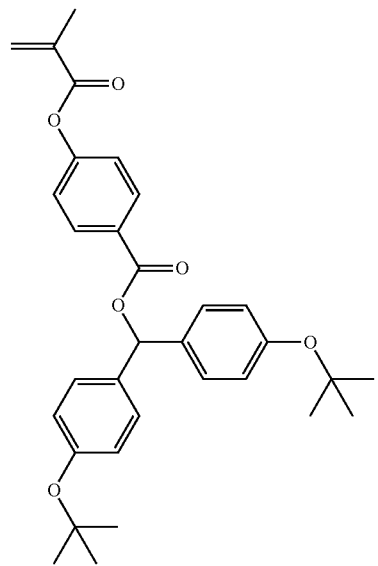

Monomer 13

Monomer 13 was obtained by the same procedure as in Example 1-1-2 aside from using Esterifying agent 5 instead of Esterifying agent 1. Yield 74%.

Example 1-14

Synthesis of Monomer 14

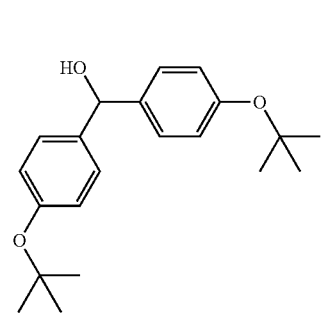

Alcohol 1

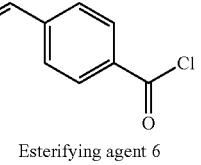

Esterifying agent 6

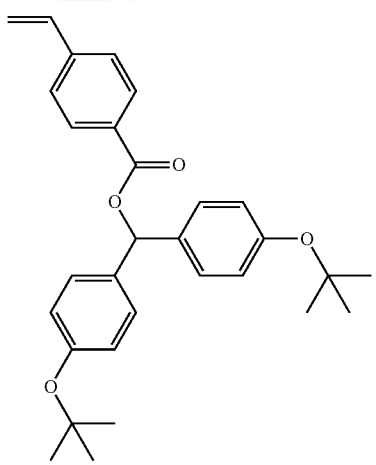

Monomer 14

Monomer 14 was obtained by the same procedure as in Example 1-1-2 aside from using Esterifying agent 6 instead of Esterifying agent 1. Yield 70%.

Example 1-15

Synthesis of Monomer 15

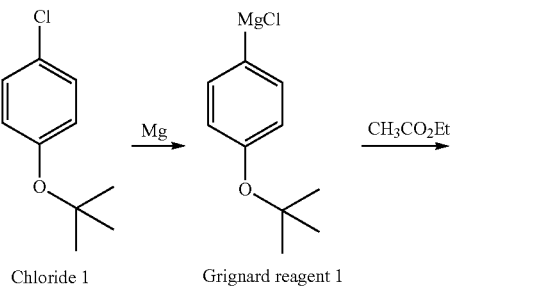

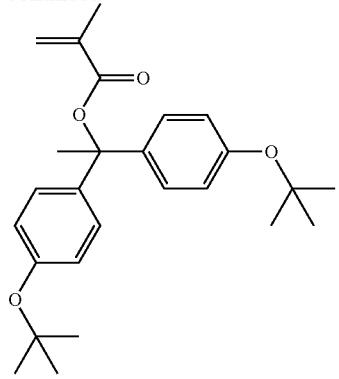

Monomer 15

Example 1-15-1

Synthesis of Alcohol 8

Alcohol 8 was obtained by the same procedure as in Example 1-1-1 aside from using ethyl acetate instead of ethyl formate. Yield 73%.

Example 1-15-2

Synthesis of Monomer 15

Monomer 15 was obtained by the same procedure as in Example 1-1-2 aside from using Alcohol 8 instead of Alcohol 1 and Esterifying agent 7 instead of Esterifying agent 1. Yield 86%.

Monomers 1 to 15 synthesized in Examples 1-1 to 1-15 are shown below by their structure.

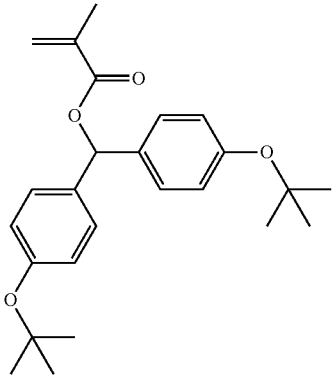

Monomer 1

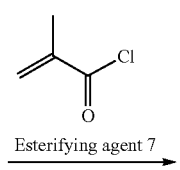

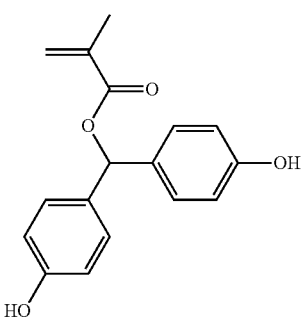

Monomer 2

Monomer 3
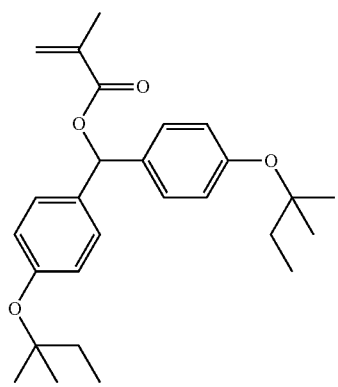
Monomer 6
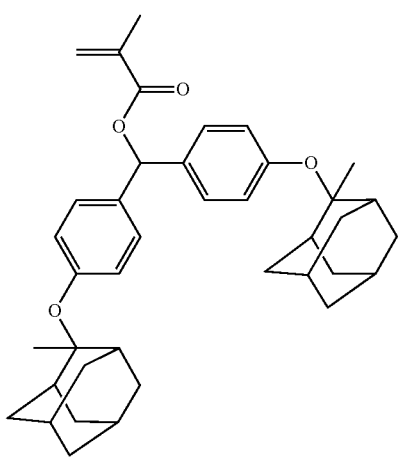
Monomer 4
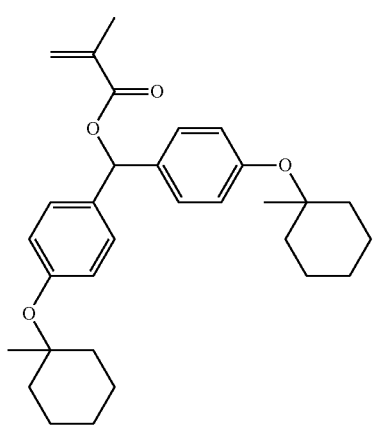
Monomer 7
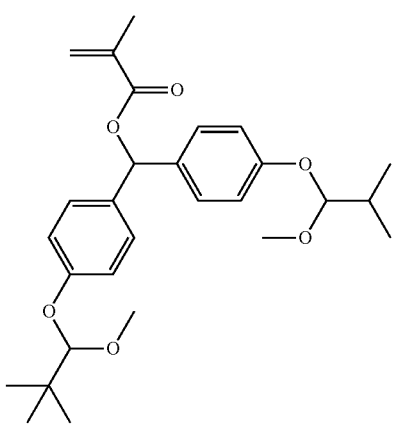
Monomer 5
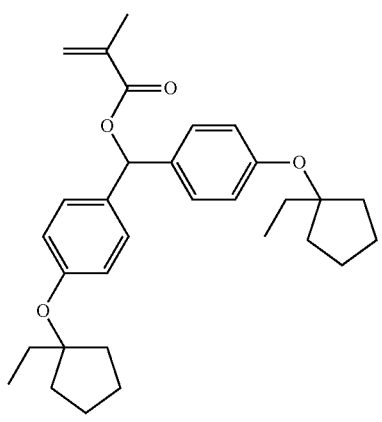
Monomer 8
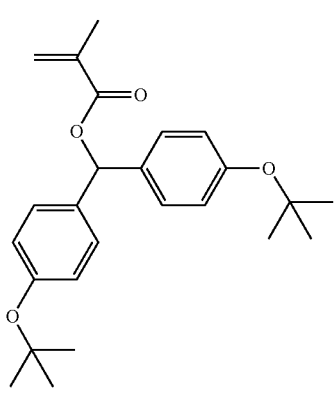

Monomer 9
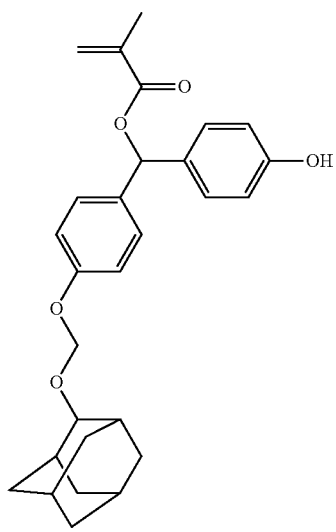
Monomer 10
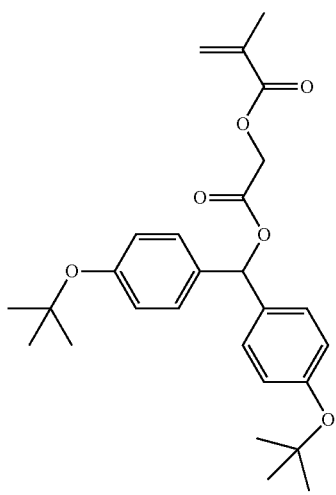
Monomer 11
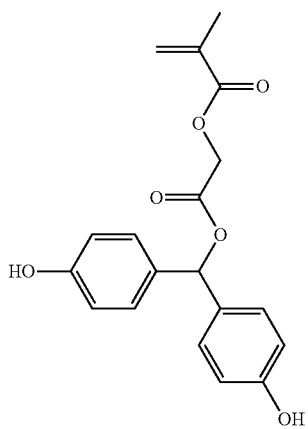
Monomer 12
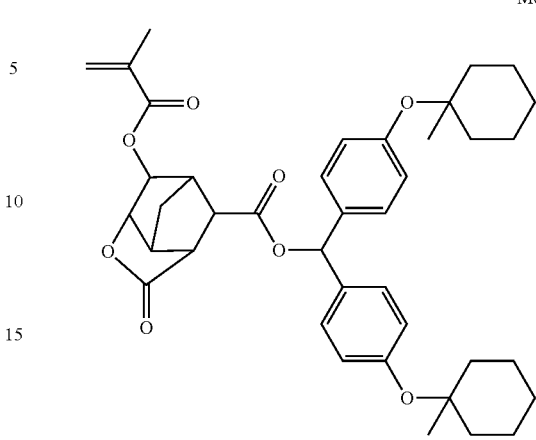
Monomer 13
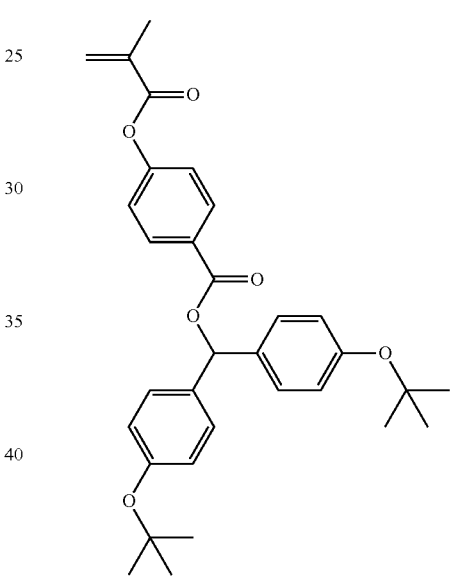
Monomer 14
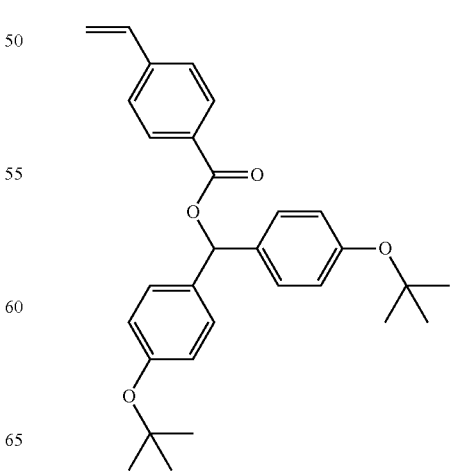

Monomer 15

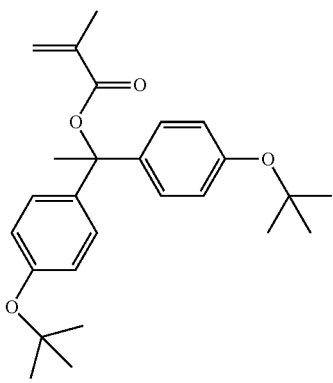

Synthesis of Polymers

Example 2-1

Synthesis of Resist Polymer 1

In nitrogen atmosphere, Monomer 1 (24.0 g), 4-hydroxyphenyl methacrylate (16.0 g), dimethyl 2,2'-azobisisobutyrate (0.35 g), and 4-mercaptoethanol (0.36 g) were dissolved in methyl ethyl ketone (55.7 g). With stirring at 80° C. in nitrogen atmosphere, the solution was added dropwise to methyl ethyl ketone (18.6 g) over 4 hours. At the end of dropwise addition, stirring was continued at 80° C. for 2 hours. The polymerization solution was cooled to room temperature and added dropwise to n-hexane (400 g). A solid precipitate was filtered and vacuum dried at 50° C. for 20 hours, obtaining a polymer in white powder solid form. The polymer, designated Resist Polymer 1, had the structure shown below. Amount 36.4 g, yield 91%.

Resist Polymer 1
(a=0.40, b=0.60, Mw=9,100)

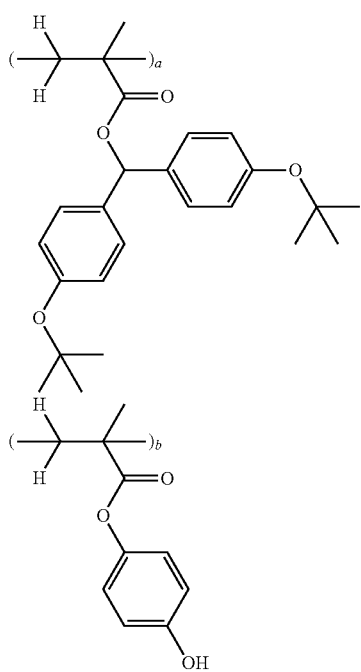

Examples 2-2 to 2-20 and Comparative Examples 1-1 to 1-3

Synthesis of Resist Polymers 2 to 20 and Comparative Polymers 1 to 3

Resist Polymers 2 to 20 and Comparative Polymers 1 to 3 were prepared by the same procedure as in Example 2-1 except that the type and amount of monomers were changed. A ratio of monomers incorporated is on a molar basis.

Resist Polymer 2
(a=0.40, b=0.60, Mw=8,300)

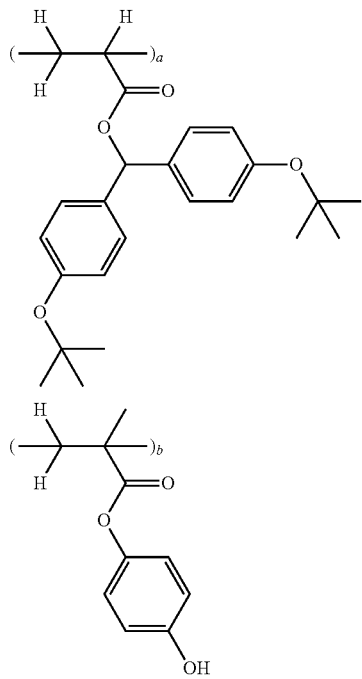

Resist Polymer 3
(a=0.40, b=0.60, Mw=9,300)

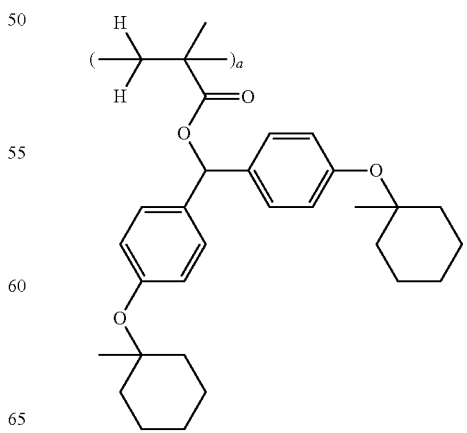

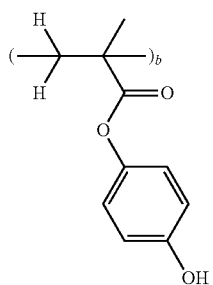
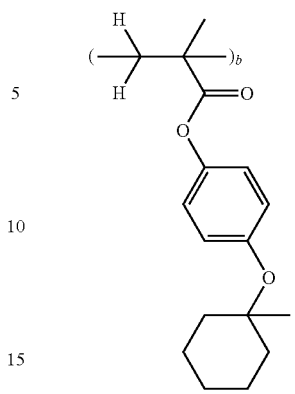
Resist Polymer 4
(a=0.40, b=0.60, Mw=9,800)
Resist Polymer 6
(a=0.35, b=0.35, c=0.30, Mw=8,600)
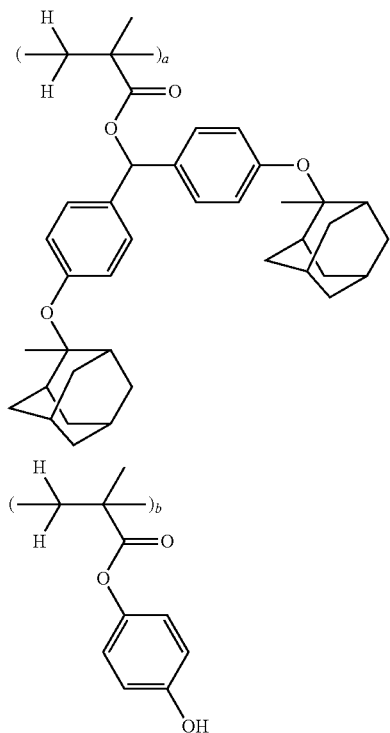
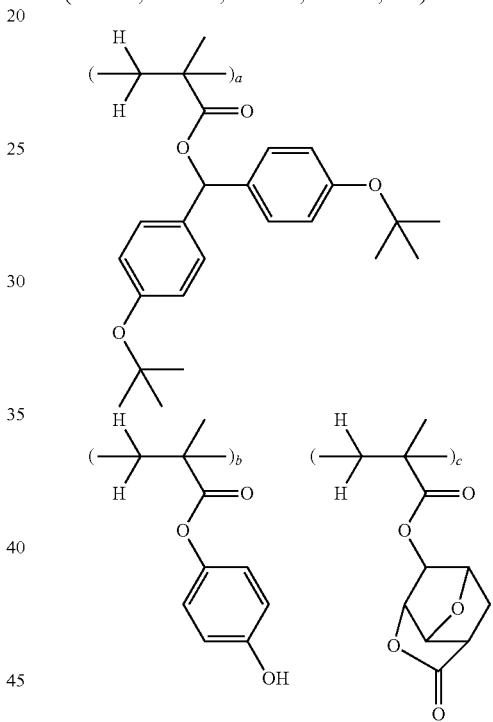
Resist Polymer 5
(a=0.35, b=0.65, Mw=9,300)
Resist Polymer 7
(a=0.35, b=0.35, c=0.30, Mw=8,500)
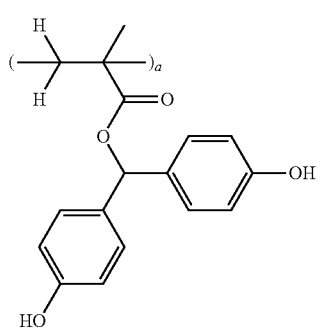
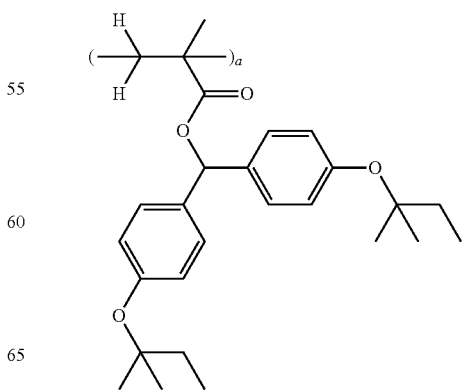

-continued
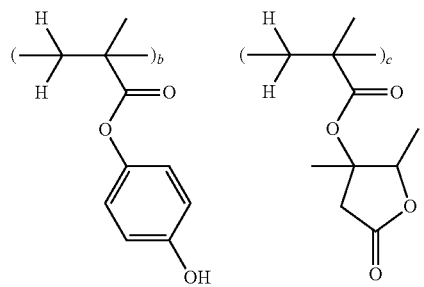
Resist Polymer 8
(a=0.35, b=0.35, c=0.30, Mw=8,500)
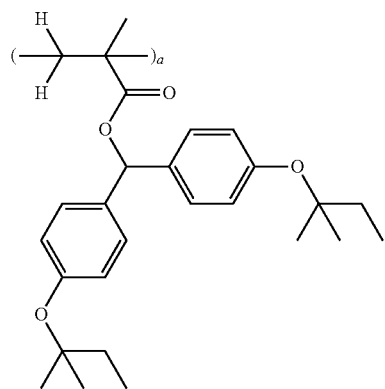
Resist Polymer 9
(a=0.20, b=0.20, c=0.30, d=0.30, Mw=8,600)
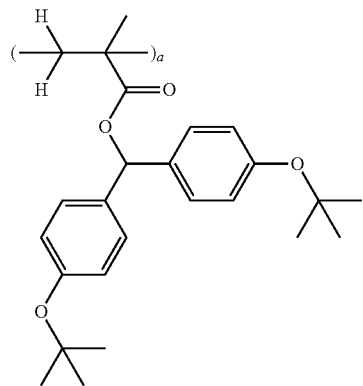
-continued
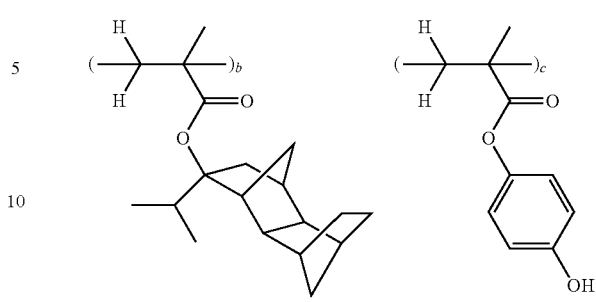
Resist Polymer 10
(a=0.20, b=0.20, c=0.30, d=0.30, Mw=8,800)
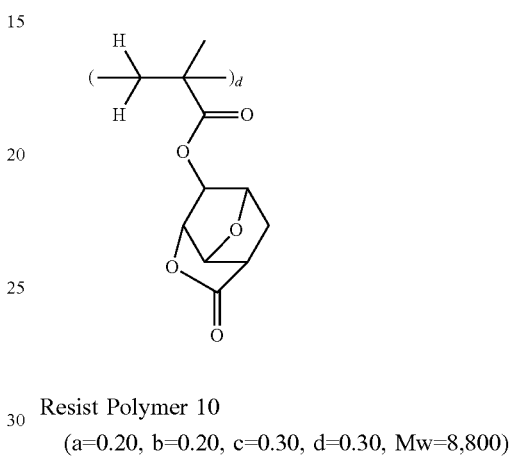
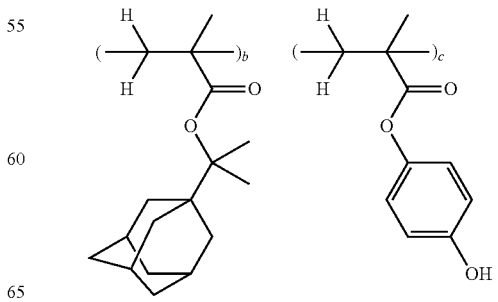

-continued
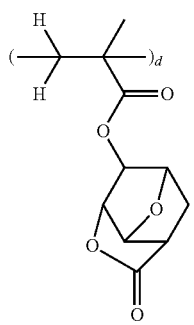
Resist Polymer 11
(a=0.20, b=0.20, c=0.30, d=0.30, Mw=8,500)
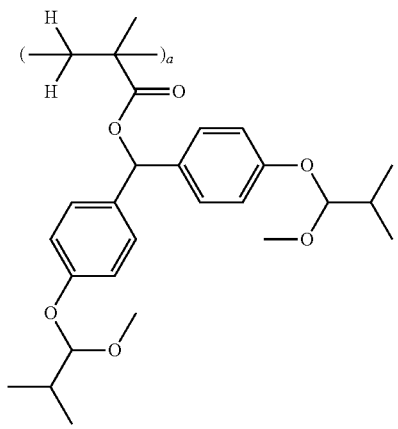
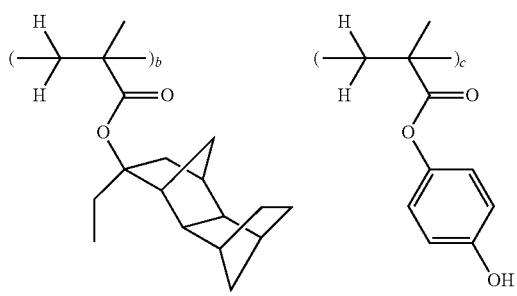
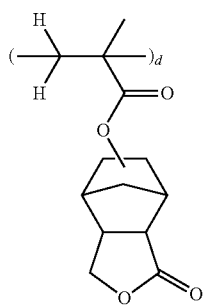
Resist Polymer 12
(a=035, b=0.10, c=0.30, d=0.25, Mw=8,500)
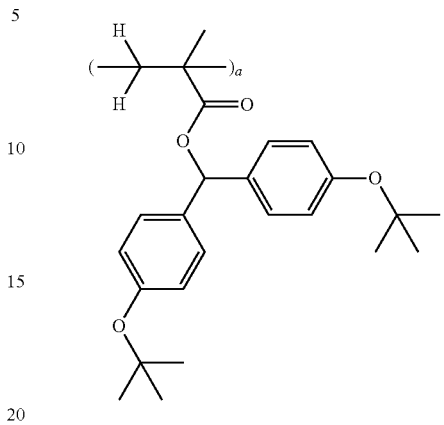
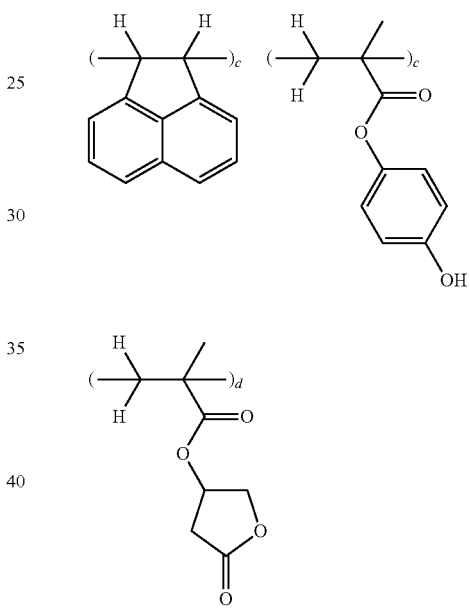
Resist Polymer 13
(a=0.30, b=0.20, c=0.40, d=0.10, Mw=10,600)
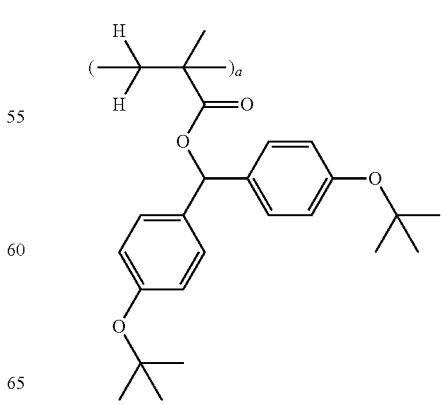

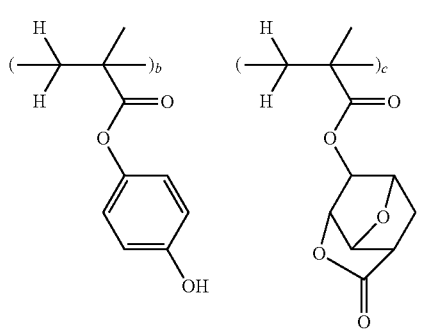
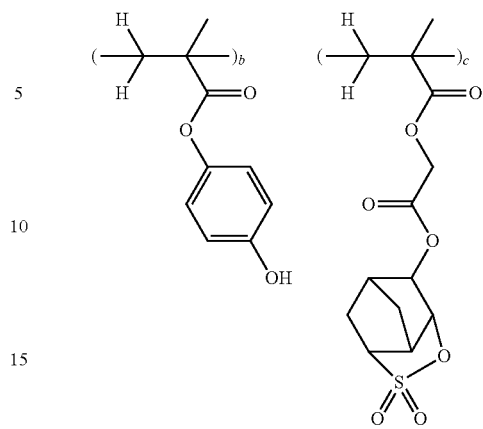
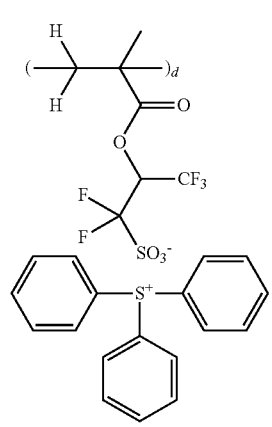
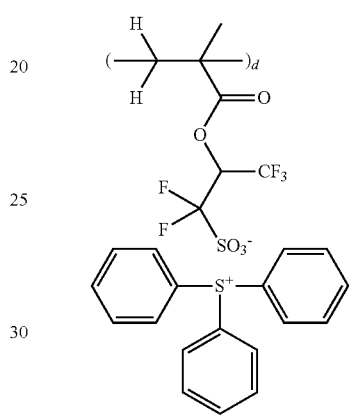
Resist Polymer 15
(a=0.30, b=0.20, c=0.35, d=0.15, Mw=10,900)
Resist Polymer 14
(a=0.30, b=0.20, c=0.40, d=0.10, Mw=11,100)
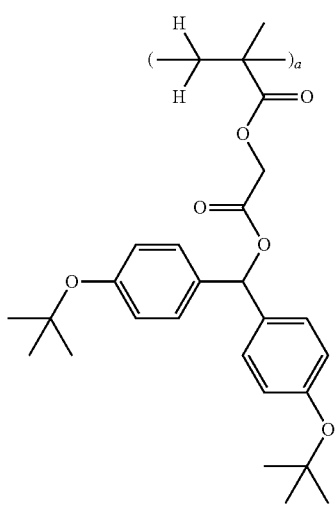
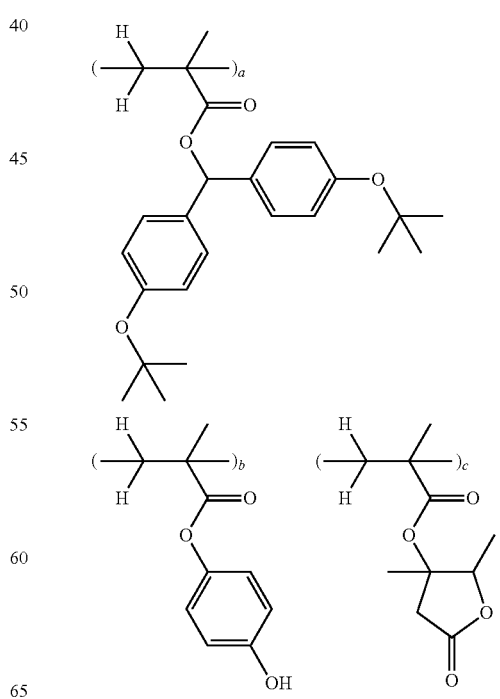

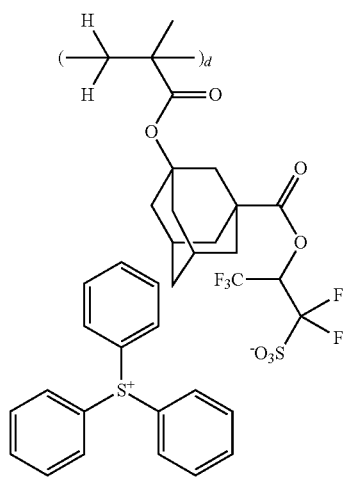
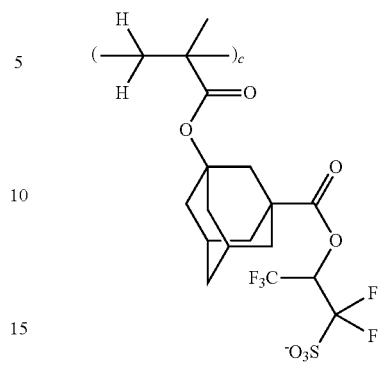
Resist Polymer 17
(a=0.10, b=0.10, c=0.70, d=0.10, Mw=13,000)
Resist Polymer 16
(a=0.30, b=0.55, c=0.15, Mw=10,200)
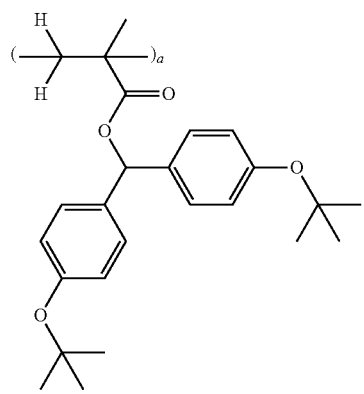
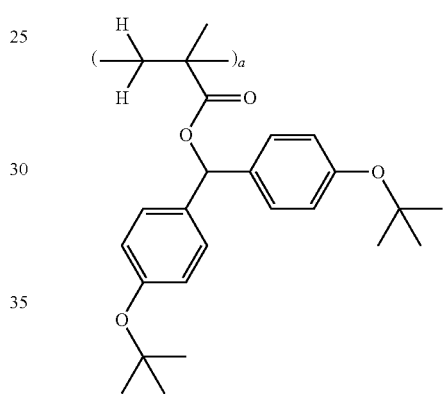
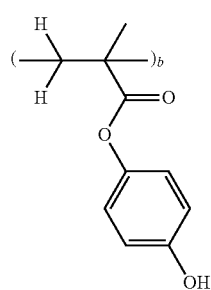
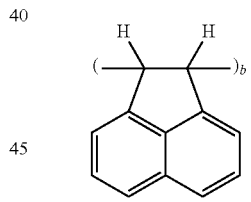
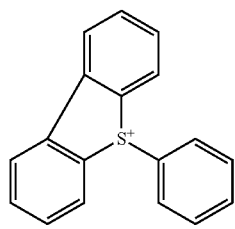
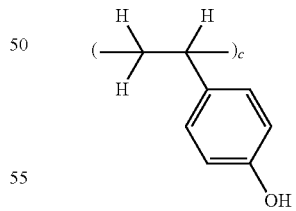
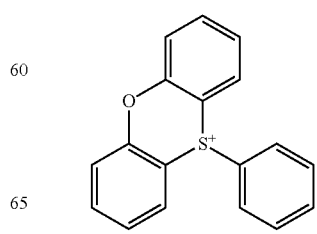

-continued
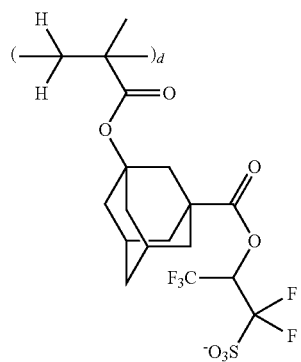
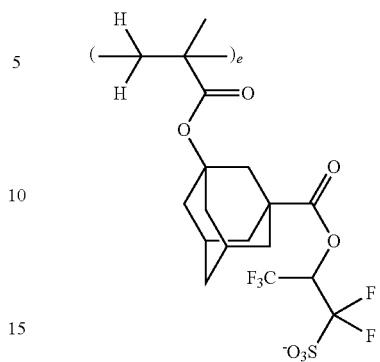
Resist Polymer 18
(a=0.15, b=0.15, c=0.30, d=0.25, e=0.15, Mw=11,000)
Resist Polymer 19
(a=0.15, b=0.15, c=0.30, d=0.25, e=0.15, Mw=12,100)
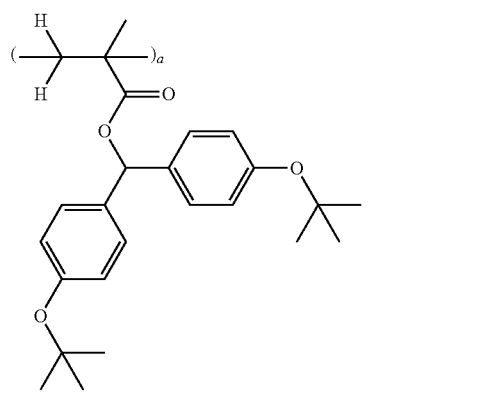
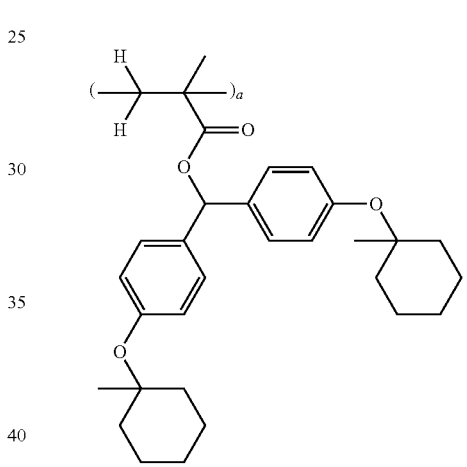
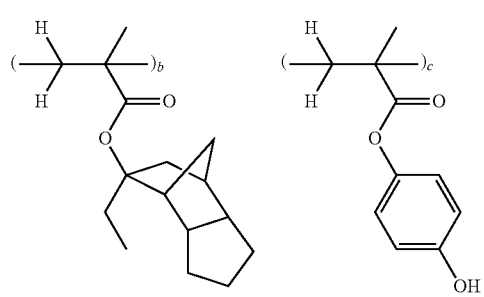
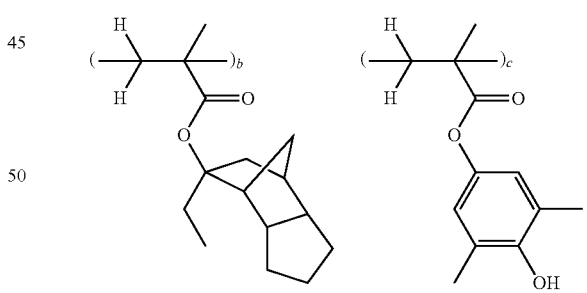
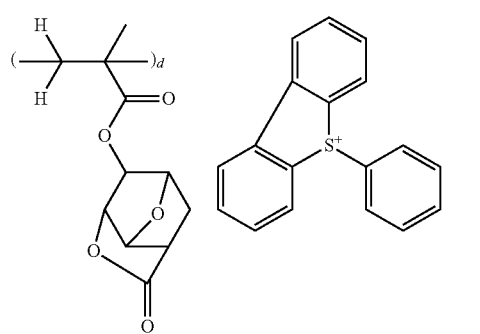
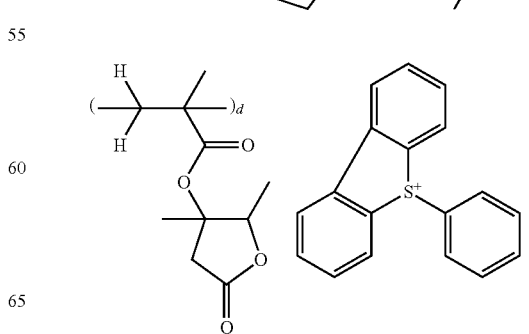

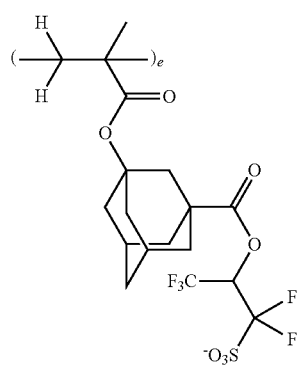
Resist Polymer 20
(a=0.15, b=0.15, c=0.30, d=0.25, e=0.15, Mw=11,700)
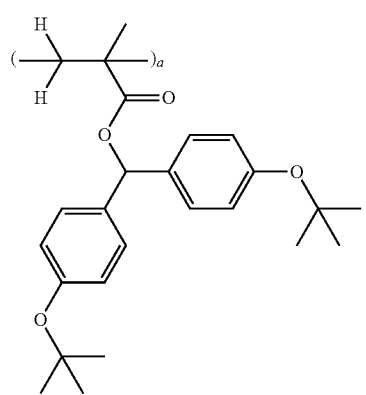
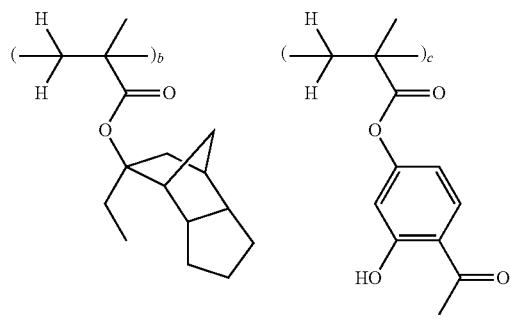
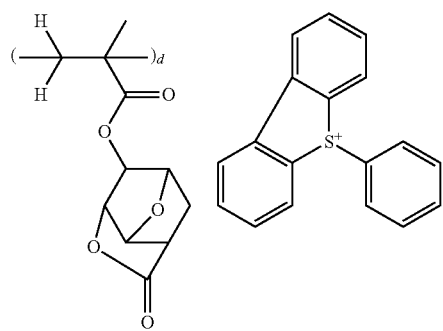
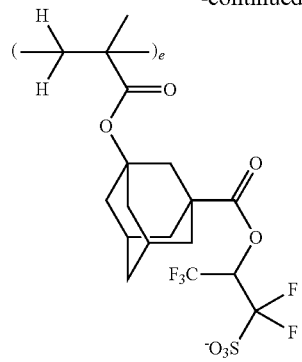
Comparative Polymer 1
(a=0.40, b=0.60, Mw=6,800)
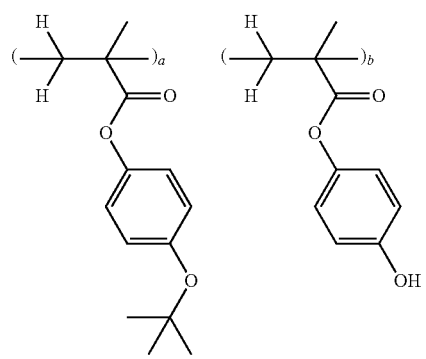 [SMILES: CCC(C)(C)C(=O)Oc1ccc(OC(C)(C)C)cc1 ; CCC(C)(C)C(=O)Oc1ccc(O)cc1]
Comparative Polymer 2
(a=0.20, b=0.20, c=0.30, d=0.30, Mw=8,000)
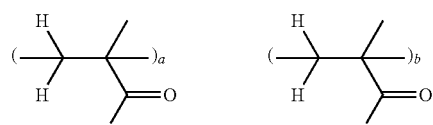
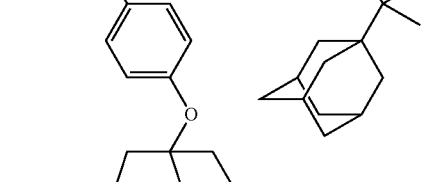
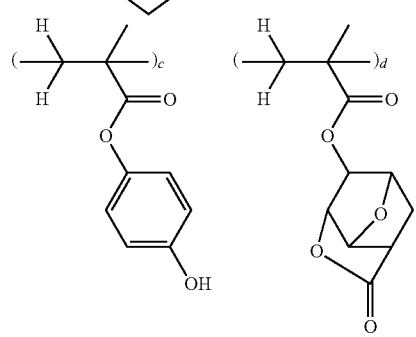

Comparative Polymer 3
(a=0.15, b=0.15, c=0.30, d=0.25, e=0.15, Mw=11,300)

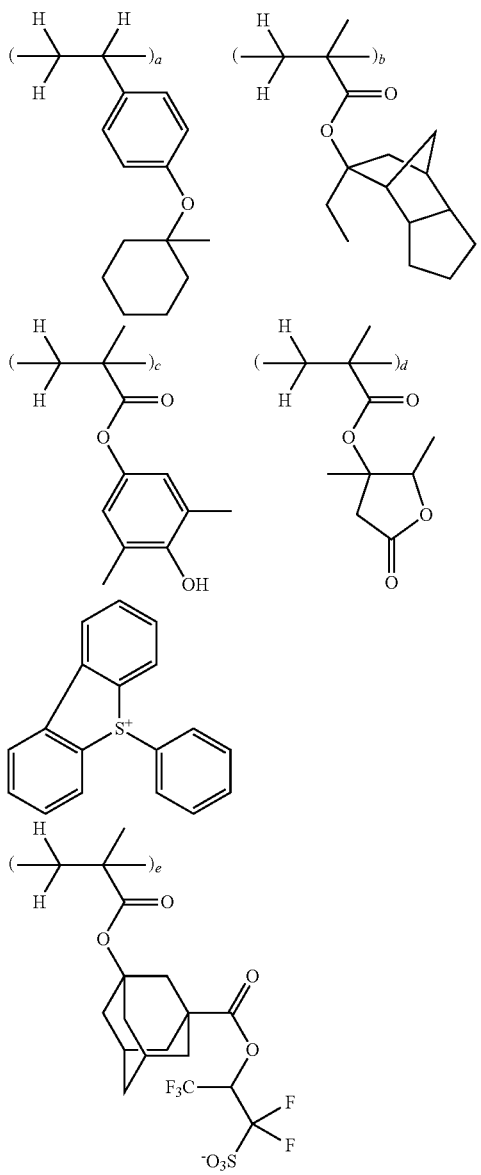

Preparation of Resist Composition

Examples 3-1 to 3-23 and Comparative Examples 2-1 to 2-3

Positive resist compositions (R-1 to R-23, R-24 to R-26) were prepared by dissolving a polymer (Resist Polymers 1 to 20, Comparative Polymers 1 to 3), a photoacid generator, quencher, and water-repellent polymer in a solvent in accordance with the recipe shown in Table 1, and filtering through a Teflon® filter having a pore size of 0.2 μm. The solvent contained 0.01 wt % of a surfactant KH-20 (Asahi Glass Co., Ltd.).

The components in Table 1 are as identified below.

Acid Generators:
PAG1 to PAG3 of the following structural formulae

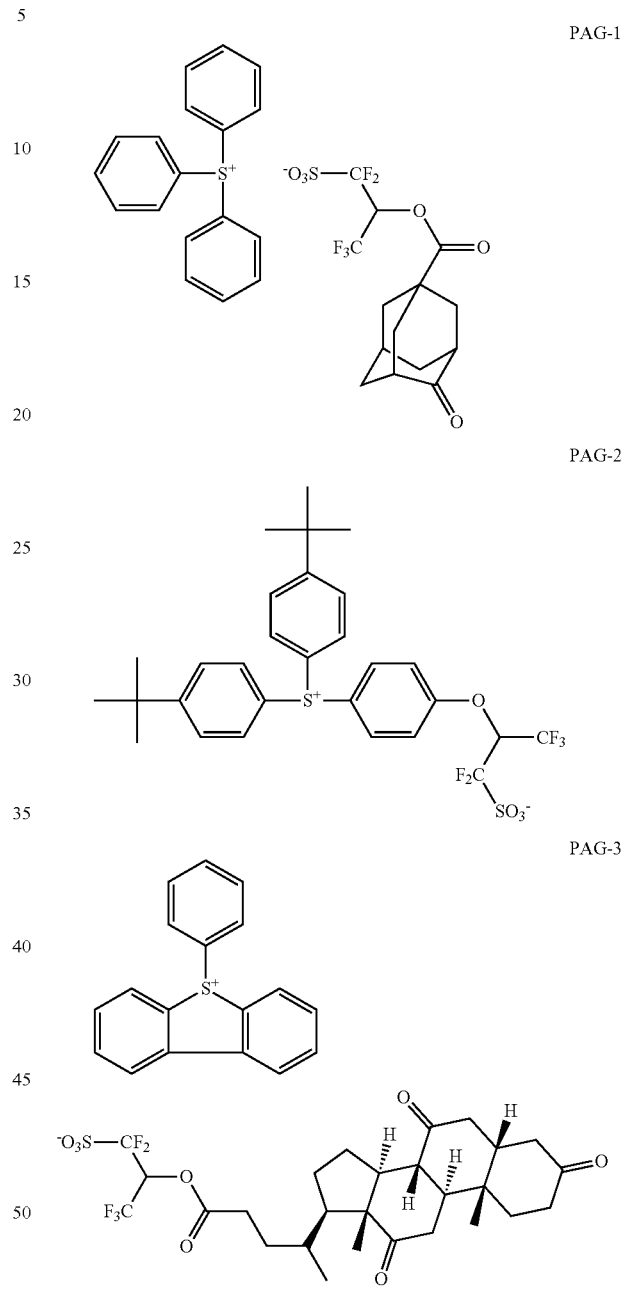

Quenchers: Q-1, Q-2 of the Following Structural Formulae

Q-2

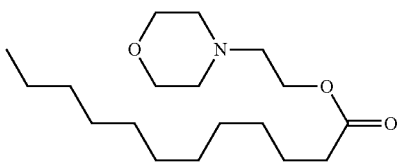

Organic Solvents:
propylene glycol monomethyl ether acetate (PGMEA)
cyclohexanone (CyH)

EUV Lithography Test

Examples 4-1 to 4-23 and Comparative Examples 3-1 to 3-3

A silicon-containing undercoat material (SHB-A940 by Shin-Etsu Chemical Co., Ltd.) was coated onto a silicon substrate of diameter 4 inches and heated at 220° C. for 60 seconds to form a resist undercoat of 35 nm thick. The resist composition (R-1 to R-23, R-24 to R-26) was spin coated onto the coated substrate and pre-baked on a hot plate at 110° C. for 60 seconds to form a resist film of 30 nm thick. Using an exposure tool (NA 0.3, Pseudo-PSM mask), the resist film was exposed to EUV.

TABLE 1

|  |  | Resist composition | Resin (pbw) | Acid generator (pbw) | Quencher (pbw) | Solvent (pbw) |
|---|---|---|---|---|---|---|
| Example | 3-1 | R-1 | Resist Polymer 1 (100) | PAG-3 (20.0) | Q-2 (1.4) | PGMEA(1,000) CyH(2,000) |
|  | 3-2 | R-2 | Resist Polymer 2 (100) | PAG-3 (20.0) | Q-2 (1.4) | PGMEA(1,000) CyH(2,000) |
|  | 3-3 | R-3 | Resist Polymer 3 (100) | PAG-3 (20.0) | Q-2 (1.4) | PGMEA(1,000) CyH(2,000) |
|  | 3-4 | R-4 | Resist Polymer 4 (100) | PAG-3 (20.0) | Q-2 (1.4) | PGMEA(1,000) CyH(2,000) |
|  | 3-5 | R-5 | Resist Polymer 5 (100) | PAG-3 (20.0) | Q-2 (1.4) | PGMEA(1,000) CyH(2,000) |
|  | 3-6 | R-6 | Resist Polymer 6 (100) | PAG-3 (20.0) | Q-2 (1.4) | PGMEA(1,000) CyH(2,000) |
|  | 3-7 | R-7 | Resist Polymer 7 (100) | PAG-3 (20.0) | Q-2 (1.4) | PGMEA(1,000) CyH(2,000) |
|  | 3-8 | R-8 | Resist Polymer 8 (100) | PAG-3 (20.0) | Q-2 (1.4) | PGMEA(1,000) CyH(2,000) |
|  | 3-9 | R-9 | Resist Polymer 9 (100) | PAG-3 (20.0) | Q-2 (1.4) | PGMEA(1,000) CyH(2,000) |
|  | 3-10 | R-10 | Resist Polymer 10 (100) | PAG-3 (20.0) | Q-2 (1.4) | PGMEA(1,000) CyH(2,000) |
|  | 3-11 | R-11 | Resist Polymer 11 (100) | PAG-3 (20.0) | Q-2 (1.4) | PGMEA(1,000) CyH(2,000) |
|  | 3-12 | R-12 | Resist Polymer 12 (100) | PAG-3 (20.0) | Q-2 (1.4) | PGMEA(1,000) CyH(2,000) |
|  | 3-13 | R-13 | Resist Polymer 13 (100) | — | Q-2 (1.4) | PGMEA(1,000) CyH(2,000) |
|  | 3-14 | R-14 | Resist Polymer 14 (100) | — | Q-2 (1.4) | PGMEA(1,000) CyH(2,000) |
|  | 3-15 | R-15 | Resist Polymer 15 (100) | — | Q-2 (1.4) | PGMEA(1,000) CyH(2,000) |
|  | 3-16 | R-16 | Resist Polymer 16 (100) | — | Q-2 (1.4) | PGMEA(1,000) CyH(2,000) |
|  | 3-17 | R-17 | Resist Polymer 17 (100) | — | Q-2 (1.4) | PGMEA(1,000) CyH(2,000) |
|  | 3-18 | R-18 | Resist Polymer 18 (100) | — | Q-2 (1.4) | PGMEA(1,000) CyH(2,000) |
|  | 3-19 | R-19 | Resist Polymer 19 (100) | — | Q-2 (1.4) | PGMEA(1,000) CyH(2,000) |
|  | 3-20 | R-20 | Resist Polymer 20 (100) | — | Q-2 (1.4) | PGMEA(1,000) CyH(2,000) |
|  | 3-21 | R-21 | Resist Polymer 6 (100) | PAG-1 (15.0) | Q-2 (1.4) | PGMEA(1,000) CyH(2,000) |
|  | 3-22 | R-22 | Resist Polymer 6 (100) | PAG-2 (20.0) | Q-2 (1.4) | PGMEA(1,000) CyH(2,000) |
|  | 3-23 | R-23 | Resist Polymer 20 (100) | — | Q-1 (1.4) | PGMEA(1,000) CyH(2,000) |
| Comparative Example | 2-1 | R-24 | Comparative Polymer 1 (100) | PAG-3 (20.0) | Q-2 (1.4) | PGMEA(1,000) CyH(2,000) |
|  | 2-2 | R-25 | Comparative Polymer 2 (100) | PAG-3 (20.0) | Q-2 (1.4) | PGMEA(1,000) CyH(2,000) |
|  | 2-3 | K-26 | Comparative Polymer 3 (100) | PAG-3 (20.0) | Q-2 (1.4) | PGMEA(1,000) CyH(2,000) |

Immediately after the exposure, the resist film was baked (PEB) on a hot plate at the temperature shown in Table 2 for 60 seconds and puddle developed in a 2.38 wt % TMAH aqueous solution for 20 seconds to form a positive pattern.

Resolution is a minimum size at the exposure dose (sensitivity) that provides a 1:1 resolution of a 20-nm line-and-space pattern. The 20-nm L/S pattern was measured for roughness (LWR) under SEM.

The resist composition is shown in Table 2 together with the sensitivity and resolution of EUV lithography.

TABLE 2

| | | Resist composition | PEB temp. (° C.) | Sensitivity (mJ/cm$^2$) | Resolution (nm) | LWR (nm) |
|---|---|---|---|---|---|---|
| Example | 4-1 | R-1 | 85 | 32 | 20 | 3.9 |
| | 4-2 | R-2 | 75 | 35 | 21 | 3.9 |
| | 4-3 | R-3 | 85 | 27 | 19 | 3.6 |
| | 4-4 | R-4 | 90 | 29 | 19 | 3.8 |
| | 4-5 | R-5 | 85 | 26 | 19 | 3.8 |
| | 4-6 | R-6 | 85 | 34 | 19 | 3.6 |
| | 4-7 | R-7 | 30 | 31 | 18 | 3.6 |
| | 4-8 | R-8 | 70 | 32 | 20 | 3.6 |
| | 4-9 | R-9 | 75 | 28 | 19 | 3.6 |
| | 4-10 | R-10 | 75 | 29 | 20 | 3.3 |
| | 4-11 | R-11 | 70 | 27 | 20 | 3.3 |
| | 4-12 | R-12 | 80 | 34 | 19 | 3.1 |
| | 4-13 | R-13 | 80 | 31 | 18 | 2.9 |
| | 4-14 | R-14 | 80 | 30 | 18 | 2.8 |
| | 4-15 | R-15 | 80 | 29 | 17 | 3.0 |
| | 4-16 | R-16 | 80 | 26 | 19 | 3.2 |
| | 4-17 | R-17 | 85 | 36 | 24 | 3.9 |
| | 4-18 | R-18 | 75 | 28 | 17 | 3.3 |
| | 4-19 | R-19 | 75 | 26 | 17 | 3.4 |
| | 4-20 | R-20 | 75 | 25 | 17 | 3.5 |
| | 4-21 | R-21 | 85 | 36 | 20 | 3.0 |
| | 4-22 | R-22 | 85 | 35 | 19 | 3.3 |
| | 4-23 | R-23 | 75 | 28 | 19 | 3.4 |
| Comparative Example | 3-1 | R-24 | 85 | 36 | 25 | 4.3 |
| | 3-2 | R-25 | 75 | 33 | 28 | 4.5 |
| | 3-3 | R-26 | 75 | 30 | 23 | 4.0 |

EB Writing Test

Examples 5-1 to 5-4 and Comparative Examples 4-1 to 4-3

Using a coater/developer system Clean Track Mark 5 (Tokyo Electron Ltd.), the positive resist composition (R-1 to R-23, R-24 to R-26) was spin coated onto a silicon substrate of diameter 6 inches and pre-baked on a hot plate at 110° C. for 60 seconds to form a resist film of 100 nm thick. Using a system HL-800D (Hitachi Ltd.) at a HV voltage of 50 kV, the resist film was exposed imagewise to EB in a vacuum chamber.

Using Clean Track Mark 5, immediately after the exposure, the resist film was baked (PER) on a hot plate at the temperature shown in Table 3 for 60 seconds and puddle developed in a 2.38 wt % TMAH aqueous solution for 30 seconds to form a positive pattern.

Resolution is a minimum size at the exposure dose (sensitivity) that provides a 1:1 resolution of a 120-nm line-and-space pattern. The 120-nm L/S pattern was measured for roughness (LWR) under SEM.

The resist composition is shown in Table 3 together with the sensitivity and resolution of EB lithography.

TABLE 3

| | | Resist composition | PEB temp. (° C.) | Sensitivity (μC/cm$^2$) | Resolution (nm) | LWR (nm) |
|---|---|---|---|---|---|---|
| Example | 5-1 | R-1 | 90 | 29 | 80 | 5.9 |
| | 5-2 | R-10 | 90 | 31 | 75 | 5.4 |
| | 5-3 | R-17 | 95 | 32 | 70 | 4.8 |
| | 5-4 | R-20 | 90 | 31 | 65 | 4.3 |
| Comparative Example | 4-1 | R-24 | 90 | 29 | 90 | 7.2 |
| | 4-2 | R-25 | 85 | 30 | 85 | 6.9 |
| | 4-3 | R-26 | 85 | 27 | 80 | 6.6 |

Dry Etching Test

Examples 6-1 to 6-4 and Comparative Examples 5-1 to 5-2

Each polymer, 2 g, was thoroughly dissolved in 10 g of cyclohexanone, and passed through a filter having a pore size of 0.2 μm, obtaining a polymer solution. The polymer solution was spin coated onto a silicon substrate and baked to form a polymer film of 300 nm thick. Using a dry etching instrument TE-8500P (Tokyo Electron Ltd.), the polymer film was etched with $CHF_3/CF_4$ gas under the following conditions.

| | |
|---|---|
| Chamber pressure | 40.0 Pa |
| RF power | 1000 W |
| Gap | 9 mm |
| $CHF_3$ gas flow rate | 3 ml/min |
| $CF_4$ gas flow rate | 30 ml/min |
| Ar gas flow rate | 100 ml/min |
| Time | 60 sec |

The difference in polymer film thickness before and after etching was determined, from which an etching rate per minute was computed. The results are shown in Table 4. A smaller value of film thickness difference, i.e., a lower etching rate indicates better etch resistance.

TABLE 4

| | | Resin | $CHF_3/CF_4$ gas etching rate (nm/mm) |
|---|---|---|---|
| Example | 6-1 | Resist Polymer 1 | 92 |
| | 6-2 | Resist Polymer 5 | 90 |
| | 6-3 | Resist Polymer 10 | 96 |
| | 6-4 | Resist Polymer 17 | 91 |
| Comparative Example | 5-1 | Comparative Polymer 1 | 96 |
| | 5-2 | Comparative Polymer 2 | 104 |

It is evident from Tables 2 and 3 that the resist compositions using the inventive polymers show satisfactory resolution, sensitivity and edge roughness. These polymers have good dry etch resistance as demonstrated by a smaller difference in film thickness before and after etching in Table 4.

Japanese Patent Application No. 2015-137416 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising recurring units (a) having the formula (A):

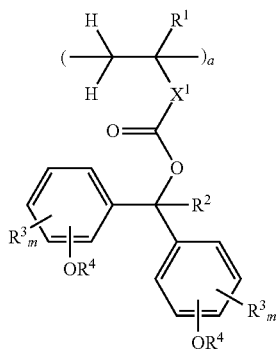

(A)

wherein $R^1$ is hydrogen or methyl, $R^2$ is hydrogen or a straight, branched or cyclic $C_1$-$C_{15}$ monovalent hydrocarbon group in which any constituent —$CH_2$— may be replaced by —O—, —C(=O)—, —C(=O)—O— or —O—C (=O)—, $R^3$ is each independently hydrogen, cyano, nitro, or a straight, branched or cyclic $C_1$-$C_6$ monovalent hydrocarbon group in which any constituent —$CH_2$— may be replaced by —O—, —C(=O)—, —C(=O)—O— or —O—C(=O)—, $R^4$ is each independently hydrogen or an acid labile group, $X^1$ is a single bond, a $C_1$-$C_{12}$ linking group having an ester moiety, ether moiety or lactone ring, a phenylene group or naphthylene group, m is an integer of 1 to 4, and a is a positive number in the range: $0 < a \leq 1.0$.

2. The polymer of claim 1 wherein the acid labile group is t-butyl, t-pentyl, methylcyclopentyl, ethylcyclopentyl, methylcyclohexyl, ethylcyclohexyl, methyladamantyl, ethyladamantyl, t-butoxycarbonyl, t-pentyloxycarbonyl, or —$CR^5R^6$—O—$R^7$, wherein $R^5$ and $R^6$ are each independently hydrogen or a straight or branched $C_1$-$C_4$ alkyl group, $R^1$ is a straight, branched or cyclic $C_1$-$C_{12}$ alkyl group or straight, branched or cyclic $C_2$-$C_{12}$ alkenyl group.

3. The polymer of claim 1, further comprising recurring units (b) containing an adhesive group selected from the group consisting of hydroxyl, carboxyl, lactone ring, carbonate, thiocarbonate, carbonyl, cyclic acetal, ether, ester, sulfonic acid ester, cyano, amide, and —O—C(=O)-G- wherein G is sulfur or NH.

4. The polymer of claim 3 wherein the recurring unit (b) is a unit containing a phenolic hydroxyl group.

5. The polymer of claim 4 wherein the recurring unit containing a phenolic hydroxyl group is selected from recurring units (b1) to (b9) having the formulae (B1) to (B9):

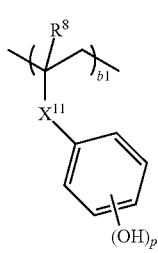

(B1)

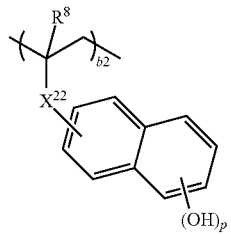

(B2)

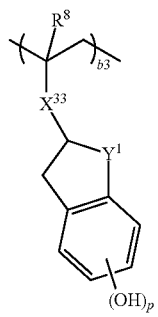

(B3)

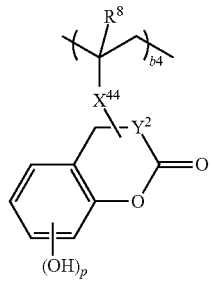

(B4)

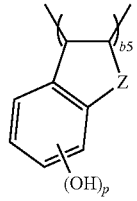

(B5)

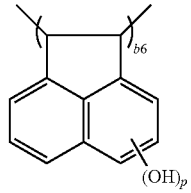

(B6)

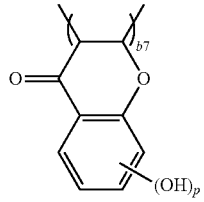

(B7)

-continued (B8)
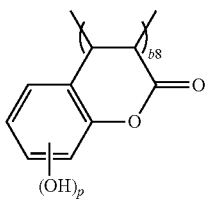

(B9)
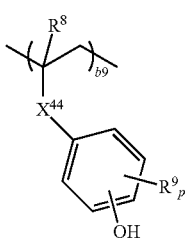

wherein $R^8$ is hydrogen or methyl, $R^9$ is $C_1$-$C_4$ alkyl, —C(=O)—$R^{9a}$, —O—C(=O)—$R^{9a}$, —C(O)—O—$R^{9a}$, cyano or nitro group, $X^{11}$ and $X^{22}$ are each independently a single bond or —C(=O)—O—$R^{10a}$—, $X^{33}$ and $X^{44}$ each are —C(=O)—O—$R^{10a}$—, $R^{9a}$ is $C_1$-$C_4$ alkyl or $C_2$-$C_4$ alkenyl, $R^{10a}$ is a single bond or a straight, branched or cyclic $C_1$-$C_{10}$ alkylene group, $Y^1$ and $Y^2$ are each independently methylene or ethylene, Z is methylene, oxygen or sulfur, p is 1 or 2, b1 to b9 are numbers in the range: 0≤b1<1.0, 0≤b2<1.0, 0≤b3<1.0, 0≤b4<1.0, 0≤b5<1.0, 0≤b6<1.0, 0≤b7<1.0, 0≤b8<1.0, 0≤b9<1.0, and 0<b1+b2+b3+b4+b5+b6+b7+b8+b9<1.0.

6. The polymer of claim 1, further comprising recurring units of at least one type selected from recurring units (c1) to (c5) having the formulae (C1) to (C5):

(C1)
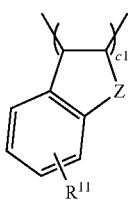

(C2)
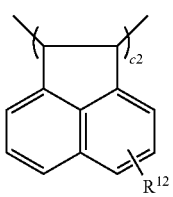

(C3)
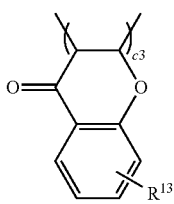

(C4)
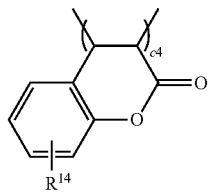

(C5)
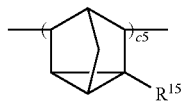

wherein $R^{11}$ to $R^{15}$ are each independently hydrogen, $C_1$-$C_{30}$ alkyl, $C_1$-$C_{30}$ alkyl in which one or more or all carbon-bonded hydrogen atoms are substituted by halogen, $C_1$-$C_5$ alkoxy, $C_1$-$C_8$ alkanoyl, $C_2$-$C_8$ alkoxycarbonyl, $C_6$-$C_{10}$ aryl, halogen, or 1,1,1,3,3,3-hexafluoro-2-propanol group, Z is methylene, oxygen or sulfur, c1 to c5 are numbers in the range: 0≤c1<1.0, 0≤c2<1.0, 0≤c3<1.0, 0≤c4<1.0, 0≤c5<1.0, and 0<c1+c2+c3+c4+c5<1.0.

7. The polymer of claim 1, further comprising recurring units of at least one type selected from sulfonium salt-containing recurring units (d1) to (d3) having the formulae (D1) to (D3):

(D1)
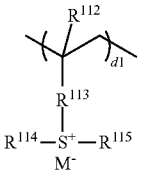

(D2)
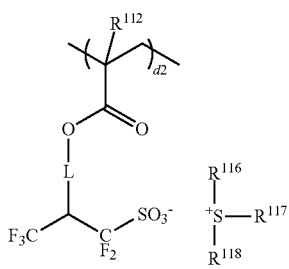

(D3)

wherein $R^{112}$ is hydrogen or methyl, $R^{113}$ is a single bond, phenylene, —O—$R^{122}$—, or —C(=O)—$Z^{22}$—$R^{122}$—, $Z^{22}$ is oxygen or NH, $R^{122}$ is a straight, branched or cyclic $C_1$-$C_6$ alkylene, $C_2$-$C_6$ alkenylene or phenylene group, which may contain a carbonyl, ester, ether or hydroxyl moiety, L is a single bond or —$Z^{33}$—C(=O)—O—, $Z^{33}$ is a straight, branched or cyclic $C_1$-$C_{20}$ divalent hydrocarbon group which may be substituted with a heteroatom, $Z^{11}$ is a single bond, methylene, ethylene, phenylene, fluorinated phenylene, —O—$R^{123}$—, or —C(=O)—$Z^{44}$—$R^{123}$—, $Z^{44}$ is oxygen or NH, $R^{123}$ is a straight, branched or cyclic $C_1$-$C_6$ alkylene, $C_2$-$C_6$ alkenylene or phenylene group, which may contain a carbonyl, ester, ether or hydroxyl moiety, $M^-$ is a non-nucleophilic counter ion, $R^{114}$, $R^{115}$, $R^{116}$, $R^{117}$, $R^{118}$, $R^{119}$, $R^{120}$, and $R^{121}$ are each independently a straight, branched or cyclic $C_1$-$C_{20}$ monovalent hydrocarbon group which may contain a heteroatom, d1, d2 and d3 are numbers in the range:

$0 \leq d1 \leq 0.5$, $0 \leq d2 \leq 0.5$, $0 \leq d3 \leq 0.5$, and $0 < d1+d2+d3 \leq 0.5$.

8. A positive resist composition comprising the polymer of claim 1, and an organic solvent.

9. The resist composition of claim 8, further comprising a photoacid generator.

10. The resist composition of claim 8, further comprising a dissolution regulator.

11. The resist composition of claim 8, further comprising a basic compound and/or surfactant.

12. A pattern forming process comprising the steps of coating the positive resist composition of claim 8 onto a substrate, baking the coating to form a resist film, exposing the resist film to high-energy radiation, and developing the exposed resist film in a developer.

* * * * *